United States Patent
Nagai et al.

(10) Patent No.: US 7,576,204 B2
(45) Date of Patent: *Aug. 18, 2009

(54) HETEROCYCLIC MACROLIDE PHARMACEUTICAL AGENT, A METHOD OF PRODUCING THE SAME AND USE OF THE SAME

(75) Inventors: Mitsuo Nagai, Tsukuba (JP); Masashi Yoshida, Iwata (JP); Toshio Tsuchida, Iwata (JP)

(73) Assignees: Mercian Corporation, Tokyo (JP); Eisai R&D Management Co., Ltd., Tokyo (JP)

( * ) Notice: Subject to any disclaimer, the term of this patent is extended or adjusted under 35 U.S.C. 154(b) by 326 days.

This patent is subject to a terminal disclaimer.

(21) Appl. No.: 10/522,733

(22) PCT Filed: Jul. 31, 2003

(86) PCT No.: PCT/JP03/09752

§ 371 (c)(1),
(2), (4) Date: Jan. 28, 2005

(87) PCT Pub. No.: WO2004/011459

PCT Pub. Date: Feb. 5, 2004

(65) Prior Publication Data

US 2006/0235002 A1    Oct. 19, 2006

(30) Foreign Application Priority Data

Jul. 31, 2002    (JP)    ............................ 2002-224111

(51) Int. Cl.
- A61K 31/497    (2006.01)
- C07D 411/00    (2006.01)
- C07D 313/04    (2006.01)

(52) U.S. Cl. ..................... 544/374; 514/254.1; 549/271
(58) Field of Classification Search ................... 514/450
See application file for complete search history.

(56) References Cited

U.S. PATENT DOCUMENTS

| 6,712,617 B2 | 3/2004 | Detmar et al. | |
| 7,026,352 B1 * | 4/2006 | Mizui et al. | ................. 514/450 |

FOREIGN PATENT DOCUMENTS

| JP | 4-352783 A | 12/1992 |
| JP | 4352783 A | 12/1992 |
| WO | WO-00/75126 A1 | 12/2000 |
| WO | WO-02/12533 A2 | 2/2002 |
| WO | WO 02/060890 A1 | 8/2002 |
| WO | WO-02/060890 A1 | 8/2002 |
| WO | WO-03/099813 A1 | 12/2003 |

OTHER PUBLICATIONS

Seki-Asano, Mitsuko et al., "Isolation and Characterization of a New 12-Membered Macrolide FD-895", J. Antibiot., 1994, vol. 47, No. 12, pp. 1395 to 1401.

Mitsuko Seki-Asano et al.; The Journal of Antibiotics; vol. 47, No. 12, pp. 1395-1401, 1994.
Bestmann, Hans Jurgen. Synthesis, 1989, vol. 6, pp. 419-423.
Bestmann, Jans Jurgen. Angew. Chem., 1983, vol. 95, No. 10, pp. 810-811.
Furstner, Alois et al. Efficient Total Syntheses of Resin Glycosides and Analogues by Ring-Closing Olefin Metathesis, J. Am. Chem. Soc., 1999, vol. 121, pp. 7814-7821.
Gunawardana, Geewananda, et al. J. Am. Chem. Soc. 1999, vol. 121, pp. 6092-6093.
Rohr, Jurgen. Angew Chem. Int. Ed., 2000, vol. 39, No. 16, pp. 2847-2849.
Kobayashi, Jun'ichi et al. *Tetrahedron Letters*, 1996, vol. 37, No. 9, pp. 1449-1450.
Hamberg, Mats. Lipids, 2000, vol. 35, No. 4, pp. 353-363.
Hamberg, Mats. Chem. Phys. Lipids, 1988, vol. 46, No. 4, pp. 235-243.
Ryuichi Morishita. "Recent Progress in Gene Therapy for Cardiovascular Disease", Circ Journal, vol. 66, pp. 1077-1086.
Moon-Seok Cha, "Endogenous Production of Nitric Oxide by vascular Endothelial Growth Factor Down-Regulates Proliferation of Choriocarcinoma Cells", Biochemical and Biophysical Research Communications, vol. 282, pp. 1061-1066.
Sakai et al., "Shinki ko-shuyo kassei busshitsu pladienolide ni kansuru kenkyu (1)-shinki 12-inkan macrolide pladeienolide B no tanri to kozo", Japan Society for Bioscience, Biotechnology, and Agrochemistry, Taikai Koen Yoshishu, Mar. 2003, p. 123
Akifumi et al., "Shinki ko-shuyo kassei busshitsu pladienolide ni kansuru kenkyu (2) VEGF sansei yokusei kassei o shihyo to shita pladienolide-rui no kozo kassei sokan", Japan Society for Bioscience, Biotechnology, and Agrochemistry, Taikai Koen Yoshishu, Mar. 2003, p. 124.
Keiji et al., "Shinki ko-shuyo kassei busshitsu pladienolide ni kansuru kenkyu (3)- pladienolide-rui no yakuri kassei (in vitro, in vivo)", Japan Society for Bioscience, Biotechnology, and Agrochemistry, Taikai Koen Yoshishu, Mar. 2003, p. 124.
Proceedings for 2003 Annual Meeting of Japan Society for Bioscience, Biotechnology, and Agrochemistry, pp. 123-124, (2003).

* cited by examiner

*Primary Examiner*—Rita J Desai
*Assistant Examiner*—John Mabry
(74) *Attorney, Agent, or Firm*—Birch, Stewart, Kolasch & Birch LLP

(57) ABSTRACT

A compound represented by the following general formula (I):

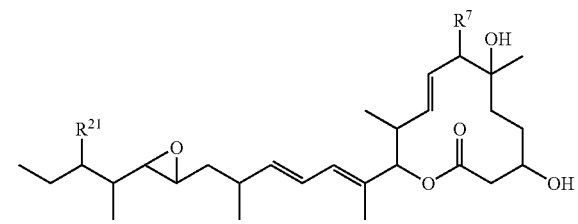

(I) wherein $R^7$ and $R^{21}$ are the same or different and each represents optionally substituted $C_{2-22}$ alkoxy, etc.; a pharmaceutically acceptable salt thereof or hydrates of the same. The compound (1) inhibits angiogenesis and inhibits the production of VEGF particularly under hypoxic conditions, which makes it useful as a remedy for solid cancer.

4 Claims, No Drawings

SEQUENCE LISTING

<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: PCR Primer based on VEGF cDNA

<400> SEQUENCE: 1
atgaactttc tgctgtcttg ggtgcattgg                                    30

```
<210> SEQ ID NO 2
<211> LENGTH: 29
<212> TYPE: DNA
<213> ORGANISM: Artificial Sequence
<220> FEATURE:
<223> OTHER INFORMATION: PCR Primer based on VEGF cDNA

<400> SEQUENCE: 2
ctggccttgg tgaggtttgt accgcataa                                    29
```

HETEROCYCLIC MACROLIDE PHARMACEUTICAL AGENT, A METHOD OF PRODUCING THE SAME AND USE OF THE SAME

TECHNICAL FIELD

The present invention relates to a 12-membered ring macrolide compound useful as a pharmaceutical agent, a method for producing the same, and use of the same.

BACKGROUND ART

Conventionally, compounds having cytotoxicity have been used as antitumor agents, and a lot of screenings have been carried out using cytotoxicity as an index. As a result, since most of the conventional antitumor agents affect cancer cells and, at the same time, normal tissues with active cell proliferation, for example, the bone marrow and intestine epithelium, QOL of patients is not sufficiently improved.

Further, under existing circumstances, antitumor agents have come to have a rather beneficial effect on treating leukemia, but are not necessarily effective for solid tumors. Therefore, antitumor agents that are effective for solid tumors and are highly safe have been strongly demanded.

Fermentation products of microorganisms have been screened mainly using cytotoxicity in vitro as an index, in order to use these products as antitumor agents. As a result, many cytotoxic compounds have been discovered. However, most of the compounds have been confirmed to show cytotoxic activities only in vitro, and few compounds have been found to have an antitumor activities in vivo. Furthermore, very few compounds exhibit efficacy against solid cancers.

DISCLOSURE OF THE INVENTION

An object of the present invention is to discover compounds that is show antitumor activities not only in vitro but also in vivo, and have antitumor activities on solid cancers from fermentation products of microorganism, or their derivatives.

It is considered that tumorgenesis of normal cells is caused by mutations of a gene in the cell occurs so that an abnormal gene is expressed. In this situation, the present inventors have conducted extensive studies, based on the assumption that alteration of gene expression in tumor cells can cause inhibition of proliferation of tumor cells, namely, proliferation of tumor cells can be inhibited by, for example, changing the gene of oncogene or tumor suppressor gene, or changing the gene expression of a gene involved in cell cycle. The present inventors have screened fermentation products of various microorganisms and their derivatives using VEGF (Vascular Endothelial Growth Factor) production by U251 cells under hypoxic stimulation as an index, in the expectation that compounds which alter gene expression, in particular, compounds which inhibit VEGF production under low hypoxic condition, inhibit angiogenesis by tumors and, furthermore, exhibit antitumor activity against solid cancers. As a result, the present inventors have discovered a 12-membered ring macrolide compound, named 11107B, represented by the following formula, which is a novel physiologically active substance that inhibits VEGF production under hypoxic conditions in vitro and, further, inhibits proliferation of solid cancer cells in vivo.

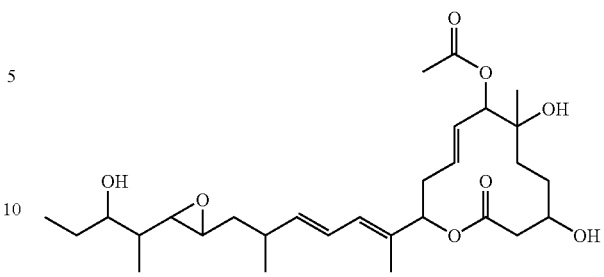

As a result of further extensive studies, the present inventors have found that a 11107B compound chemically modified on both the 7-position and the 21-position (hereinafter referred to as "7,21-positions modified 11107B derivative") has activity of inhibiting VEGF production and proliferation of tumor cells. These findings have led to the accomplishment of the present invention.

Given as a related art, most structurally similar to the compound of the present invention is FD-895, which is a 12-membered ring macrolide compound (JP-A-04-352783) represented by the formula (XIV):

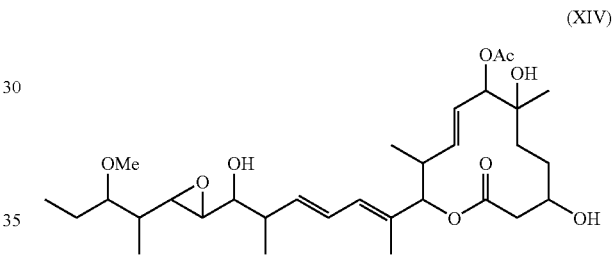

(XIV)

The above-described publication discloses that FD-895 has cytotoxic activity in vitro against P388 mouse leukemia cells, L-1210 mouse leukemia cells, and HL-60 human leukemia cells in a RPM-1640 culture medium (Column No. 6, Table 2 of the publication). However, it is reported that FD-895 did not show antitumor activity in an in vivo experiment using P388 mouse leukemia cells (Seki-Asano M. et al., J. Antibiotics, 47, 1395-1401, 1994).

Furthermore, as described later, since FD-895 is instable in an aqueous solution, it is expected to be inappropriate to mix the compound with an infusion solution upon administered. Therefore, FD-895 does not have sufficient qualities as an antitumor agent.

That is, the present invention relates to:
1. A compound represented by the formula (I):

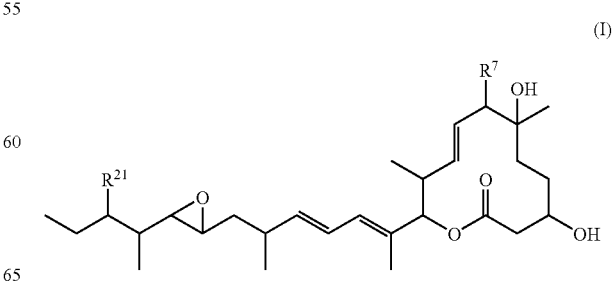

(I)

wherein $R^7$ and $R^{21}$, the same or different, represent 1) a $C_2$ to $C_{22}$ alkoxy group which may have a substituent,
2) an unsaturated $C_2$ to $C_{22}$ alkoxy group which may have a substituent,
3) a $C_7$ to $C_{22}$ aralkyloxy group which may have a substituent,
4) a 5-membered to 14-membered heteroaralkyloxy group which may have a substituent,
5) RC(=Y)—O—, wherein Y represents an oxygen atom or sulfur atom, and R represents
   a) a hydrogen atom,
   b) a $C_2$ to $C_{22}$ alkyl group which may have a substituent,
   c) an unsaturated $C_2$ to $C_{22}$ alkyl group which may have a substituent,
   d) a $C_6$ to $C_{14}$ aryl group which may have a substituent,
   e) a 5-membered to 14-membered heteroaryl group which may have a substituent,
   f) a $C_7$ to $C_{22}$ aralkyl group which may have a substituent,
   g) a 5-membered to 14-membered heteroaralkyl group which may have a substituent,
   h) a $C_1$ to $C_{22}$ alkoxy group which may have a substituent,
   i) an unsaturated $C_2$ to $C_{22}$ alkoxy group which may have a substituent,
   j) a $C_6$ to $C_{14}$ aryloxy group which may have a substituent,
   k) a $C_3$ to $C_{14}$ cycloalkyl group which may have a substituent,
   l) a 3-membered to 14-membered non-aromatic heterocyclic group which may have a substituent or
   m) a 5-membered to 14-membered heteroaryloxy group which may have a substituent,
6) $R^{S1}R^{S2}R^{S3}SiO$—, wherein $R^{S1}$, $R^{S2}$ and $R^{S3}$, the same or different, represent
   a) a $C_1$ to $C_6$ alkyl group or
   b) a $C_6$ to $C_{14}$ aryl group,
7) a halogen atom,
8) $R^{N1}R^{N2}N$—$R^M$—, wherein $R^M$ represents
   a) a single bond,
   b) —CO—O—,
   c) —$SO_2$—O—,
   d) —CS—O— or
   e) —CO—$NR^{N3}$—, wherein $R^{N3}$ represents a hydrogen atom or a $C_1$ to $C_6$ alkyl group which may have a substituent, provided that, the leftmost bond in b) to e) is bonded to the nitrogen atom, and
$R^{N1}$ and $R^{N2}$, the same or different, represent
   a) a hydrogen atom,
   b) a $C_1$ to $C_{22}$ alkyl group which may have a substituent,
   c) an unsaturated $C_2$ to $C_{22}$ alkyl group which may have a substituent,
   d) an aliphatic $C_2$ to $C_{22}$ acyl group which may have a substituent,
   e) an aromatic $C_7$ to $C_{15}$ acyl group which may have a substituent,
   f) a $C_6$ to $C_{14}$ aryl group which may have a substituent,
   g) a 5-membered to 14-membered heteroaryl group which may have a substituent,
   h) a $C_7$ to $C_{22}$ aralkyl group which may have a substituent,
   i) a $C_1$ to $C_{22}$ alkylsulfonyl group which may have a substituent,
   j) a $C_6$ to $C_{14}$ arylsulfonyl group which may have a substituent,
   k) a 3-membered to 14-membered non-aromatic heterocyclic group formed by $R^{N1}$ and $R^{N2}$ together in combination with the nitrogen atom to which $R^{N1}$ and $R^{N2}$ are bonded, wherein the 3-membered to 14-membered non-aromatic heterocyclic group may have a substituent,
   l) a 5-membered to 14-membered heteroaralkyl group which may have a substituent,
   m) a $C_3$ to $C_{14}$ cycloalkyl group which may have a substituent or
   n) a 3-membered to 14-membered non-aromatic heterocyclic group which may have a substituent,
9) $R^{N4}SO_2$—O—, wherein $R^{N4}$ represents
   a) a $C_1$ to $C_{22}$ alkyl group which may have a substituent,
   b) a $C_6$ to $C_{14}$ aryl group which may have a substituent,
   c) a $C_1$ to $C_{22}$ alkoxy group which may have a substituent,
   d) an unsaturated $C_2$ to $C_{22}$ alkoxy group which may have a substituent,
   e) a $C_6$ to $C_{14}$ aryloxy group which may have a substituent,
   f) a 5-membered to 14-membered heteroaryloxy group which may have a substituent,
   g) a $C_7$ to $C_{22}$ aralkyloxy group which may have a substituent or
   h) a 5-membered to 14-membered heteroaralkyloxy group which may have a substituent,
10) $(R^{N5}O)_2PO$—O—, wherein $R^{N5}$ represents
    a) a $C_1$ to $C_{22}$ alkyl group which may have a substituent,
    b) an unsaturated $C_2$ to $C_{22}$ alkyl group which may have a substituent,
    c) a $C_6$ to $C_{14}$ aryl group which may have a substituent,
    d) a 5-membered to 14-membered heteroaryl group which may have a substituent,
    e) a $C_7$ to $C_{22}$ aralkyl group which may have a substituent or
    f) a 5-membered to 14-membered heteroaralkyl group which may have a substituent,
11) $(R^{N1}R^{N2}N)_2PO$—O—, wherein $R^{N1}$ and $R^{N2}$ are the same as defined above or
12) $(R^{N1}R^{N2}N)(R^{N5}O)PO$—O—, wherein $R^{N1}$, $R^{N2}$ and $R^{N5}$ are the same as defined above; or a pharmacologically acceptable salt thereof or a hydrate of those;
2. The compound according to 1. represented by the formula (I-a):

wherein $R^{7a}$ and $R^{21a}$, the same or different, represent
1) a $C_2$ to $C_{22}$ alkoxy group which may have a substituent,
2) an unsaturated $C_2$ to $C_{22}$ alkoxy group which may have a substituent,
3) a $C_7$ to $C_{22}$ aralkyloxy group which may have a substituent,
4) $R^a C(=Y^a)$—O—, wherein $Y^a$ represents an oxygen atom or sulfur atom, and $R^a$ represents
   a) a hydrogen atom,
   b) a $C_2$ to $C_{22}$ alkyl group which may have a substituent,
   c) an unsaturated $C_2$ to $C_{22}$ alkyl group which may have a substituent,
   d) a $C_6$ to $C_{14}$ aryl group which may have a substituent,
   e) a 5-membered to 14-membered heteroaryl group which may have a substituent,
   f) a $C_7$ to $C_{22}$ aralkyl group which may have a substituent,
   g) a 5-membered to 14-membered heteroaralkyl group which may have a substituent,
   h) a $C_1$ to $C_{22}$ alkoxy group which may have a substituent, i) an unsaturated $C_2$ to $C_{22}$ alkoxy group which may have a substituent, j) a $C_6$ to $C_{14}$ aryloxy group which may have a substituent or k) a 3-membered to 14-membered heteroaryloxy group which may have a substituent, 5) $R^{aN1}R^{aN2}N$—CO—O—, wherein $R^{aN1}$ and $R^{aN2}$, the same or different, represent a) a hydrogen atom, b) a $C_1$ to $C_{22}$ alkyl group which may have a substituent, c) an unsaturated $C_2$ to $C_{22}$ alkyl group which may have a substituent, d) a $C_6$ to $C_{14}$ aryl group which may have a substituent, e) a 5-membered to 14-membered heteroaryl group which may have a substituent, f) a $C_7$ to $C_{22}$ aralkyl group which may have a substituent, g) a 3-membered to 14-membered non-aromatic heterocyclic group formed by $R^{aN1}$ and $R^{aN2}$ together in combination with the nitrogen atom to which $R^{aN1}$ and $R^{aN2}$ are bonded, wherein the 3-membered to 14-membered non-aromatic heterocyclic group may have a substituent, h) a 5-membered to 14-membered heteroaralkyl group which may have a substituent, i) a $C_3$ to $C_{14}$ cycloalkyl group which may have a substituent or j) a 3-membered to 14-membered non-aromatic heterocyclic group which may have a substituent, 6) $R^{aN1}R^{aN2}N$—$SO_2$—O—, wherein $R^{aN1}$ and $R^{aN2}$ are the same as defined above, 7) $R^{aN1}R^{aN2}N$—CS—O—, wherein $R^{aN1}$ and $R^{aN2}$ are the same as defined above, 8) $R^{aN4}SO_2$—O—, wherein $R^{aN4}$ represents a) a $C_1$ to $C_{22}$ alkyl group which may have a substituent, b) a $C_6$ to $C_{14}$ aryl group which may have a substituent, c) a $C_1$ to $C_{22}$ alkoxy group which may have a substituent, d) an unsaturated $C_2$ to $C_{22}$ alkoxy group which may have a substituent, e) a $C_6$ to $C_{14}$ aryloxy group which may have a substituent, f) a 5-membered to 14-membered ring heteroaryloxy group which may have a substituent, g) a $C_7$ to $C_{22}$ aralkyloxy group which may have a substituent or h) a 5-membered to 14-membered heteroaralkyloxy group which may have a substituent, 9) $(R^{aN5}O)_2PO$—O—, wherein $R^{aN5}$ represents a) a $C_1$ to $C_{22}$ alkyl group which may have a substituent, b) an unsaturated $C_2$ to $C_{22}$ alkyl group which may have a substituent, c) a $C_6$ to $C_{14}$ aryl group which may have a substituent, d) a 5-membered to 14-membered heteroaryl group which may have a substituent, e) a $C_7$ to $C_{22}$ aralkyl group which may have a substituent or f) a 5-membered to 14-membered heteroaralkyl group which may have a substituent, 10) $(R^{aN1}R^{aN2}N)_2$—PO—O—, wherein $R^{aN1}$ and $R^{aN2}$ are the same as defined above or 11) $(R^{aN1}R^{aN2}N)(R^{aN5}O)PO$—O—, wherein $R^{aN1}$, $R^{aN2}$ and $R^{aN5}$ are the same as defined above; or a pharmacologically acceptable salt thereof or a hydrate of those;

3. The compound according to 1., wherein $R^7$ and/or $R^{21}$ represent a $C_7$ to $C_{22}$ aralkyloxy group which may have a substituent, RC(=Y)—O—, wherein Y and R are the same as defined above or $R^{N1}R^{N2}N$—$R^M$—, wherein $R^M$ represents a) —CO—O— or b) —CS—O—, and $R^{N1}$ and $R^{N2}$ are the same as defined above, provided that, the leftmost bond in a) and b) is bonded to the nitrogen atom; or a pharmacologically acceptable salt thereof or a hydrate of those;

4. The compound according to 1., wherein $R^{N1}$ and $R^{N2}$, the same or different, represent a $C_1$ to $C_6$ alkyl group or $C_6$ to $C_{14}$ aryl group or form, together in combination with the nitrogen atom to which $R^{N1}$ and $R^{N2}$ are bonded, a non-aromatic heterocyclic group selected from the group consisting of:

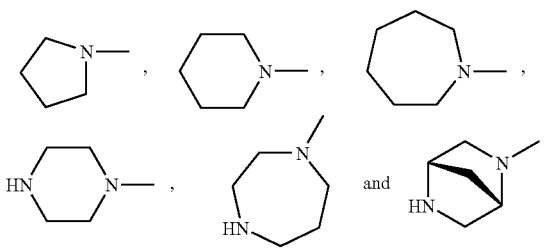

a pharmacologically acceptable salt thereof or a hydrate of those;

5. The compound according to 2. represented by the formula (I-b):

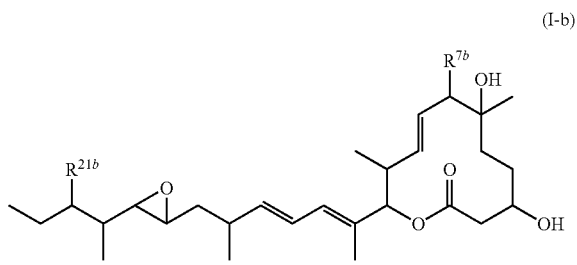

wherein $R^{7b}$ and $R^{21b}$, the same or different, represent a $C_7$ to $C_{22}$ aralkyloxy group which may have a substituent or $R^b$—C(=$Y^b$)—O—, wherein $Y^b$ represents an oxygen atom or sulfur atom, and $R^b$, the same or different, represents a) a hydrogen atom, b) a $C_2$ to $C_6$ alkyl group which may have a substituent, c) a $C_6$ to $C_{14}$ aryl group which may have a substituent, d) a 5-membered to 14-membered heteroaryl group which may have a substituent, e) a $C_7$ to $C_{10}$ aralkyl group which may have a substituent, f) a 5-membered to 14-membered heteroaralkyl group which may have a substituent, g) a 3-membered to 14-membered non-aromatic heterocyclic group which may have a substituent, h) a group of the formula (III):

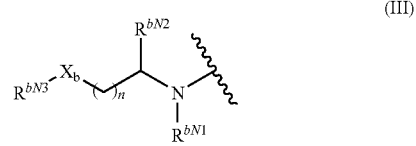

wherein A) n represents an integer of 0 to 4,
$X_b$ represents
  i) —CHR$^{bN4}$—,
  ii) —NR$^{bN5}$—,
  iii) —O—,
  iv) —S—,
  v) —SO— or
  vi) —SO$_2$—,
$R^{bN1}$ represents
  i) a hydrogen atom or
  ii) a $C_1$ to $C_6$ alkyl group which may have a substituent,
$R^{bN2}$ represents
  i) a hydrogen atom or
  ii) a $C_1$ to $C_6$ alkyl group which may have a substituent,
$R^{bN3}$ and $R^{bN4}$, the same or different, represent
  i) a hydrogen atom,
  ii) a $C_1$ to $C_6$ alkyl group which may have a substituent,
  iii) an unsaturated $C_2$ to $C_{10}$ alkyl group which may have a substituent,
  iv) a $C_6$ to $C_{14}$ aryl group which may have a substituent,
  v) a 5-membered to 14-membered heteroaryl group which may have a substituent,
  vi) a $C_7$ to $C_{10}$ aralkyl group which may have a substituent,
  vii) a $C_3$ to $C_8$ cycloalkyl group which may have a substituent,
  viii) a $C_4$ to $C_9$ cycloalkylalkyl group which may have a substituent,
  ix) a 5-membered to 14-membered heteroaralkyl group which may have a substituent,
  x) a 5-membered to 14-membered non-aromatic heterocyclic group which may have a substituent,
  xi) —NR$^{bN6}$R$^{bN7}$, wherein $R^{bN6}$ and $R^{bN7}$, the same or different, represent a hydrogen atom or a $C_1$ to $C_6$ alkyl group which may have a substituent or
  xii) a 5-membered to 14-membered non-aromatic heterocyclic group formed by $R^{bN3}$ and $R^{bN4}$ together in combination with the carbon atom to which $R^{bN3}$ and $R^{bN4}$ are bonded, wherein the 5-membered to 14-membered non-aromatic heterocyclic group may have a substituent, and
$R^{bN5}$ represents
  i) a hydrogen atom,
  ii) a $C_1$ to $C_6$ alkyl group which may have a substituent,
  iii) an unsaturated $C_2$ to $C_{10}$ alkyl group which may have a substituent,
  iv) a $C_6$ to $C_{14}$ aryl group which may have a substituent,
  v) a 5-membered to 14-membered heteroaryl group which may have a substituent,
  vi) a $C_7$ to $C_{10}$ aralkyl group which may have a substituent,
  vii) a $C_3$ to $C_8$ cycloalkyl group which may have a substituent,
  viii) a $C_4$ to $C_9$ cycloalkylalkyl group which may have a substituent,
  ix) a 5-membered to 14-membered heteroaralkyl group which may have a substituent,
  x) a 5-membered to 14-membered non-aromatic heterocyclic group which may have a substituent or
  xi) a 5-membered to 14-membered non-aromatic heterocyclic group formed by $R^{bN3}$ and $R^{bN5}$ together in combination with the nitrogen atom to which $R^{bN3}$ and $R^{bN5}$ are bonded, wherein the 5-membered to 14-membered non-aromatic heterocyclic group may have a substituent,
B)
  $X_b$, n, $R^{bN3}$, $R^{bN}$ and $R^{bN5}$ represent the same group as defined above, and $R^{bN1}$ and $R^{bN2}$ represent a 5-membered to 14-membered non-aromatic heterocyclic group formed by $R^{bN1}$ and $R^{bN2}$ together, wherein the 5-membered to 14-membered non-aromatic heterocyclic group may have a substituent,
C)
  $X_b$, n, $R^{bN2}$, $R^{bN4}$ and $R^{bNn5}$ represent the same group as defined above, and $R^{bN1}$ and $R^{bN3}$ represent a 5-membered to 14-membered non-aromatic heterocyclic group formed by $R^{bN1}$ and $R^{bN3}$ together, wherein the 5-membered to 14-membered non-aromatic heterocyclic group may have a substituent or
D)
  $X_b$, n, $R^{bN1}$, $R^{bN4}$ and $R^{bN5}$ represent the same group as defined above, and $R^{bN2}$ and $R^{bN3}$ represent a 5-membered to 14-membered g non-aromatic heterocyclic group formed by $R^{bN2}$ and $R^{bN3}$ together, wherein the 5-membered to 14-membered non-aromatic heterocyclic group may have a substituent or
  i) a group of the formula (IV):

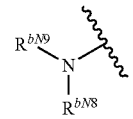

(IV)

wherein $R^{bN8}$ and $R^{bN9}$, the same or different, represent
  i) a hydrogen atom,
  ii) a $C_1$ to $C_6$ alkyl group which may have a substituent,
  iii) a $C_6$ to $C_{14}$ aryl group which may have a substituent,
  iv) a 5-membered to 14-membered heteroaryl group which may have a substituent,
  v) a $C_7$ to $C_{10}$ aralkyl group which may have a substituent or
  vi) a 5-membered to 14-membered heteroaralkyl group which may have a substituent; or a pharmacologically acceptable salt thereof or a hydrate of those;

6. The compound according to 2., wherein $R^{7a}$ and/or $R^{21a}$ represent $R^{a1}C(=Y^{a1})$—O—, wherein $Y^{a1}$ represents an oxygen atom or sulfur atom, and $R^{a1}$ represents
  1) a hydrogen atom,
  2) a $C_2$ to $C_6$ alkyl group which may have a substituent,
  3) a $C_6$ to $C_{10}$ aryl group which may have a substituent,
  4) a 5-membered to 14-membered heteroaryl group which may have a substituent,
  5) a $C_7$ to $C_{10}$ aralkyl group which may have a substituent or
  6) a 5-membered to 14-membered heteroaralkyl group which may have a substituent; or a pharmacologically acceptable salt thereof or a hydrate of those;

7. The compound according to 2., wherein $R^{7a}$ and/or $R^{21a}$ represent $R^{a2}C(=Y^{a2})$—O—, wherein $Y^{a2}$ represents an oxygen atom or sulfur atom, and $R^{a2}$ represents a group of the formula (III'):

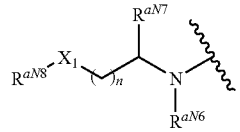

(III')

wherein A) n represents an integer of 0 to 4,
$X^1$ represents
  1) —CHR$^{aN9}$—,
  2) —NR$^{aN10}$—, 3) —O—,
4) —S—,
5) —SO— or
6) —SO$_2$—, $R^{aN6}$ and $R^{aN7}$, the same or different, represent
  1) a hydrogen atom or
  2) a $C_1$ to $C_6$ alkyl group which may have a substituent, $R^{aN8}$ and $R^{aN9}$, the same or different, represent
  1) a hydrogen atom,
  2) a $C_1$ to $C_6$ alkyl group which may have a substituent,
  3) an unsaturated $C_2$ to $C_{10}$ alkyl group which may have a substituent,
  4) a $C_6$ to $C_{14}$ aryl group which may have a substituent,
  5) a 5-membered to 14-membered heteroaryl group which may have a substituent,
  6) a $C_7$ to $C_{10}$ aralkyl group which may have a substituent,
  7) a $C_3$ to $C_8$ cycloalkyl group which may have a substituent,
  8) a $C_4$ to $C_9$ cycloalkylalkyl group which may have a substituent,
  9) a 5-membered to 14-membered heteroaralkyl group which may have a substituent,
  10) a 5-membered to 14-membered non-aromatic heterocyclic group which may have a substituent,
  11) —NR$^{aN11}$R$^{aN12}$, wherein R$^{aN11}$ and R$^{aN12}$, the same or different, represent a hydrogen atom or a $C_1$ to $C_6$ alkyl group which may have a substituent or
  12) a 5-membered to 14-membered non-aromatic heterocyclic group formed by $R^{aN8}$ and $R^{aN9}$ together, wherein the 5-membered to 14-membered non-aromatic heterocyclic group may have a substituent, and $R^{aN10}$ represents
  1) a hydrogen atom,
  2) a $C_1$ to $C_6$ alkyl group which may have a substituent,
  3) an unsaturated $C_2$ to $C_{10}$ alkyl group which may have a substituent,
  4) a $C_6$ to $C_{14}$ aryl group which may have a substituent,
  5) a 5-membered to 14-membered heteroaryl group which may have a substituent,
  6) a $C_7$ to $C_{10}$ aralkyl group which may have a substituent,
  7) a $C_3$ to $C_8$ cycloalkyl group which may have a substituent,
  8) a $C_4$ to $C_9$ cycloalkylalkyl group which may have a substituent,
  9) a 5-membered to 14-membered heteroaralkyl group which may have a substituent,
  10) a 5-membered to 14-membered non-aromatic heterocyclic group which may have a substituent,
  11) a 5-membered to 14-membered non-aromatic heterocyclic group formed by the nitrogen atom to which $R^{aN10}$ is bonded, and one substituent selected from the group consisting of $R^{aN6}$, $R^{aN7}$ and $R^{aN8}$ together, wherein the 5-membered to 14-membered ring non-aromatic heterocyclic group may have a substituent or
  12) a 5-membered to 14-membered non-aromatic heterocyclic group formed by the nitrogen atom to which $R^{aN10}$ is bonded, and two substituents selected from the group consisting of $R^{aN6}$, $R^{aN7}$ and $R^{aN8}$ together, wherein the 5-membered to 14-membered non-aromatic heterocyclic group may have a substituent or B) n, $X_1$, $R^{aN7}$, $R^{aN9}$ and $R^{aN10}$ represent the same group as defined above, and $R^{aN6}$ and $R^{aN8}$ represent a 5-membered to 14-membered non-aromatic heterocyclic group formed by $R^{aN6}$ and $R^{aN8}$ together, wherein the 5-membered to 14-membered non-aromatic heterocyclic group may have a substituent; or a pharmacologically acceptable salt thereof or a hydrate of those;

8. The compound according to 6., wherein $X_1$ represents —NR$^{aN10}$—, wherein NR$^{aN10}$ is the same as defined above; or a pharmacologically acceptable salt thereof or a hydrate of those;

9. The compound according to 2., wherein $R^{7a}$ and/or $R^{21a}$ represent $R^{a3}$C(=Y$^{a3}$)—O—, wherein Y$^{a3}$ represents an oxygen atom or sulfur atom, and $R^{a3}$ represents a group of the formula (V):

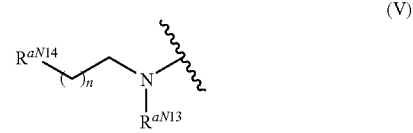

(V)

wherein n represents an integer of 0 to 4, $R^{aN13}$ represents
  1) a hydrogen atom or
  2) a $C_1$ to $C_6$ alkyl group which may have a substituent (for example, a methyl group, ethyl group or the like), and $R^{aN14}$ represents
  1) a hydrogen atom,
  2) an amino group which may have a substituent (for example, a methylamino group, dimethylamino group, ethylamino group, diethylamino group, ethylmethylamino group or the like),
  3) a pyridinyl group which may have a substituent,
  4) a pyrrolidin-1-yl group which may have a substituent,
  5) a piperidin-1-yl group which may have a substituent,
  6) a morpholin-4-yl group which may have a substituent or
  7) a piperazin-1-yl group which may have a substituent (for example, a 4-methylpyperazin-yl group or the like); or a pharmacologically acceptable salt thereof or a hydrate of those;

10. The compound according to 2., wherein $R^{7a}$ and/or $R^{21a}$ represent $R^{a4}$CO—O—, wherein $R^{a4}$ represents a group of the formula (VI):

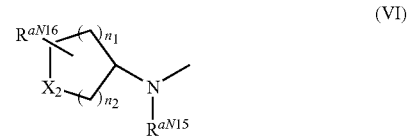

(VI)

wherein $n_1$ and $n_2$, the same or different, represent an integer of 0 to 4, $X_2$ represents
  1) —CHR$^{aN17}$—,
  2) —NR$^{aN18}$—,
  3) —O—,
  4) —S—,
  5) —SO— or
  6) —SO$_2$—, $R^{aN15}$ represents
  1) a hydrogen atom or
  2) a $C_1$ to $C_6$ alkyl group which may have a substituent, $R^{aN16}$ represents
  1) a hydrogen atom,
  2) a $C_1$ to $C_6$ alkyl group which may have a substituent,
  3) a $C_6$ to $C_{14}$ aryl group which may have a substituent or
  4) a $C_7$ to $C_{10}$ aralkyl group which may have a substituent, $R^{aN17}$ represents
  1) a hydrogen atom,
  2) a $C_1$ to $C_6$ alkyl group which may have a substituent, 3) an unsaturated $C_2$ to $C_{10}$ alkyl group which may have a substituent, 4) a $C_6$ to $C_{14}$ aryl group which may have a substituent, 5) a 5-membered to 14-membered heteroaryl group which may have a substituent, 6) a $C_7$ to $C_{10}$ aralkyl group which may have a substituent, 7) a $C_3$ to $C_8$ cycloalkyl group which may have a substituent, 8) a $C_4$ to $C_9$ cycloalkylalkyl group which may have a substituent, 9) a 5-membered to 14-membered heteroaralkyl group which may have a substituent, 10) —$NR^{aN19}R^{aN20}$, wherein $R^{aN19}$ and $R^{aN20}$, the same or different, represent a hydrogen atom or a $C_1$ to $C_6$ alkyl group which may have a substituent or 11) a 5-membered to 14-membered non-aromatic heterocyclic group which may have a substituent, and $R^{aN18}$ represents 1) a hydrogen atom, 2) a $C_1$ to $C_6$ alkyl group which may have a substituent, 3) an unsaturated $C_2$ to $C_{10}$ alkyl group which may have a substituent, 4) a $C_6$ to $C_{14}$ aryl group which may have a substituent, 5) a 5-membered to 14-membered heteroaryl group which may have a substituent, 6) a $C_7$ to $C_{10}$ aralkyl group which may have a substituent, 7) a $C_3$ to $C_8$ cycloalkyl group which may have a substituent, 8) a $C_4$ to $C_9$ cycloalkylalkyl group which may have a substituent, 9) a 5-membered to 14-membered heteroaralkyl group which may have a substituent or 10) a 5-membered to 14-membered non-aromatic heterocyclic group which may have a substituent; or a pharmacologically acceptable salt thereof or a hydrate of those;

11. The compound according to 2., wherein $R^{7a}$ and/or $R^{21a}$ represent $R^{a5}CO—O—$, wherein $R^{a5}$ represents a group of the formula (VII):

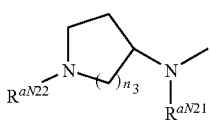

(VII)

wherein $n_3$ represents 1 or 2, $R^{aN21}$ represents 1) a hydrogen atom or 2) a $C_1$ to $C_6$ alkyl group which may have a substituent (for example, a methyl group, ethyl group or the like), and $R^{aN22}$ represents 1) a hydrogen atom or 2) a $C_1$ to $C_6$ alkyl group which may have a substituent (for example, a methyl group, ethyl group or the like); or a pharmacologically acceptable salt thereof or a hydrate of those;

12. The compound according to 2., wherein $R^{7a}$ and/or $R^{21a}$ represent $R^{a6}CO—O—$, wherein $R^{a6}$ represents a group of the formula (VIII):

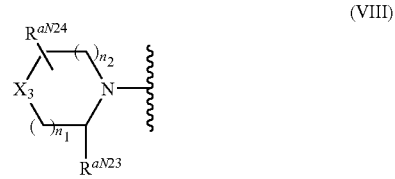

(VIII)

wherein $n_1$ and $n_2$, the same or different, represent an integer of 0 to 4, $X_3$ represents 1) —$CHR^{aN25}$—m 2) —$NR^{aN25}$—,

3) —O—,

4) —S—,

5) —SO— or

6) —$SO_2$—, $R^{aN23}$ represents 1) a hydrogen atom or 2) a $C_1$ to $C_6$ alkyl group which may have a substituent, $R^{aN24}$ represents 1) a hydrogen atom, 2) a $C_1$ to $C_6$ alkyl group which may have a substituent, 3) a $C_6$ to $C_{14}$ aryl group which may have a substituent or 4) a $C_7$ to $C_{10}$ aralkyl group which may have a substituent, $R^{aN25}$ represents 1) a hydrogen atom, 2) a $C_1$ to $C_6$ alkyl group which may have a substituent, 3) an unsaturated $C_2$ to $C_{10}$ alkyl group which may have a substituent, 4) a $C_1$ to $C_6$ alkoxy group which may have a substituent, 5) a $C_6$ to $C_{14}$ aryl group which may have a substituent, 6) a 5-membered to 14-membered heteroaryl group which may have a substituent, 7) a $C_7$ to $C_{10}$ aralkyl group which may have a substituent, 8) a $C_3$ to $C_8$ cycloalkyl group which may have a substituent, 9) a $C_4$ to $C_9$ cycloalkylalkyl group which may have a substituent, 10) a 5-membered to 14-membered heteroaralkyl group which may have a substituent, 11) $NR^{aN27}R^{aN28}$, wherein $R^{aN27}$ and $R^{aN28}$, the same or different, represent a hydrogen atom or a $C_1$ to $C_6$ alkyl group which may have a substituent or 12) a 5-membered to 14-membered non-aromatic heterocyclic group which may have a substituent, and $R^{aN26}$ represents 1) a hydrogen atom, 2) a $C_1$ to $C_6$ alkyl group which may have a substituent, 3) an unsaturated $C_2$ to $C_{10}$ alkyl group which may have a substituent, 4) a $C_6$ to $C_{14}$ aryl group which may have a substituent, 5) a 5-membered to 14-membered heteroaryl group which may have a substituent, 6) a $C_7$ to $C_{10}$ aralkyl group which may have a substituent, 7) a $C_3$ to $C_8$ cycloalkyl group which may have a substituent, 8) a $C_4$ to $C_9$ cycloalkylalkyl group which may have a substituent, 9) a 5-membered to 14-membered heteroaralkyl group which may have a substituent or 10) a 5-membered to 14-membered non-aromatic heterocyclic group which may have a substituent; or a pharmacologically acceptable salt thereof or a hydrate of those;

13. The compound according to 2., wherein $R^{7a}$ and/or $R^{21a}$ represent $R^{a7}CO-O-$, wherein $R^{a7}$ represents a group of the formula (IX):

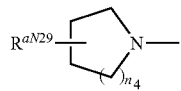
(IX)

wherein $n_4$ represents an integer of 1 to 3, and $R^{aN29}$ represents
1) an amino group which may have a substituent (for example, a methylamino group, dimethylamino group or the like),
2) a pyrrolidin-1-yl group which may have a substituent,
3) a piperidin-1-yl group which may have a substituent or
4) a morpholin-4-yl group which may have a substituent; or a pharmacologically acceptable salt thereof or a hydrate of those;

14. The compound according to 2., wherein $R^{7a}$ and/or $R^{21a}$ represent $R^{a8}CO-O-$, wherein $R^{a8}$ represents a group of the formula (X):

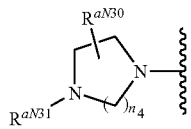
(X)

wherein $n_4$ represents an integer of 1 to 3, $R^{aN30}$ represents
1) a hydrogen atom,
2) a $C_1$ to $C_6$ alkyl group which may have a substituent,
3) a $C_6$ to $C_{14}$ aryl group which may have a substituent or
4) a $C_7$ to $C_{10}$ aralkyl group which may have a substituent, and
$R^{aN31}$ represents
1) a hydrogen atom,
2) a $C_1$ to $C_6$ alkyl group which may have a substituent,
3) a $C_3$ to $C_8$ cycloalkyl group which may have a substituent,
4) a 3-membered to 8-membered non-aromatic heterocyclic group which may have a substituent,
5) a $C_6$ to $C_{14}$ aryl group which may have a substituent,
6) a 5-membered to 14-membered heteroaryl group which may have a substituent,
7) a $C_7$ to $C_{10}$ aralkyl group which may have a substituent,
8) a 5-membered to 14-membered heteroaralkyl group which may have a substituent or
9) a $C_4$ to $C_9$ cycloalkylalkyl group which may have a substituent; or a pharmacologically acceptable salt thereof or a hydrate of those;

15. The compound according to 2., wherein $R^{7a}$ and/or $R^{21a}$ represent $R^{a9}CO-O-$, wherein $R^{a9}$ represents a group of the formula (XI):

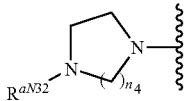
(XI)

wherein $n_4$ represents an integer of 1 to 3, and $R^{aN32}$ represents
1) a hydrogen atom,
2) a $C_1$ to $C_6$ alkyl group which may have a substituent,
3) a $C_3$ to $C_8$ cycloalkyl group which may have a substituent,
4) a $C_4$ to $C_9$ cycloalkylalkyl group which may have a substituent,
5) a $C_7$ to $C_{10}$ aralkyl group which may have a substituent,
6) a pyridyl group which may have a substituent or
7) a tetrahydropyranyl group which may have a substituent; or a pharmacologically acceptable salt thereof or a hydrate of those;

16. The compound according to 2., wherein $R^{7a}$ and/or $R^{21a}$ represent $R^{a10}CO-O-$, wherein $R^{a10}$ represents a group of the formula (XII):

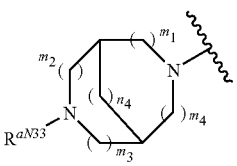
(XII)

wherein $m_1$, $m_2$, $m_3$ and $m_4$, the same or differently, represent 0 or 1,
$n_4$ represents an integer of 1 to 3, and
$R^{aN33}$ represents
1) a hydrogen atom,
2) a $C_1$ to $C_6$ alkyl group which may have a substituent,
3) an unsaturated $C_2$ to $C_{10}$ alkyl group which may have a substituent,
4) a $C_6$ to $C_{14}$ aryl group which may have a substituent,
5) a 5-membered to 14-membered heteroaryl group which may have a substituent,
6) a $C_7$ to $C_{10}$ aralkyl group which may have a substituent,
7) a $C_3$ to $C_8$ cycloalkyl group which may have a substituent,
8) a $C_4$ to $C_9$ cycloalkylalkyl group which may have a substituent,
9) a 5-membered to 14-membered heteroaralkyl group which may have a substituent or
10) a 5-membered to 14-membered non-aromatic heterocyclic group which may have a substituent; or a pharmacologically acceptable salt thereof or a hydrate of those;

17. The compound according to 2., wherein $R^{7a}$ and/or $R^{21a}$ represent $R^{a11}CO-O-$, wherein $R^{a11}$ represents a group of the formula (XIII):

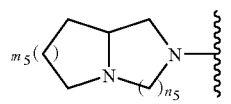
(XIII)

wherein $m_5$ represents an integer of 1 to 3, and $n_5$ represents 2 or 3; or a pharmacologically acceptable salt thereof or a hydrate of those;

18. The compound according to claim 2, wherein $R^{7a}$ and/or $R^{21a}$ represent $R^{a12}CO-O-$, wherein $R^{a12}$ represents a group selected from a group consisting of:

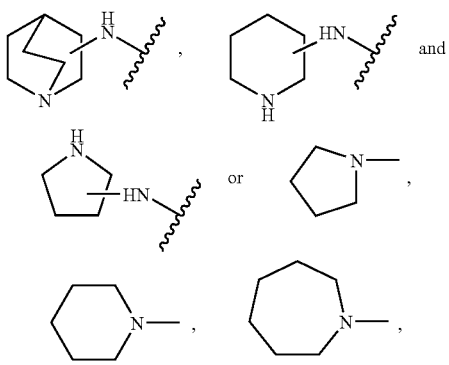

or a group selected from a group consisting of

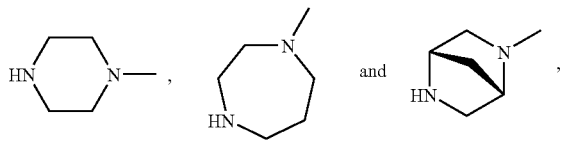

and both of which may have a substituent on the ring; or a pharmacologically acceptable salt thereof or a hydrate of those;

19. The compound according to 1., which is (8E,12E,14E)-21-benzoyloxy-3,6-dihydroxy-6,10,12,16,20-pentamethyl-7-((4-methylpiperazin-1-yl)carbonyl)oxy-18,19-epoxytricosa-8,12,14-trien-11-olide, (8E,12E,14E)-21-(N,N-dimethylcarbamoyloxy)-3,6-dihydroxy-6,10,12,16,20-pentamethyl-7-((4-methylpiperazin-1-yl)carbonyl)oxy-18,19-epoxytricosa-8,12,14-trien-11-olide and (8E,12E,14E)-3,6-dihydroxy-6,10,12,16,20-pentamethyl-7-((4-methylpiperazin-1-yl)carbonyl)oxy-21-(N-phenylcarbamoyloxy)-18,19-epoxytricosa-8,12,14-trien-11-olide; or a pharmacologically acceptable salt thereof or a hydrate of those;

20. A medicine comprising the compound according to any one of 1. to 19. or a pharmacologically acceptable salt thereof or a hydrate of those as an active ingredient;
21. A pharmaceutical composition comprising the compound according to any one of 1. to 19. or a pharmacologically acceptable salt thereof or a hydrate of those as an active ingredient;
22. The medicine according to 20. as an agent for preventing or treating a disease for which gene expression control is effective;
23. The medicine according to 20. as an agent for preventing or treating a disease for which suppression of VEGF production is effective;
24. The medicine according to 20. as an agent for preventing or treating a disease for which an antiangiogenic effect is effective;
25. The medicine according to 20. as an angiogenesis inhibitor;
26. The medicine according to 20. as an antitumor agent;
27. The medicine according to 20. as a therapeutic agent for treating hemangioma;
28. The medicine according to 20. as a cancer metastasis inhibitor;
29. The medicine according to 20. as a therapeutic agent for treating retinal neovascularization or diabetic retinopathy;
30. The medicine according to 20. as a therapeutic agent for treating inflammatory disease;
31. The medicine according to 20. as a therapeutic agent for treating inflammatory diseases consisting of deforamantarthritis, rheumatoid arthritis, psoriasis and delayed hypersensitive reaction;
32. The medicine according to 20. as a therapeutic agent for treating atherosclerosis;
33. The medicine according to 20. as a therapeutic agent for treating a solid cancer;
34. The medicine according to 33., wherein the solid cancer is lung cancer, brain tumor, breast cancer, prostate cancer, ovarian cancer, colon cancer or melanoma;
35. The medicine according to 20. as a therapeutic agent for treating leukemia;
36. The medicine according to 20. as an antitumor agent based on gene expression control;
37. The medicine according to 20. as an antitumor agent based on VEGF suppression of production;
38. The medicine according to 20. as an antitumor agent based on an effect of angiogenesis inhibition;
39. A method for preventing or treating a disease for which gene expression control is effective, comprising administering a pharmacologically effective dose of the medicine according to 20. to a patient;
40. A method for preventing or treating a disease for which suppression of VEGF production is effective, comprising administering a pharmacologically effective dose of the medicine according to 20. to a patient;
41. A method for preventing or treating a disease for which angiogenesis inhibition is effective, comprising administering a pharmacologically effective dose of the medicine according to 20. to a patient;
42. Use of the compound according to any one of 1. to 19. or a pharmacologically acceptable salt thereof or a hydrate of those, for manufacturing an agent for preventing or treating a disease for which gene expression control is effective;
43. Use of the compound according to any one of 1. to 19. or a pharmacologically acceptable salt thereof or a hydrate of those, for manufacturing an agent for preventing or treating a disease for which suppression of VEGF production is effective;
44. Use of the compound according to any one of 1. to 19. or a pharmacologically acceptable salt thereof or a hydrate of those, for manufacturing an agent for preventing or treating a disease for which angiogenesis inhibition is effective; and
45. Use of the compound according to any one of 1. to 19. or a pharmacologically acceptable salt thereof or a hydrate of those, for manufacturing an agent for preventing or treating a solid cancer.

BEST MODE FOR CARRYING OUT THE INVENTION

Various terms, symbols, and the like described in the present specification will be described below.

In the present specification, a chemical formula of the compound of the present invention is illustrated as a plan chemical formula for convenience. However, the present invention can include given isomers derived from the chemical formula. The present invention can include all isomers and mixtures of such as geometric isomers which are generated from the configuration of the compound, optical isomers based on symmetric carbon, rotamers, stereoisomers, and tautomers, and mixtures of these isomers. The present invention is not limited to the expediential description of a chemical formula, and can include any one of the above-described isomers or mixtures thereof. Accordingly, the compound of the present invention exists as an optically active substance or racemate when the compound has an asymmetric carbon atom in the molecule, and both the optically active substance and the racemate are included in the present invention. Although crystal polymorphs of the compound may be present, the component is not limited to only one crystal form and may be present as a single crystal form or a mixture of multiple crystal forms. The compound of the formula (I) of the present invention or its salt may be an anhydrate or hydrate. Both an anhydrate and a hydrate are included in the present invention. A metabolite resulting from decomposing the compound of the formula (I) of the present invention in vivo, and a prodrug of the compound of the formula (I) of the present invention or its salt are included in the present invention.

The "halogen atom" used in the specification of the present application refers to a fluorine atom, chlorine atom, bromine atom and iodine atom. For example, a fluorine atom, chlorine atom and bromine atom are preferable. Of these, for example, a fluorine atom and chlorine atom are typically preferable.

The "$C_1$ to $C_{22}$ alkyl group/$C_2$ to $C_{22}$ alkyl group" used in the specification of the present application refers to a linear or branched alkyl group having 1 to 22 carbon atoms/2 to 22 carbon atoms. Examples include a methyl group (excluded in the case of $C_2$ to $C_{22}$ alkyl group), ethyl group, n-propyl group, iso-propyl group, n-butyl group, iso-butyl group, sec-butyl group, tert-butyl group, n-pentyl group, 1,1-dimethylpropyl group, 1,2-dimethylpropyl group, 2,2-dimethylpropyl group, 1-ethylpropyl group, n-hexyl group, 1-ethyl-2-methylpropyl group, 1,1,2-trimethylpropyl group, 1-ethylbutyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group, 3-methylpentyl group, n-heptyl group, n-octyl group, n-nonyl group and n-decyl group. Such a group preferably refers to a linear or branched alkyl group having 1 to 6 carbon atoms ($C_1$ to $C_6$ alkyl group)/a linear or branched alkyl group having 2 to 6 carbon atoms ($C_2$ to $C_6$ alkyl group) Examples include a methyl group (excluded in the case of $C_2$ to $C_6$ alkyl group), ethyl group, n-propyl group, iso-propyl group, n-butyl group, iso-butyl group, sec-butyl group, tert-butyl group and n-pentyl group. Of these, for example, a methyl group, ethyl group, propyl group, iso-propyl group, n-butyl group, iso-butyl group and tert-butyl group are preferable.

The "unsaturated $C_2$ to $C_{22}$ alkyl group" used in the specification of the present application refers to a linear or branched alkenyl group having 2 to 22 carbon atoms or a linear or branched alkynyl group having 2 to 22 carbon atoms. Examples include a vinyl group, allyl group, 1-propenyl group, isopropenyl group, 2-methyl-1-propenyl group, 2-methyl-2-propenyl group, 1-butenyl group, 2-butenyl group, 3-butenyl group, 1-pentenyl group, 1-hexenyl group, 1,3-hexanedienyl group, 1,5-hexanedienyl group, ethynyl group, 1-propynyl group, 2-propynyl group, 1-butynyl group, 2-butynyl group, 3-butynyl group, 1-ethynyl-2-propynyl group, 2-methyl-3-butynyl group, 1-pentynyl group, 1-hexynyl group, 1,3-hexanediynyl group and 1,5-hexanediynyl group. Such a group preferably refers to a linear or branched alkenyl group having 2 to 10 carbon atoms or a linear or branched alkynyl group having 2 to 10 carbon atoms. Examples include a vinyl group, allyl group, 1-propenyl group, isopropenyl group, 3-methyl-2-butenyl group, 3,7-dimethyl-2,6-octadienyl group, ethynyl group, 1-propynyl group, 2-propynyl group, 1-butynyl group, 2-butynyl group, 3-butynyl group and 3-methyl-1-propynyl group.

The "$C_6$ to $C_{14}$ aryl group" used in the specification of the present application refers to an aromatic hydrocarbon group comprising 6 to 14 carbon atoms, and includes a monocyclic group and condensed ring such as a bicyclic group or tricyclic group. Examples include a phenyl group, indenyl group, 1-naphthyl group, 2-naphthyl group, azulenyl group heptalenyl group, indacenyl group, acenaphthyl group, fluorenyl group, phenalenyl group, phenanthrenyl group and anthracenyl group. For example, a phenyl group, 1-naphthyl group and 2-naphthyl group are preferable.

The "5-membered to 14-membered heteroaryl group" in the specification of the present application refers to a monocyclic, bicyclic or tricyclic 5-membered to 14-membered aromatic heterocyclic group containing one or more hetero atoms selected from the group consisting of a nitrogen atom, sulfur atom and oxygen atom. Preferable examples include nitrogen-containing aromatic heterocyclic groups such as a pyrrolyl group, pyridinyl group, pyridazinyl group, pyrimidinyl group, pyrazininyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, quinolyl group, isoquinolinyl group, quinolizinyl group, phthalazinyl group, naphthylidinyl group, quinoxalinyl group, quinazolinyl group, cinnolinyl group, pteridinyl group, imidazotriazinyl group, pyrazinopyridazinyl group, acridinyl group, phenanthridinyl group, carbazolyl group, carbazolinyl group, perimidinyl group, phenanthrolinyl group, phenazinyl group, imidazopyridinyl group, imidazopyrimidinyl group, pyrazolopyridinyl group and pyrazolopyridinyl group; sulfur-containing aromatic heterocyclic groups such as a thienyl group and benzothienyl group; oxygen-containing aromatic heterocyclic groups such as a furyl group, pyranyl group, cyclopentapyranyl group, benzofuryl group and isobenzofuryl group; and aromatic heterocyclic groups containing two or more different hetero atoms such as a thiazolyl group, isothiazolyl group, benzothiazolyl group, benzothiadiazolyl group, phenothiazinyl group, isoxazolyl group, furazanyl group, phenoxazinyl group, oxazolyl group, isoxazoyl group, benzoxazolyl group, oxadiazolyl group, pyrazolooxazolyl group, imidazothiazolyl group, thienofuranyl group, furopyrrolyl group and pyridoxazinyl group. For example, a thienyl group, furyl group, pyridinyl group, pyridazinyl group, pyrimidinyl group and pyrazinyl group are preferable.

The "3(5)-membered to 14-membered non-aromatic heterocyclic group" in the specification of the present application refers to a monocyclic, bicyclic or tricyclic 3(5)-membered to 14-membered non-aromatic heterocyclic group, which may contain one or more hetero atoms selected from the group consisting of a nitrogen atom, sulfur atom and oxygen atom. Preferable examples include an aziridinyl group (excluded in the case of 5-membered to 14-membered non-aromatic heterocyclic group), azetidyl group (excluded in the case of 5-membered to 14-membered non-aromatic heterocyclic group), pyrrolidinyl group, pyrrolyl group, piperidinyl group, piperazinyl group, homopiperidinyl group, homopiperazinyl group, imidazolyl group, pyrazolidinyl group, imidazolidinyl group, morpholinyl group, thiomorpholinyl group, imidazolinyl group, oxazolinyl group, 2,5-diazabicyclo[2.2.1]heptyl group, 2,5-diazabicyclo[2.2.2]octyl group, 3,8-diazabicyclo[3.2.1]octyl group, 1,4-diazabicyclo[4.3.0]nonyl group, quinuclidinyl group, tetrahydrofuranyl group and tetrahydrothiophenyl group. The above-described non-aromatic heterocyclic groups include a group derived from a pyridone ring, and a non-aromatic condensed ring (for example, a group derived from a phthalimide ring, succinimide ring or the like).

The "$C_7$ to $C_{22}$ aralkyl group" used in the specification of the present application refers to a group of the above-defined "$C_1$ to $C_{22}$ alkyl group" on which the above-defined "$C_6$ to $C_{14}$ aryl group" is substituted as a substituent for replaceable moiety thereof. Specific examples include a benzyl group, phenethyl group, 3-phenylpropyl group, 4-phenylbutyl group, 1-naphthylmethyl group and 2-naphthylmethyl group. An aralkyl group having 7 to 10 carbon atoms, for example, a benzyl group or phenethyl group, is preferable.

The "5-membered to 14-membered heteroaralkyl group" used in the specification of the present application refers a group of the above-defined "$C_1$ to $C_{22}$ alkyl group" having the above-defined "5-membered to 14-membered heteroaryl group" as a substituent. Specific examples include a thienylmethyl group, furylmethyl group, pyridinylmethyl group, pyridazinylmethyl group, pyrimidinylmethyl group and pyrazinylmethyl group. For example, a thienylmethyl group, furylmethyl group and pyridinylmethyl group are preferable.

The "$C_3$ to $C_{14}$ cycloalkyl group" used in the specification of the present application refers to a cycloalkyl group comprising 3 to 14 carbon atoms. Examples of the preferable group include a cyclopropyl group, cyclobutyl group, cyclopentyl group, cyclohexyl group, cycloheptyl group and cyclooctyl group. For example, a cyclopentyl group, cyclohexyl group, cycloheptyl group and cyclooctyl group are preferable.

The "$C_4$ to $C_9$ cycloalkylaklyl group" used in the specification of the present application refers to a group of the above-defined "$C_1$ to $C_{22}$ alkyl group" having the above-defined "$C_3$ to $C_{14}$ cycloalkyl group" as a substituent. Specific examples include a cyclopropylmethyl group, cyclobutylmethyl group, cyclopentylmethyl group, cyclohexylmethyl group, cycloheptylmethyl group and cyclooctylmethyl group. For example, a cyclopropylmethyl group, cyclobutylmethyl group and cyclopentylmethyl group are preferable.

The "$C_1$ to $C_{22}$ alkoxy group/$C_2$ to $C_{22}$ alkoxy group" used in the specification of the present application refers to a group obtained by bonding an oxygen atom to a terminal of the above-defined "$C_1$ to $C_{22}$ alkyl group/$C_2$ to $C_{22}$ alkoxy group". Examples of the preferable group include a methoxy group (excluded in the case of $C_2$ to $C_{22}$ alkyl group), ethoxy group, n-propoxy group, an iso-propoxy group, n-butoxy group, iso-butoxy group, sec-butoxy group, tert-butoxy group, n-hexyloxy group, iso-pentyloxy group, sec-pentyloxy group, n-hexyloxy group, iso-hexyloxy group, 1,1-dimethylpropyloxy group, 1,2-dimethylpropoxy group, 2,2-dimethylpropyloxy group, 1-ethyl-2-methylpropoxy group, 1,1,2-trimethylpropoxy group, 1,2,2-trimethylpropoxy group, 1,1-dimethylbutoxy group, 1,2-dimethylbutoxy group, 2,2-dimethylbutoxy group, 2,3-dimethylbutyloxy group, 1,3-dimethylbutoxy group, 2-ethylbutoxy group, 2-methylpentoxy group, 3-methylpentoxy group and hexyloxy group. For example, a methoxy group, ethoxy group, n-propoxy group, iso-propoxy group, iso-butoxy group and 2,2-dimethylpropyloxy group are preferable.

The "unsaturated $C_2$ to $C_{22}$ alkoxy group" used in the specification of the present application refers to a group obtained by bonding an oxygen atom to a terminal of the above-defined "unsaturated $C_2$ to $C_{22}$ alkyl group". Examples of the preferable group include a vinyloxy group, allyloxy group, 1-propenyloxy group, isopropenyloxy group, 2-methyl-1-propenyloxy group, 2-methyl-2-propenyloxy group, 1-butenyloxy group, 2-butenyloxy group, 3-butenyloxy group, 1-pentenyloxy group, 1-hexenyloxy group, 1,3-hexanedienyloxy group, 1,5-hexanedienyloxy group, propargyloxy group and 2-butynyloxy group. For example, an allyloxy group, propargyloxy group and 2-butynyloxy group are preferable.

The "$C_6$ to $C_{14}$ aryloxy group" used in the specification of the present application refers to a group obtained by bonding an oxygen atom to a terminal of the above-defined "$C_6$ to $C_{14}$ aryl group". Specific examples include a phenyloxy group, indenyloxy group, 1-naphthyloxy group, 2-naphthyloxy group, azulenyloxy group, heptalenyloxy group, indacenyloxy group, acenaphthyloxy group, fluorenyloxy group, phenalenyloxy group, phenanthrenyloxy group and anthracenyloxy group. For example, a phenyloxy group, 1-naphthyloxy group and 2-naphthyloxy group are preferable.

The "$C_7$ to $C_{22}$ aralkyloxy group" used in the specification of the present application refers to a group obtained by bonding an oxygen atom to a terminal of the above-defined "$C_7$ to $C_{22}$ aralkyl group". Specific examples include a benzyloxy group, phenethyloxy group, 3-phenylpropyloxy group, 4-phenylbutyloxy group, 1-naphthylmethyloxy group and 2-naphthylmethyloxy group. For example, a benzyloxy group is preferable.

The "5-membered to 14-membered heteroaralkyloxy group" used in the specification of the present application refers to a group obtained by bonding an oxygen atom to a terminal of the above-defined "5-membered to 14-membered heteroaralkyl group". Specific examples include a thienylmethyloxy group, furylmethyloxy group, pyridinylmethyloxy group, pyridazinylmethyloxy group, pyrimidinylmethyloxy group and pyrazinylmethyloxy group. For example, a thienylmethyloxy group, furylmethyloxy group and pyridinylmethyloxy group are preferable.

The "5-membered to 14-membered heteroaralkyloxy group" used in the specification of the present application refers to a group obtained by bonding an oxygen atom to a terminal of the above-defined "5-membered to 14-membered heteroaralkyl group". Specific examples include a pyrrolyloxy group, pyridinyloxy group, pyridazinyloxy group, pyrimidinyloxy group, pyrazinyloxy group, triazolyloxy group, tetrazolyloxy group, benzotriazolyloxy group, pyrazolyloxy group, imidazolyloxy group, benzimidazolyloxy group, indolyloxy group, isoindolyloxy group, indolizinyloxy group, purinyloxy group, indazolyloxy group, quinolinyloxy group, isoquinolinyloxy group, quinolizinyloxy group, phthalazyloxy group, naphthyridinyloxy group, quinoxalinyloxy group, quinazolinyloxy group, cinnolinyloxy group, pteridinyloxy group, imidazotriazinyloxy group, pyrazinopyridazinyloxy group, acridinyloxy group, phenanthridinyloxy group, carbazolyloxy group, carbazolinyloxy group, perimidinyloxy group, phenanthrolinyloxy group, phenazinyloxy group, imidazopyridinyloxy group, imidazopyrimidinyloxy group, pyrazolopyridinyloxy group, pyrazolopyridinyloxy group, thienyloxy group, benzothienyloxy group, furyloxy group, pyranyloxy group, cyclopentapyranyloxy group, benzofuryloxy group, isobenzofuryloxy group, thiazolyloxy group, isothiazolyloxy group, benzothiazolyloxy group, benzothiadiazolyloxy group, phenothiazinyloxy group, isoxazolyloxy group, furazanyloxy group, phenoxazinyloxy group, oxazolyloxy group, isoxazolyloxy group, benzoxazolyloxy group, oxadiazolyloxy group, pyrazolooxazolyloxy group, imidazothiazolyloxy group, thienofuranyloxy group, furopyrrolyloxy group and pyridoxazinyloxy group. For example, a thienyloxy group, pyridinyloxy group, pyrimidinyloxy group and pyrazinyloxy group are preferable.

The "aliphatic $C_2$ to $C_{22}$ acyl group" used in the specification of the present application refers to a group obtained by bonding a carbonyl group to a terminal of the above-defined "$C_1$ to $C_{22}$ alkyl group" or "unsaturated $C_2$ to $C_{22}$ alkyl group". Examples include an acetyl group, propionyl group, butyryl group, iso-butyryl group, valeryl group, iso-valeryl group, pivaloyl group, caproyl group, decanoyl group, lauroyl group, myristoyl group, palmitoyl group, stearoyl group, arachidoyl group, acryloyl group, propioloyl group, crotonoyl group, iso-crotonoyl group, oleoyl group and linolenoyl group. An aliphatic acyl group having 2 to 6 carbon atoms, such as an acetyl group, propionyl group, butyryl group, iso-butyryl group or acryloyl group, is preferable.

The "aromatic $C_7$ to $C_{15}$ acyl group" used in the specification of the present application refers to a group obtained by bonding a carbonyl group to a terminal of the above-defined "$C_6$ to $C_{14}$ aryl group" or "5-membered to 14-membered heteroaryl group". Examples include a benzoyl group, 1-naphthoyl group, 2-naphthoyl group, picolinoyl group, nicotinoyl group, isonicotinoyl group, furoyl group and thiophenecarbonyl group. For example, a benzoyl group, picolinoyl group, nicotinoyl group and isonicotinoyl group are preferable.

The "$C_1$ to $C_{22}$ alkylsulfonyl group" used in the specification of the present application refers to a sulfonyl group to which the above-defined "$C_1$ to $C_{22}$ alkyl group" is bonded. Specific examples include a methanesulfonyl group, ethanesulfonyl group, n-propanesulfonyl group and isopropanesulfonyl group. For example, a methanesulfonyl group is preferable.

The "$C_6$ to $C_{14}$ arylsulfonyl group" used in the specification of the present application refers to a sulfonyl group to which the above-defined "$C_6$ to $C_{14}$ aryl group" is bonded. Specific examples include a benzenesulfonyl group, 1-naphthalenesulfonyl group and 2-naphthalenesulfonyl group. For example, a benzenesulfonyl group is preferable.

The "aliphatic $C_2$ to $C_{22}$ acyloxy group" used in the specification of the present application refers to a group obtained by bonding an oxygen atom to a terminal of the above-defined "aliphatic $C_2$ to $C_{22}$ acyl group". Examples include an acetoxy group, propionyloxy group and acryloxy group. For example, an acetoxy group and propionyloxy group are preferable.

The "$C_2$ to $C_{22}$ alkoxycarbonyl group" used in the specification of the present application refers to a group obtained by bonding a carbonyl group to a terminal of the above-defined "$C_1$ to $C_{22}$ alkoxy group". Examples include a methoxycarbonyl group, ethoxycarbonyl group, n-propoxycarbonyl group, iso-propoxycarbonyl group, n-butoxycarbonyl group, iso-butoxycarbonyl group, sec-butoxycarbonyl group and tert-butoxycarbonyl group. For example, an ethoxycarbonyl group, iso-propoxycarbonyl group and tert-butoxycarbonyl group are preferable.

The "unsaturated $C_3$ to $C_{22}$ alkoxycarbonyl group" used in the specification of the present application refers to a group obtained by bonding a carbonyl group to a terminal of the above-defined "unsaturated $C_2$ to $C_{22}$ alkoxy group". Examples include a vinyloxycarbonyl group, allyloxycarbonyl group, 1-propenyloxycarbonyl group, isopropenyloxycarbonyl group, propargyloxycarbonyl group and 2-butynyloxycarbonyl group. For example, an allyloxycarbonyl group is preferable.

The "$C_1$ to $C_{22}$ alkylthio group" used in the specification of the present application refers to a group obtained by bonding a sulfur atom to a terminal of the above-defined "$C_1$ to $C_{22}$ alkyl group". Examples include a methylthio group, ethylthio group, n-propylthio group and iso-propylthio group. For example, a methylthio group and ethylthio group are preferable.

The "$C_1$ to $C_{22}$ alkylsulfinyl group" used in the specification of the present application refers to a group obtained by bonding a sulfinyl group to a terminal of the above-defined "$C_1$ to $C_{22}$ alkyl group". Examples include a methanesulfinyl group, ethanesulfinyl group, n-propanesulfinyl group and iso-propanesulfinyl group. For example, a methanesulfinyl group and ethanesulfinyl group are preferable.

The "$C_1$ to $C_{22}$ alkylsulfonyloxy group" used in the specification of the present application refers to a group obtained by bonding an oxygen atom to a terminal of the above-defined "$C_1$ to $C_{22}$ alkylsulfonyl group". Examples include a methaneulfonyloxy group, ethanesulfonyloxy group, n-propanesulfonyloxy group and iso-propanesulfonyloxy group. For example, a methanesulfonyloxy group is preferable.

Given as the substituent in a group "which may have a substituent" used in the specification of the present application is one or more groups selected from:

(1) a halogen atom, (2) a hydroxyl group, (3) a thiol group, (4) a nitro group, (5) a nitroso group, (6) a cyano group, (7) a carboxyl group, (8) a sulfonyloxy group, (9) an amino group,

(10) a $C_1$ to $C_{22}$ alkyl group (for example, a methyl group, ethyl group, n-propyl group, iso-propyl group, n-butyl group, iso-butyl group, sec-butyl group or tert-butyl group),

(11) an unsaturated $C_2$ to $C_{22}$ alkyl group (for example, a vinyl group, allyl group, 1-propenyl group, isopropenyl group, ethynyl group, 1-propynyl group, 2-propynyl group, 1-butynyl group, 2-butynyl group or 3-butynyl group),

(12) a $C_6$ to $C_{14}$ aryl group (for example, a phenyl group, 1-naphthyl group or 2-naphthyl group),

(13) a 5-membered to 14-membered heteroaryl group (for example, a thienyl group, furyl group, pyridinyl group, pyridazinyl group, pyrimidinyl group or pyrazinyl group),

(14) a 3-membered to 14-membered non-aromatic heterocyclic group (for example, an aziridinyl group, azetidyl group, pyrrolidinyl group, pyrrolyl group, piperidinyl group, piperazinyl group, homopiperidinyl group, homopiperazinyl group, imidazolyl group, pyrazolidinyl group, imidazolidyl group, morpholinyl group, thiomorpholinyl group, imidazolinyl group, oxazolinyl group or quinuclidinyl group),

(15) a $C_3$ to $C_{14}$ cycloalkyl group (for example, a cyclopropyl group, cyclobutyl group, cyclopentyl group, cyclohexyl group, cycloheptyl group or cyclooctyl group),

(16) a $C_1$ to $C_{22}$ alkoxy group (for example, a methoxy group, ethoxy group, n-propoxy group, iso-propoxy group, sec-propoxy group, n-butoxy group, iso-butoxy group or tert-butoxy group),

(17) an unsaturated $C_2$ to $C_{22}$ alkoxy group (for example, a vinyloxy group, allyloxy group, 1-propenyloxy group, isopropenyloxy group, ethynyloxy group, 1-propynyloxy group, 2-propynyloxy group, 1-butynyloxy group or 2-butynyloxy group),

(18) a $C_6$ to $C_{14}$ aryloxy group (for example, a phenyloxy group, 1-naphthyloxy group or 2-naphthyloxy group),

(19) a $C_7$ to $C_{22}$ aralkyloxy group (for example, a benzyloxy group, phenethyloxy group, 3-phenylpropyloxy group, 4-phenylbutyloxy group, 1-naphthylmethyloxy group or 2-naphthylmethyloxy group),

(20) a 5-membered to 14-membered heteroaralkyloxy group (for example, a thienylmethyloxy group, furylmethyloxy group, pyridinylmethyloxy group, pyridazinylmethyloxy group, pyrimidinylmethyloxy group or pyrazinylmethyloxy group),

(21) a 5-membered to 14-membered heteroaryloxy group (for example, a thienyloxy group, furyloxy group, pyridinyloxy group, pyridazinyloxy group, pyrimidinyloxy group or pyrazinyloxy group),

(22) an aliphatic $C_2$ to $C_{22}$ acyl group (for example, an acetyl group, propionyl group, butyryl group, iso-butyryl group, valeryl group, iso-valeryl group, pivaloyl group, caproyl group, decanoyl group, lauroyl group, myristoyl group, palmitoyl group, stearoyl group, arachidoyl group, acryloyl group, propioloyl group, crotonoyl group, isocrotonoyl group, oleoyl group or linolenoyl group),

(23) an aromatic $C_7$ to $C_{15}$ acyl group (for example, a benzoyl group, 1-naphthoyl group or 2-naphthoyl group),

(24) an aliphatic $C_2$ to $C_{22}$ acyloxy group (for example, an acetoxy group, propionyloxy group or acryloxy group),

(25) a $C_2$ to $C_{22}$ alkoxycarbonyl group (for example, a methoxycarbonyl group, ethoxycarbonyl group, n-propoxycarbonyl group, isopropoxycarbonyl group, n-butoxycarbonyl group, iso-butoxycarbonyl group, sec-butoxycarbonyl group or tert-butoxycarbonyl group),

(26) an unsaturated $C_3$ to $C_{22}$ alkoxycarbonyl group (for example, a vinyloxycarbonyl group, allyloxycarbonyl group, 1-propenyloxycarbonyl group, isopropenyloxycarbonyl group, propargyloxycarbonyl group or 2-butynyloxycarbonyl group),

(27) a $C_1$ to $C_{22}$ alkylthio group (for example, a methylthio group, ethylthio group, n-propylthio group or iso-propylthio group),

(28) a $C_1$ to $C_{22}$ alkylsulfinyl group (for example, a methanesulfinyl group, ethanesulfinyl group, n-propanelfinyl group or iso-propanesulfinyl group),

(29) a $C_1$ to $C_{22}$ alkylsulfonyl group (for example, a methanesulfonyl group, ethanesulfonyl group, n-propanesulfonyl group or iso-propanesulfonyl group),

(30) a $C_6$ to $C_{14}$ arylsulfonyl group (for example, a benzenesulfonyl group, 1-naphthalenesulfonyl group or 2-naphthalenesulfonyl group),

(31) a $C_1$ to $C_{22}$ alkylsulfonyloxy group (for example, a methanesulfonyloxy group, ethanesulfonyloxy group, n-propanesulfonyloxy group or iso-propanesulfonyloxy group),

(32) a carbamoyl group,

(33) a formyl group, and the like. For example, an amino group, a $C_1$ to $C_{22}$ alkyl group, an unsaturated $C_2$ to $C_{22}$ alkyl group, a $C_6$ to $C_{14}$ aryl group, a 5-membered to 14-membered heteroaryl group, a 3-membered to 14-membered non-aromatic heterocyclic group and a $C_3$ to $C_{14}$ cycloalkyl group are preferable. In particular, for example, an amino group, a $C_1$ to $C_{22}$ alkyl group, a 3-membered to 14-membered non-aromatic heterocyclic group and a $C_3$ to $C_{14}$ cycloalkyl group are preferable. In addition, the above-described amino group (9) and carbamoyl group (31) given as the substituents in the above-described group "which may have a substituent" may be each further substituted with one or two $C_1$ to $C_{22}$ alkyl groups, unsaturated $C_2$ to $C_{22}$ alkyl groups or $C_6$ to $C_{14}$ aryl groups.

Next, the compound of the formula (I) of the present invention will be elucidated.

The compound of the formula (I) inhibits VEGF production under a hypoxic condition, and possesses an activity of inhibiting proliferation of solid cancer cells in vivo. As the compound of the formula (I) has structural characteristics on the side chain at the 7-position and/or the side chain at the 21-position, a compound of the above-described formula (I-a) is more preferable, and a compound of the formula (I-b) is particularly preferable. As detailed aspects of more preferable compounds, the compounds of the above-described items "4." to "19." of the present invention can be exemplified.

Preferable examples of the compound of the formula (I) will be described below. Among compounds of the formula (I) including those of later-described examples, Compound 1, Compound 2 and Compound 3 are preferable. Compound 1 and the like can be given as a particularly preferable compound.

Next, a method for producing the compound of the formula (I) of the present invention will be described.

The compound of the formula (I) can be produced by preparing a physiologically active substance 11107B (a compound of the formula (I), wherein $R^7$ is an acetoxy group, and $R^{21}$ is a hydroxyl group), as a key compound, by culturing a strain belonging to the genus *Streptomyces*, which is capable of producing 11107B, under aerobic conditions, and collecting the compound from the cells and culture solution; and following chemical modification of the key compound by a conventional method.

First, a method for producing 11107B will be elucidated.

As a microorganism used for producing 11107B, the following deposited strain can be mentioned. The above-described strain was internationally deposited with International Patent Organism Depositary (IPOD), National Institute of Advanced Industrial Science and Technology in Central 6, 1-1-1 Higashi, Tsukuba-shi, Ibaraki 305-8566, Japan on Nov. 27, 2001. Specifically, *Streptomyces* sp. Mer-11107 was deposited with National Institute of Bioscience and Human-Technology, Agency of Industrial Science and Technology in 1-1-3 Higashi, Tsukuba-shi, Ibaraki 305-8566, Japan as FERM P-18144 on Dec. 19, 2000, and was transferred to International Patent Organism Depositary (IPOD), National Institute of Advanced Industrial Science and Technology in Central 6, 1-1-1 Higashi, Tsukuba-shi, Ibaraki 305-8566, Japan under the international depositary number FERM BP-7812 on Nov. 27, 2001.

There are no specific limitations to the strains for producing 11107B, including mutants of these strains, insofar as they belong to the genus *Streptomyces*, and are capable of producing 11107B. In addition to the above-described strain, *Streptomyces* sp. A-1532, *Streptomyces* sp. A-1533 and *Streptomyces* sp. A-1534 can be mentioned, for example. These strains were also internationally deposited with International Patent Organism Depositary (IPOD), National Institute of Advanced Industrial Science and Technology in Central 6, 1-1-1 Higashi, Tsukuba-shi, Ibaraki 305-8566, Japan as FERM BP-7849, FERM BP-7850 and FERM BP-7851, respectively, on Jan. 18, 2002.

Next, the production of 11107B will be elucidated in detail with respect to 1. characteristics of the isolated producing strain, 2. a method for culturing the producing strain and 3. a method for purifying the active substance.

1. Characteristics of the Isolated Producing Strain

It is expected that, as a strain used in the present invention, any strain belonging to the genus *Streptomyces* which is capable of producing 11107B can be used. As a representative strain, a strain numbered as Mer-11107 by the present inventors can be given. Microbiological characteristics of the strain are as follows.

(1). Morphology

In the strain, spiral aerial hyphae are elongated from substrate hyphae. At the end of the matured aerial hyphae, a spore chain composed of about 10 to 20 cylindrical spores is formed. Each spore has a size of about 0.7 µm×1.0 µm, and has a smooth surface. No atypical organs such as sporangia, sclerotia and flagella are observed.

(2). Growth Conditions in Various Culture Media

Culture characteristics of the strain after culturing on various culture media at 28° C. for two weeks are shown as follows. Color tones are described according to Color Harmony Manual of Container Corporation of America, and indicated as a color name and a symbol shown in parentheses.

1) Yeast Extract-Malt Extract Agar

The strain grows well. On the surface, the aerial hyphae of the cultured strain are branched, become divided and form gray spores (light gray; d). The reverse side color is light melon yellow (3ea). No soluble pigment is observed.

2) Oatmeal Agar

The strain grows moderately. On the surface, the aerial hyphae of the cultured strain are branched, become divided and form gray spores (gray; g). The reverse side color is nude tan (4gc) or putty (1½ ec). No soluble pigment is observed.

3) Inorganic Salts-Starch Agar

The strain grows well. On the surface, the aerial hyphae adhere of the cultured strain are branched, become divided and form gray spores (gray; e). The reverse side color is fawn (4ig) or gray (g). No soluble pigment is observed.

4) Glycerol-Asparagine Agar

The strain grows well. On the surface, the aerial hyphae of the cultured strain are branched, become divided and form white spores (white; a). The reverse side color is pearl pink (3ca). No soluble pigment is observed.

5) Peptone-Yeast Extract-Iron Agar

The strain grows poorly. On the surface, no aerial hyphae of the cultured strain are branched. The reverse side color is light melon yellow (3ea). No soluble pigment is observed.

6) Tyrosine Agar

The strain grows well. On the surface, the aerial hyphae of the cultured strain are branched, become divided and form white spores (white; a). The reverse side color is pearl pink (3ca). No soluble pigment is observed.

(3). Assimilability of Various Carbon Sources

The growth status of the strain after culturing in a medium, in which various carbon sources are added to a Pridham-Godlieb agar culture medium, at 28° C. for two weeks is shown as follows.

| | |
|---|---|
| 1) L-arabinose | ± |
| 2) D-xylose | ± |
| 3) D-glucose | + |// -continued
| 4) D-fructose | + |
| 5) Sucrose | + |
| 6) Inositol | + |
| 7) L-rhamnose | − |
| 8) D-mannitol | + |
| 9) Raffinose | + |

(The symbol "+" means "positive", the symbol "±" means "weakly positive", and the symbol "−" means "negative".)

(4). Physiological Properties

Physiological properties of the strain are as follows.

(a) Temperature range for growth (yeast extract-malt extract agar, cultured for two weeks): 12° C. to 37° C.

(b) Optimal temperature range for growth (yeast extract-malt extract agar, cultured for two weeks): 21° C. to 33° C.

(c) Gelatin liquefaction (glucose-peptone-gelatin medium): negative (d) Milk coagulation (skim milk medium): negative (e) Milk peptonization (skim milk medium): negative (f) Starch hydrolysis (Inorganic salt-starch agar medium): positive (g) Melanin-like pigment production (peptone-yeast-iron agar): negative (tyrosine culture medium): negative (h) Hydrogen sulfide production (peptone-yeast extract-iron agar): negative (i) Nitrate reduction (0.1% potassium nitrate-containing broth): negative (j) NaCl tolerance (yeast extract-malt extract agar, cultured for two weeks):

Growing at a NaCl concentration of 4% or less (5). Cell Component

LL-diaminopimelic acid and glycine were detected from the cell walls of the strain.

Based on the toxonomic characteristics described above, this strain is considered to belong to the genus *Streptomyces*. Accordingly, the present inventors named the strain *Streptomyces* sp. Mer-11107, and deposited the strain with National Institute of Bioscience and Human-Technology, Agency of Industrial Science and Technology under the international depositary number FERM P-18144.

2. A Method for Culturing the Production Strain

The physiologically active substance 11107B of the present invention can be produced by inoculating the above-described strain into a nutrient culture medium, and aerobically culturing the strain. As a strain for producing the physiologically active substance 11107B, any strain belonging to the genus *Streptomyces* which is capable of producing 11107B compound can be used in the present invention without limitations to the above-described strain.

Although the method for culturing the above-described microorganism is, in principle, in accordance with a method for culturing a common microorganism, it is usually preferable that the method be conducted under aerobic conditions as shaking flask culture, tank culture by liquid culture, or the like. Any culture medium may be used for the culture, insofar as the medium contains a nutrient source that can be utilized by a microorganism belonging to the genus *Streptomyces*. Any of various synthetic culture media, semi-synthetic culture media and natural culture media can be used. In the composition of a culture medium, as carbon sources, glucose, sucrose, fructose, glycerol, dextrin, starch, molasses and soybean oil, for example, can be used singly or in a combination of two or more. As nitrogen sources, organic nitrogen sources such as pharmamedia, peptone, meat extract, soybean meal, casein, amino acid, yeast extract and urea, for example, and inorganic nitrogen sources such as sodium nitrate and ammonium sulfate, for example, can be used singly or in a combination of two or more. In addition, for example, salts such as sodium chloride, potassium chloride, calcium carbonate, magnesium sulfate, sodium phosphate, potassium phosphate and cobalt chloride, heavy metal salts, and vitamins such as vitamin B and biotin can be added for use as required. In the case where a culture medium foams when culturing, various antifoaming agents can be appropriately added to the culture medium. When the antifoaming agent is added, the concentration must be adjusted so that production of the target substance is not adversely affected. For example, the concentration used is preferably 0.05% or less.

The culture conditions can be appropriately selected, insofar as the above-described strain is grown well so that the above-described substance can be produced. It is preferable that the pH of a culture medium be adjusted to about 5 to 9, for example, and typically near neutral. It is appropriate that the culture temperature be maintained at typically 20 to 40° C., and preferably 23 to 35° C. The culture period is about two to eight days, and typically about three to five days. As a matter of course, various culture conditions as described above can be changed according to the species and properties of the microorganism used, external conditions, and the like, and optimal conditions can be selected. The physiologically active substance 11107B of the present invention accumulated in a culture solution can be collected by a typical separation methods utilizing its characteristics, for example, solvent extraction or resin adsorption.

3. A Method for Purifying the Active Substance

After termination of the culture, in order to isolate 11107B from a culture solution, separation and purification methods used for isolating a microbial metabolite from the culture broth can be generally used. For example, all known methods such as organic solvent extraction using methanol, ethanol, butanol, ethyl acetate, chloroform, or the like, various types of ion exchange chromatography, gel filtration chromatography using Sephadex LH-20 or the like, active carbon, adsorption-desorption treatment by adsorption chromatography or thin-layer chromatography using, silica gel, or the like, and high-performance liquid chromatography using a reverse phase column are applicable to this method. The purification method is not specifically limited to the methods listed here.

By using these methods singly, in a combination of two or more in an arbitrary order or repetitively, 11107B can be isolated and purified.

Next, a method for preparing the compound of the formula (I) will be described.

Various compounds of the formula (I) can be synthesized by preparing 11107B isolated and purified as a starting compound, and converting the acetoxy group at the 7-position and/or the hydroxyl group at the 21-position of isolated and purified 11107B as a starting compound into a desired substituent for the formula (I) by employing general organic synthetic procedures, for example, A. a method for preparing a urethane derivative, B. a method for preparing a thiourethane derivative, C. a method for preparing an ether derivative, D. a method for preparing an ester derivative, E. a method for preparing a phosphoric ester derivative or amidophosphoric ester derivative, F. a method for preparing a sulfuric ester derivative or amidosulfuric ester derivative, G. a method for preparing a halogen derivative, H. a method for preparing a sulfonic ester derivative and I. a method for preparing an amine derivative, singly or in a combination of two or more. Further, protective groups can be introduced into and removed from hydroxyl groups at the 3-position, 6-position and 21-position of 11107B, as required. This can be conducted according to a method described in a document (see T. W. Green, Protective Groups in Organic Synthesis, John Wiley & Sons Inc., 3rd Edition) or a method similar to this method, in a different way in accordance with the type of the protective group and the stability of the compound used for the preparation. The compound of the formula (I) can be prepared by using the introduction or removal reactions of the protective group for a hydroxyl group and the above-described preparation in a suitable combination. Specifically, the compound of the formula (I), wherein $R^7$ and $R^{21}$ are substituents listed in the above-described category 8), can be prepared by using the preparation of a urethane derivative, a thiourethane derivative, an amidosulfuric ester derivative and an amine derivative, or the like; the compound of the formula (I), wherein $R^7$ and $R^{21}$ are substituents listed in the above-described categories 1) to 4), can be prepared by using the preparation for an ether derivative; the compound of the formula (I), wherein $R^7$ and $R^{21}$ are substituents listed in the above-described category 5), can be prepared by using the preparation for an ester derivative; the compound of the formula (I), wherein $R^7$ and $R^{21}$ are substituents listed in the above-described categories 10) to 12), can be produced by using the preparation for a phosphoric ester derivative or the preparation for an amidophosphoric ester derivative; the compound of the formula (I), wherein $R^7$ and $R^{21}$ are substituents listed in the above-described category 9), can be prepared by using the preparation for a sulfuric ester derivative or the preparation for a sulfonic ester derivative; the compound of the formula (I), wherein $R^7$ and $R^{21}$ are substituents listed in the above-described category 7), can be prepared by using the preparation for a halogen derivative; and the compound of the formula (I), wherein $R^7$ and $R^{21}$ are substituents listed in the above-described category 6), can be prepared by using an introduction and removal reaction of a protective group of a hydroxyl group.

Next, various synthetic methods used for preparing the compounds of the formula (I) will be described.

A. A Method for Preparing a Urethane Derivative

The method for preparing a urethane derivative will be described in detail below with reference to the case of a 7-position urethane/21-position ester derivative as a representative example.

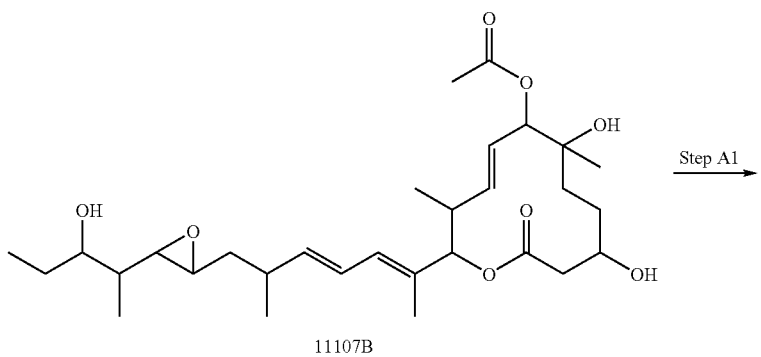

11107B

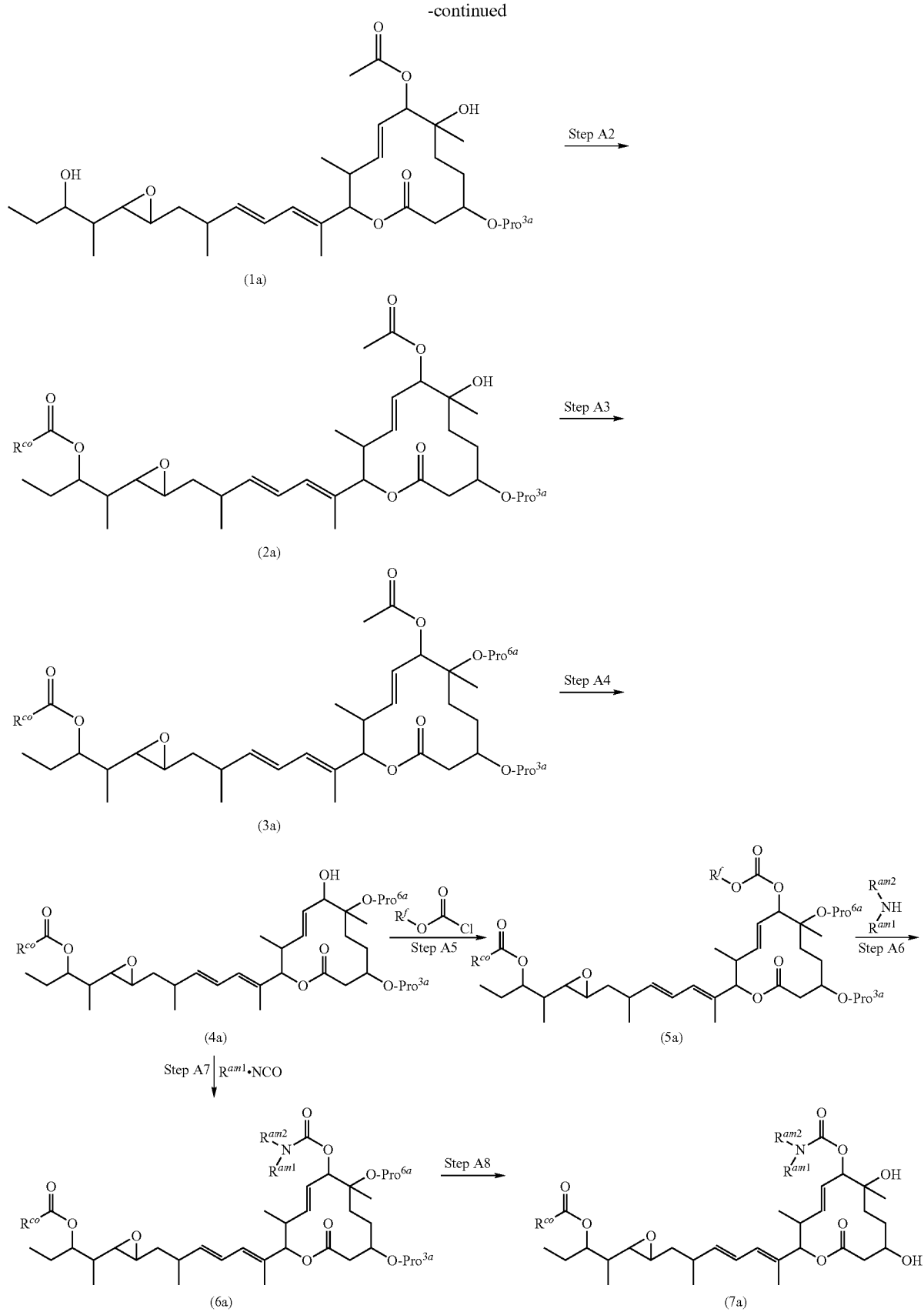

In the formulas, $Pro^{3a}$ and $Pro^{6a}$ represent a protective group, $R^{co}$ represents a hydrogen atom, a $C_1$ to $C_{22}$ alkyl group which may have a substituent, an unsaturated $C_2$ to $C_{22}$ alkyl group which may have a substituent, a $C_6$ to $C_{14}$ aryl group which may have a substituent, a 5-membered to 14-membered heteroaryl group which may have a substituent, a $C_7$ to $C_{22}$ aralkyl group which may have a substituent or a 5-membered to 14-membered heteroaralkyl group which may have a substituent, $R^f$ represents a $C_6$ to $C_{14}$ aryl group which may have a substituent, and $R^{am1}$ and $R^{am2}$ represent the same group as defined above.

The step A1 is a step of preparing the compound of the formula (1a). This step is accomplished by selectively protecting the hydroxyl group at the 3-position of 11107B.

The reaction for selectively protecting the hydroxyl group at the 3-position can be conducted with using a limited amount of triethylchlorosilane, diethylchloroisopropylsilane, chlorotriisopropylsilane or t-butylchlorodimethylsilane, for example, in the presence of a base at −10 to 40° C., and preferably 0° C. to room temperature. Although there are no specific limitations to the solvent used for the reaction, an inert solvent which does not easily react with the starting material is desirable. Examples of such solvents include ethers such as tetrahydrofuran, diethyl ether, diisopropyl ether, dioxane and dimethoxyethane; halogenated hydrocarbons such as dichloromethane; chloroform, carbon tetrachloride and 1,2-dichloroethane; hydrocarbons such as hexane, benzene, and toluene; ketones such as acetone and methyl ethyl ketone; nitriles such as acetonitrile; amides such as N,N-dimethylformamide, N,N-dimethylacetamide, N-methyl-2-pyridone and hexamethylphosphoramide; and sulfoxides such as dimethyl sulfoxide. Preferably, for example, dichloromethane, chloroform, tetrahydrofuran and N,N-dimethylformamide are used. As the base, a general organic base can be given. Examples include aromatic bases such as imidazole, 4-(N,N-dimethylamino)pyridine (which is synonymous with 4-dimethylaminopyridine, N,N-dimethylaminopyridine and dimethylaminopyridine in this specification), pyridine, 2,6-lutidine and collidine; tertiary amines such as N-methylpiperidine, N-methylpyrrolidine, triethylamine, trimethylamine, di-iso-propylethylamine, cyclohexyldimethylamine, N-methylmorpholine and 1,8-bis(dimethylamino)naphthalene; secondary amines such as diisobutylamine and dicyclohexylamine; alkyl lithium such as methyl lithium and butyl lithium; and metal alkoxides such as sodium methoxide and sodium ethoxide. For example, the compound of the hydroxyl group at the 3-position selectively protected by a t-butyldimethylsilyl group can be obtained by reacting 11107B with 1 to 4 equivalents, and preferably 1.5 to 3 equivalents of t-butyldimethylsilane and 2 to 5 equivalents, and preferably 2 to 4 equivalents of imidazole in an inert solvent such as N,N-dimethylformamide at room temperature. For example, the compound of the hydroxyl group at the 3-position selectively protected by a triethylsilyl group can be obtained by reacting 11107B with 1 to 2 equivalents, and preferably 1.2 to 1.5 equivalents of chlorotriethylsilane, 2 to 10 equivalents, and preferably 3 to 5 equivalents of a base such as triethylamine, and 0.2 to 2 equivalents, and preferably 0.3 to 0.6 equivalent of 4-(N,N-dimethylamino)pyridine in an inert solvent such as tetrahydrofuran with cooling in an ice.

The step A2 is a step of preparing the compound of the formula (2a). This step is accomplished by esterification of the hydroxyl group at the 21-position of the compound of the formula (1a).

Examples of the esterification reaction include a reaction of an acid anhydride with a base, a reaction of an acid halide with a base, a reaction of carboxylic acid with a condensing agent, a reaction of carboxylic acid with trimethylsilyl chloride and a Mitsunobu reaction. As the acid anhydride, various carboxylic anhydrides are used. Specific examples include mixed anhydrides comprising, for example acetic acid, propionic acid, butyric acid, valeric acid and benzoic acid; symmetric acid anhydrides; and cyclic acid anhydrides such as succinic anhydride, glutaric anhydride and adipic anhydride. As the acid halide, various acid chlorides and acid bromides are used. Specific examples include acetyl chloride, propionyl chloride, benzoyl chloride and benzoyl bromide. As the base, in addition to the above-described organic base, an inorganic base can be given, for example. Examples of the inorganic base include alkali metal hydrides such as sodium hydride and potassium hydride; alkaline earth metal hydrides such as calcium hydride; alkali metal hydroxides such as sodium hydroxide and potassium hydroxide; alkali metal carbonates such as sodium carbonate, potassium carbonate and cesium carbonate; and alkali metal hydrogencarbonates such as sodium hydrogencarbonate. For example, imidazole, 4-(N,N-dimethylamino)pyridine, pyridine, triethylamine and sodium hydride are preferable. As the carboxylic acid, various carboxylic acids are used. Specific example include acetic acid and propionic acid. Examples of the condensing agent include N,N-dicyclohexylcarbodiimide, trifluoroacetic anhydride, carbonyldiimidazole, N,N-diisopropylcarbodiimide and 1-ethyl-3-(3-dimethylaminopropyl)carbodiimide. In the Mitsunobu reaction, the hydroxyl group can be esterified with various carboxylic acids in the presence of triphenylphosphine and diethyl azodicarboxylate or diisopropyl azodicarboxylate. The acid anhydride and the base in combination, the acid halide and the base in combination, and the carboxylic acid and the condensing agent in combination are used for the reaction in an amount of 1 to 10 equivalents and 0.5 to 20 equivalents, 1 to 10 equivalents and 0.5 to 20 equivalents, 1 to 10 equivalents and 0.5 to 20 equivalents, and 1 to 10 equivalents and 1 to 10 equivalents, respectively; and preferably 1 to 5 equivalents and 0.5 to 10 equivalents, 1 to 5 equivalents and 0.5 to 10 equivalents, and 1 to 10 equivalents and 1 to 10 equivalents, respectively, based on the compound of the formula (1a). Although there are no specific limitations to the solvent used for each reaction, a solvent which does not easily react with the starting material is desirable. The above-described inert solvents can be given. For example, dichloromethane, chloroform and tetrahydrofuran are used as a preferable solvent. The reaction time is 10 minutes to 30 hours, and preferably 1 to 2 hours. The reaction temperature is −78° C. to a reflux temperature, and preferably −10° C. to 50° C.

The step A3 is a step of preparing the compound of the formula (3a). This step is accomplished by protecting the hydroxyl group at the 6-position of the compound of the formula (2a).

As the protective group, 1-ethoxyethyl, tetrahydropyranyl, 1-methyl-1-methoxyethyl, 1-(2-chloroethoxy)ethyl, 1-methoxycyclohexyl, 4-methoxytetrahydropyranyl, 4-methoxytetrahydrothiopyranyl and 4-methoxytetrahydrothiopyranyl-S, S-dioxide can be used, for example.

The compound with the hydroxyl group protected by 1-ethoxyethyl, tetrahydropyranyl, 1-methoxycyclohexyl, 4-methoxytetrahydropyranyl, 4-methoxytetrahydrothiopyranyl, 4-methoxytetrahydrothiopyranyl-S,S-dioxide, or the like can be synthesized by treating ethyl vinyl ether or corresponding vinyl ether such as dihydropyran and the compound of the formula (3a) in the presence of an acid.

Examples of the acid used include general organic acids such as pyridinium p-toluenesulfonate (PPTS), p-toluenesulfonic acid, camphorsulfonic acid, acetic acid, trifluoroacetic acid and methanesulfonic acid, and general inorganic acids such as hydrogen chloride, nitric acid, hydrochloric acid and sulfuric acid. Preferable examples include pyridinium p-toluenesulfonate (PPTS), p-toluenesulfonic acid and camphorsulfonic acid. Although there are no specific limitations to the solvent used for the reaction, an inert solvent which does not easily react with the starting material can be given. Preferably examples include dichloromethane, chloroform and tetrahydrofuran. The reaction time is 10 minutes to five days, and preferably one to two days. The reaction temperature is −78° C. to a reflux temperature, and preferably room temperature. The vinyl ether and the acid are used for the reaction in an amount of 1 to 100 equivalents and 0.05 to 2 equivalents, respectively; and preferably 10 to 50 equivalents and 0.1 to 0.5 equivalent, respectively, to the compound of the formula (3a).

The step A4 is a step of preparing the compound of the formula (4a). This step is accomplished by converting an acetoxy group in the compound of the formula (3a) into a hydroxyl group by treating the acetoxy group with a base in an inert solvent.

As the base, an inorganic base is mainly used. Examples include alkali metal hydrides such as sodium hydride and potassium hydride; alkaline earth metal hydrides such as calcium hydride; alkali metal hydroxides such as lithium hydroxide, sodium hydroxide and potassium hydroxide; alkali metal carbonates such as lithium carbonate, sodium carbonate and potassium carbonate; alkali metal hydrogencarbonates such as sodium hydrogencarbonate; and metal alkoxides such as lithium methoxide, sodium methoxide, sodium ethoxide and potassium t-butoxide. Examples of the organic base include guanidine, ammonia and hydrazine.

Examples of the inert solvent used include alcoholic solvents such as methanol, ethanol, isopropanol and t-butanol, and water. These can also be used in a mixture with the above-described inert solvents. The reaction time is 10 minutes to five days, and preferably 30 minutes to one day. The reaction temperature is −78° C. to a reflux temperature, and preferably room temperature. The base is used for the reaction in an amount of 1 to 10 equivalents, and preferably 2 to 5 equivalents, to the compound of the formula (3a).

The step A5 is a step of preparing the compound of the formula (5a). This step is accomplished by treating the hydroxyl group at the 7-position of the compound of the formula (4a) with a chloroformate derivative in the presence of a base. Examples of the chloroformate derivative include 4-nitrophenyl chloroformate, phenyl chloroformate, 4-chlorophenyl chloroformate, 4-bromophenyl chloroformate and 2,4-dinitrophenyl chloroformate. As the base, the above-described organic bases and inorganic bases, and the like can be given. Preferably, for example, diisopropylethylamine, 4-(N,N-dimethylamino)pyridine, triethylamine, pyridine, 2,6-lutidine and sodium hydride are used. Although there are no specific limitations to the solvent used for the reaction, a solvent which does not easily react with the starting material is desirable. The above-described inert solvents can be given. Preferably, for example, tetrahydrofuran, dichloromethane and N,N-dimethylformamide are used. The chloroformate derivative and the base are used for the reaction in an amount of 1 to 10 equivalents and 1 to 20 equivalents, respectively; and preferably 1 to 5 equivalents and 1 to 10 equivalents, respectively, to the compound of the formula (4a). Further, the reaction can be accelerated by addition of 0.2 to 2 equivalents of 4-(N,N-dimethylamino)pyridine according to need. The reaction time is 10 minutes to 30 hours, and preferably 1 to 10 hours. The reaction temperature is −78° C. to a reflux temperature, and preferably −10° C. to 50° C.

The step A6 is a step of preparing the compound of the formula (6a). This step is accomplished by treating the carbonate of the compound of the formula (5a) with an amine in an inert solvent in the presence of a base, or only with the amine.

Examples of the amine used include methylamine, ethylamine, propylamine, butylamine, octylamine, decylamine, cyclopropylamine, cyclopentylamine, cyclohexylamine, dimethylamine, diethylamine, ethylmethylamine, ethylenediamine, 1,3-propanediamine, 1,4-butanediamine, N,N-dimethylethylenediamine, N,N-dimethyl-1,3-propanediamine, N,N-dimethyl-1,4-butanediamine, N,N-diethylethylenediamine, N,N-diethyl-1,3-propanediamine, N,N-diethyl-1,4-butanediamine, N,N,N'-trimethylethylenediamine, N,N,N'-trimethyl-1,3-propanediamine, N,N,N'-trimethyl-1,4-butanediamine, N-ethyl-N',N'-dimethylethylenediamine, N-ethyl-N',N'-dimethyl-1,3-propanediamine, N-ethyl-N',N'-dimethyl-1,4-butanediamine, N,N,N'-triethylethylenediamine, N,N,N'-triethyl-1,3-propanediamine, N,N,N'-triethyl-1,4-butanediamine, N,N-diethyl-N'-methylethylenediamine, N,N-diethyl-N'-methyl-1,3-propanediamine, N,N-diethyl-N'-methyl-1,4-butanediamine, N,N'-dimethyl-N-phenylethylenediamine, N,N'-dimethyl-N-phenyl-1,3-propanediamine, N-benzyl-N,N'-dimethylethylenediamine, N-benzyl-N,N'-dimethyl-1,3-propanediamine, morpholine, thiomorpholine, thiomorpholine-S-oxide, thiomorpholine-S,S-dioxide, pyrrolidine, piperidine, piperazine, homopiperazine, 4-hydroxypiperidine, 4-methoxypiperidine, 1-methylpiperazine, 1-ethylpiperazine, 1-propylpiperazine, 1-butylpiperazine, 1-isopropylpiperazine, 1-cyclobutylpiperazine, 1-cyclopentylpiperazine, 1-cyclohexylpiperazine, 1-cycloheptylpiperazine, 1-cyclooctylpiperazine, 1-(cyclopropylmethyl)piperazine, 1-benzylpiperazine, 1-methylhomopiperazine, 1-ethylhomopiperazine, 1-(2-aminoethyl)pyrrolidine, 1-(2-(N-methylamino)ethyl)pyrrolidine, 1-(3-aminopropyl)pyrrolidine, 1-(3-(N-methylamino)propyl)pyrrolidine, 1-(2-aminoethyl)piperidine, 1-(2-(N-methylamino)ethyl)piperidine, 1-(3-aminopropyl)piperidine, 1-(3-(N-methylamino)propyl)piperidine, 4-(2-aminoethyl)morpholine, 4-(2-(methylamino)ethyl)morpholine, 4-(3-aminopropyl)morpholine, 4-(3-(N-methylamino)propyl)morpholine, 1-(2-aminoethyl)-4-methylpiperazine, 1-(3-aminopropyl)-4-methylpiperazine, 1-(3-(N-methylamino)propyl)-4-methylpiperazine, 1-amino-4-methylpiperidine, 1-methylamino-4-methylpiperidine, 1-ethyl-4-(N-methylamino)piperidine, 1-methylamino-4-propylpiperidine, 1-butyl-4-(N-methylamino)piperidine, 1-(N,N-dimethylamino)piperidine, 1-(N,N-diethylamino)piperidine, 4-(pyrrolidin-1-yl)piperidine, 4-(piperidin-1-yl)piperidine, 3-aminoquinuclidine, 3-(N-methylamino)quinuclidine, aniline, N-methylaniline, N,N-dimethyl-p-phenylenediamine, N,N-dimethyl-m-phenylenediamine, N,N,N'-trimethyl-p-phenylenediamine, N,N,N'-trimethyl-m-phenylenediamine, 1-naphthylamine, 2-naphthylamine, benzylamine, N-methylbenzylamine, phenethylamine, N-methylphenethylamine, 2-picolylamine, 3-picolylamine, 4-picolylamine, N-methyl-2-picolylamine, N-methyl-3-picolylamine, N-methyl-4-picolylamine, 2,5-diazabicyclo[2.2.1]heptane, 2-methyl-2,5-diazabicyclo[2.2.1]heptane, 3,8-diazabicyclo[3.2.1]octane and 1,4-diazabicyclo[4.3.0]nonane.

As the base, the above-described organic bases and inorganic bases, and the like can be given. Preferably, for example, diisopropylethylamine, dimethylaminopyridine, triethylamine, pyridine, 2,6-lutidine and sodium hydride are used. Although there are no specific limitations to the solvent used for the reaction, a solvent which does not easily react with the starting material is desirable. The above-described inert solvents can be given. Preferably, for example, tetrahydrofuran, dichloromethane and N,N-dimethylformamide are used. The amine and the base are used for the reaction in an amount of 1 to 10 equivalents and 2 to 20 equivalents, respectively; and preferably 1.5 to 5 equivalents and 2 to 10 equivalents, respectively, based on the compound of the formula (5a). The reaction time is 10 minutes to 30 hours, and preferably one to two hours. The reaction temperature is −78° C. to a reflux temperature, and preferably −10° C. to 50° C.

The compound of the formula (6a) can also be prepared by treating the compound of the formula (4a) with an isocyanate in an inert solvent in the presence of a base and/or cuprous chloride (step A7). Although there are no limitations to the isocyanate, ethyl isocyanate, methyl isocyanate and phenyl isocyanate can be mentioned as examples. As the base, the above-described organic bases and inorganic bases, and the like can be given. Preferably, for example, diisopropylethylamine, dimethylaminopyridine, triethylamine, pyridine, 2,6-lutidine and sodium hydride are used. Although there are no specific limitations to the solvent used for the reaction, a solvent which does not easily react with the starting material is desirable. The above-described inert solvents can be mentioned. Preferably, tetrahydrofuran, dichloromethane, N,N-dimethylformamide, and the like are used. The base and the isocyanate are used for the reaction in an amount of 1 to 30 equivalents and 1 to 30 equivalents, respectively; and preferably 2 to 15 equivalents and 2 to 15 equivalents, respectively, to the compound of the formula (4a). Cuprous chloride is used in an amount of 1 to 10 equivalents, and preferably 2 to 6 equivalents. The reaction time is 10 minutes to 30 hours, and preferably 1 to 30 hours. The reaction temperature is −78° C. to a reflux temperature, and preferably −10° C. to 50° C.

The step A8 is a step of preparing the compound of the formula (7a). This step is accomplished by deprotecting the protective group for the hydroxyl groups at the 3-position and 6-position of the compound of the formula (6a). The reaction for deprotecting the protective groups for the hydroxyl groups is conducted by a method well known in the synthetic organic chemistry.

For example, 1-ethoxyethyl, tetrahydropyranyl, 1-methoxycyclohexyl, 4-methoxytetrahydropyranyl, 4-methoxytetrahydrothiopyranyl, 4-methoxytetrahydrothiopyranyl-S,S-dioxide, triethylsilyl, trimethylsilyl, triisopropylsilyl or t-butyldimethylsilyl for each hydroxyl group can be easily deprotected by acid treatment in an inert solvent. As the acid, the above-described organic acids and inorganic acids, and the like are used. Preferable examples include pyridinium p-toluenesulfonate, p-toluenesulfonic acid and camphorsulfonic acid. Although there are no specific limitations to the solvent used for the reaction, a solvent which does not easily react with the starting material is desirable. Alcoholic solvents such as methanol, ethanol, isopropanol and t-butanol are preferable. These can be used in a mixture with the above-described inert solvents. The acid is used for the reaction in an amount of 0.5 to 5 equivalents, and preferably 1 to 3 equivalents, to the compound of the formula (6a). The reaction time is 10 minutes to 10 days, and preferably one to four days. The reaction temperature is −78° C. to a reflux temperature, and preferably −10° C. to 50° C.

Further, a derivative in which the hydroxyl groups at the 7-position and 21-position are converted into urethane structures can be synthesized by converting the hydroxyl group at the 21-position of the compound of the formula (1a) into a urethane structure by the step A5 and A6 or A7, and then conducting the steps A3, A4, A5, A6 and A8. In this case, a derivative with different urethane structures can be synthesized by applying different amines for each urethanization step.

In addition, a compound of the formula (I) with substituents $R^7$ and $R^{21}$ having various structures can be synthesized by conducting, in addition to A. urethanization as described above, B. thiourethanization, C. etherification, D. phosphoric esterification or monoamidosulfonic esterification, E. sulfuric esterification or amidosulfuric esterification, F. halogenation, G. sulfonic esterification, or H. amination instead of the step A2 or A5 and the step A6.

B. A Method for Preparing a Thiourethane Derivative (Thiourethanization)

The thiourethane derivative is synthesized by treating the compound of the formula (1a) or the compound of the formula (4a) with isothiocyanate or thiocarbamoyl chloride in an inert solvent in the presence of a base or bis(tributyltin)oxide in order to thiourethanize a hydroxyl group, and then deprotecting the protective group according to the step A8.

Although there are no limitations to the isothiocyanate used, ethyl isothiocyanate, methyl isothiocyanate, phenyl isothiocyanate, benzyl isothiocyanate and allyl isothiocyanate can be mentioned as examples. Although there are no limitations to the thiocarbamoyl chloride used in the reaction, N,N-dimethylthiocarbamoyl chloride and N-phenyl-N-methylthiocarbamoyl chloride can be mentioned as examples. As the base, the above-described organic bases and inorganic bases, and the like can be given. Preferably, for example, diisopropylethylamine, dimethylaminopyridine, triethylamine, pyridine, 2,6-lutidine and sodium hydride are used. Although there are no specific limitations to the solvent used for the reaction, a solvent which does not easily react with the starting material is desirable. The above-described inert solvents can be mentioned. Preferably, tetrahydrofuran, dichloromethane, N,N-dimethylformamide, toluene, and the like are used. The base or bis(tributyltin)oxide and the isocyanate or thiocarbamoyl chloride are used for the reaction in an amount of 1 to 5 equivalents and 1 to 10 equivalents, respectively; and preferably 1 to 3 equivalents and 2 to 5 equivalents, respectively, to the compound of the formula (1a) or the compound of the formula (4a). The reaction time is 10 minutes to 72 hours, and preferably 1 to 24 hours. The reaction temperature is −78° C. to a reflux temperature, and preferably −10° C. to 70° C.

A derivative with thiourethane structures at the both 7-position and 21-position can be synthesized as in the case of the urethane derivative.

C. A Method for Preparing an Ether Derivative (etherification)

The ether derivative is synthesized by alkylating a hydroxyl group of the compound of the formula (1a) or the compound of the formula (4a), and then deprotecting the protective group according to the step A8.

The alkylation can be accomplished by treating the compound with an alkylating agent represented by the formula $R^m$—X, wherein $R^m$ represents a $C_2$ to $C_{22}$ alkyl group which may have a substituent or an unsaturated $C_3$ to $C_{22}$ alkyl group which may have a substituent, and X represents a leaving group, in the presence of a base. Specific examples of the substituent $R^m$ include a methyl group, ethyl group, aryl group, propargyl group and benzyl group. Specific examples of the leaving group include a chloro group, bromo group, iodo group and trifluoromethanesulfonyl group. As the base, the above-described organic bases and inorganic bases, and the like can be given. Preferable examples include sodium hydride, lithium bis(trimethylsilyl)amide, lithium diisopropylamide, lithium dicyclohexylamide, potassium carbonate, cesium carbonate and 8-bis(N,N-dimethylamino)naphthalene. Although there are no specific limitations to the solvent used for the reaction, a solvent which does not easily react with the starting material is desirable. The above-described inert solvents can be mentioned. Preferably, diethyl ether, tetrahydrofuran, dimethoxyethane, toluene, and the like are used. The alkylating agent and the base are used for the reaction in an amount of 3 to 20 equivalents and 5 to 30 equivalents, respectively; and preferably 3 to 5 equivalents and 5 to 10 equivalents, respectively, to the compound of the formula (1a) or the compound of the formula (4a). The reaction time is 10 minutes to 30 hours, and preferably 1 to 2 hours. The reaction temperature is −78° C. to a reflux temperature, and preferably −10° C. to 70° C.

D. A Method for Preparing an Ester Derivative (Esterification)

The ester derivative is synthesized by esterifying a hydroxyl group of the compound of the formula (1a) or the compound of the formula (4a), and then deprotecting the protective group according to the step A8.

The esterification reaction is conducted using an acid anhydride and a base in combination, an acid halide and a base in combination, carboxylic acid and a condensing agent in combination, or Mitsunobu reaction, for example. As the acid anhydride, various carboxylic anhydrides are used. Examples include mixtures composed of acid anhydrides such as acetic anhydride, propionic anhydride, butyric anhydride, valeric anhydride and benzoic anhydride; and cyclic acid anhydrides such as symmetric acid anhydride, succinic anhydride, glutaric anhydride and adipic anhydride. Acetic anhydride, propionic anhydride, butyric anhydride, benzoic anhydride, and the like are preferable. As the acid halide, various acid chlorides and acid bromides are used, for example. For example, acetyl chloride, propionyl chloride, benzoyl chloride and benzoyl bromide are preferable. As the base, the above-described organic bases and inorganic bases, and the like can be given. For example, imidazole, 4-(N,N-dimethylamino)pyridine, pyridine and sodium hydride are preferable. As the carboxylic acid, various carboxylic acids are used. For example, acetic acid and propionic acid are preferable. As the condensing agent, dicyclohexylcarbodiimide, trifluoroacetic anhydride, carbonyldiimidazole, N,N-diisopropylcarbodiimide and 1-ethyl-3-(3-dimethylaminopropyl)carbodiimide are preferable, for example. In the Mitsunobu reaction, the hydroxyl group can be substituted with various carboxylic acids in the presence of triphenylphosphine and diethyl azodicarboxylate or diisopropyl azodicarboxylate. Although there are no specific limitations to the solvent used for each reaction, a solvent which does not easily react with the starting material is desirable. The above-described inert solvents can be given. Preferably, for example, dichloromethane, chloroform and tetrahydrofuran are used. The acid anhydride and the base in combination, the acid halide and the base in combination, and the carboxylic acid and the condensing agent in combination are used for the reaction in an amount of 1 to 10 equivalents and 3 to 20 equivalents, 1 to 10 equivalents and 3 to 20 equivalents, and 1 to 20 equivalents and 1 to 20 equivalents, respectively; and preferably 1 to 5 equivalents and 2 to 10 equivalents, 1 to 5 equivalents and 2 to 10 equivalents, and 1 to 5 equivalents and 1 to 5 equivalents, respectively, to the compound of the formula (1a) and the compound of the formula (4a). Further, the reaction can be accelerated by addition of 0.2 to 2 equivalents of 4-dimethylaminopyridine according to need. The reaction time is 10 minutes to 30 hours, and preferably 1 to 2 hours. The reaction temperature is −78° C. to a reflux temperature, and preferably −10° C. to 50° C.

E. A method for Preparing a Phosphoric Ester Derivative or Amidophosphoric Ester Derivative (Phosphoric Esterification or Monoamidophosphoric Esterification)

The phosphoric ester derivative is synthesized by conducting phosphoric esterification of a hydroxyl group of the compound of the formula (1a) or the compound of the formula (4a), and then deprotecting the protective group according to the step A8.

The phosphoric esterification is conducted using phosphoric halide and a base, for example. As the phosphoric halide, various phosphoric halides are used. Examples include dialkoxyphosphoryl chloride, diphenyloxyphosphoryl chloride, alkoxy(N,N-disubstituted amino)phosphoryl chloride, allyloxy(N,N-disubstituted amino)phosphoryl chloride, alkoxy(N-substituted amino)phosphoryl chloride and allyloxy(N-substituted amino)phosphoryl chloride. As the base, the above-described organic bases and inorganic bases, and the like can be given. For example, pyridine, 4-(N,N-dimethylamino)pyridine, triethylamine, ethyldiisopropylamine, sodium hydride, n-butyl lithium, potassium carbonate and sodium carbonate are preferable. Although there are no specific limitations to the solvent used for each reaction, a solvent which does not easily react with the starting material is desirable. The above-described inert solvents can be given. Preferably, for example, dichloromethane, chloroform, tetrahydrofuran, acetone and N,N-dimethylformamide are used. The phosphoric halide and the base are used for the reaction in an amount of 1 to 10 equivalents and 2 to 20 equivalents, respectively; and preferably 1 to 5 equivalents and 2 to 10 equivalents, respectively, to the compound of the formula (1a) or the compound of the formula (4a). The reaction time is 10 minutes to 72 hours, and preferably 1 to 24 hours. The reaction temperature is −78° C. to a reflux temperature, and preferably −10° C. to 50° C. When the substituent at the 3-position or 6-position is a protective group for a hydroxyl group, the phosphoric ester derivative or amidophosphoric ester derivative can be prepared by removing the protective group for a hydroxyl group.

F. A Method for Preparing a Sulfuric Ester Derivative or Amidosulfuric Ester Derivative (Sulfuric Esterification or Amidosulfuric Esterification)

The sulfuric ester derivative or amidosulfuric ester is synthesized by carrying out sulfuric esterification or amidosulfuric esterification of a hydroxyl group of the compound of the formula (1a) or the compound of the formula (4a), and then deprotecting the protective group according to the step A8.

The sulfuric esterification is carried out using sulfuric halide and a base or the like. As the sulfuric halide, various sulfuric halides are used. For example, alkoxysulfonyl chloride and N,N-disubstituted sulfamoyl chloride are preferable. As the base, the above-described organic bases and inorganic bases, and the like can be given. For example, pyridine, 4-(N,N-dimethylamino)pyridine, triethylamine, ethyldiisopropylamine, sodium hydride, n-butyl lithium, potassium carbonate and sodium carbonate are preferable. Although there are no specific limitations to the solvent used for each reaction, a solvent which does not easily react with the starting material is desirable. The above-described inert solvents and the like can be mentioned. Examples of the preferable solvent include dichloromethane, chloroform, tetrahydrofuran, acetone and N,N-dimethylformamide. The sulfuric halide and the base are used for the reaction in an amount of 1 to 10 equivalents and 2 to 20 equivalents, respectively; and preferably 1 to 5 equivalents and 2 to 10 equivalents, respectively, to the compound of the formula (1a) or the compound of the formula (4a). The reaction time is 10 minutes to 72 hours, and preferably 1 to 24 hours. The reaction temperature is −78° C. to a reflux temperature, and preferably −10° C. to 50° C.

G. A Method for Preparing a Halogen Derivative (Halogenation)

The halogen derivative is synthesized by halogenating a hydroxyl group of the compound of the formula (1a) or the compound of the formula (4a), and then deprotecting the protective group according to the step A8.

The halogenation reaction can be carried out by treating diethylaminosulfur trifluoride (DAST) or triphenylphosphine with carbon tetrabromide, bromine, phosphorus tribromide, iodine or carbon tetrachloride in the presence of a base, for example. As the base, general organic bases and inorganic bases can be given. Examples include diisopropylethylamine, dimethylaminopyridine, triethylamine, pyridine, 2,6-lutidine and sodium hydride. Although there are no specific limitations to the solvent used for the reaction, a solvent which does not easily react with the starting material is desirable. Examples include tetrahydrofuran, dichloromethane and N,N-dimethylformamide. In particular, fluorination reaction using diethylaminosulfur trifluoride is preferable. Diethylaminosulfur trifluoride (DAST) is used for the reaction in an amount of 1 to 5 equivalents, and preferably 1 to 3 equivalents, to the compound of the formula (1a) or the compound of the formula (4a). The reaction time is 10 minutes to 30 hours. The reaction temperature is −78° C. to a reflux temperature.

H. A method for Preparing a Sulfonic Ester Derivative (Sulfonic Esterification)

The sulfonic ester derivative is synthesized by sulfonylating a hydroxyl group of the compound of the formula (1a) or the compound of the formula (4a), and then deprotecting the protective group according to the step A8.

The sulfonylation reaction can be carried out using sulfonyl chlorides such as p-toluenesulfonyl chloride, methanesulfonyl chloride and benzenesulfonyl chloride, for example, to act on the hydroxyl group in the presence of a base. As the base, general organic bases and inorganic bases, for example, diisopropylethylamine, dimethylaminopyridine, triethylamine, pyridine, 2,6-lutidine and sodium hydride can be given. Although there are no specific limitations to the solvent used for the reaction, a solvent which does not easily react with the starting material is desirable. Examples include tetrahydrofuran, dichloromethane and N,N-dimethylformamide. The sulfonyl chloride and the base are used for the reaction in an amount of 1 to 5 equivalents and 2 to 10 equivalents, respectively; and preferably 1 to 3 equivalents and 2 to 6 equivalents, respectively, to the compound of the formula (1a) or the compound of the formula (4a). The reaction time is 10 minutes to 30 hours. The reaction temperature is −78° C. to a reflux temperature.

I. A Method for Preparing an Amine Derivative

The amine derivative is synthesized by aminating a hydroxyl group of the compound of the formula (1a) or the compound of the formula (4a), and then deprotecting the protective group according to the step A8.

The amination can be accomplished by converting a hydroxyl group of the compound of the formula (1a) or the compound of the formula (4a) directly into an azide group, or by converting a hydroxyl group of the compound of the formula (1a) or the compound of the formula (4a) into a good leaving group, and then converting the leaving group into an azide group, and further reducing the azide group to amine, or by converting a hydroxyl group of the compound into a good leaving group, and then replaced by an amino group.

When a hydroxyl group is converted into azide, 1) diphenylphosphoryl azide (DPPA), diethyl azodicarboxylate and triphenylphosphine, 2) DPPA and 1,8-diazabicyclo[5.4.0]undeca-7-ene (DBU), 3) hydrogen azide, diethyl azodicarboxylate and triphenylphosphine, 4) DPPA, tetramethylazodicarboxamide (TMAD) and tributylphosphine or 5) sodium azide in the presence of a base can be used, for example. As the base, the above-described organic bases and inorganic bases, and the like can be given. Preferably, for example, diisopropylethylamine, dimethylaminopyridine, triethylamine, pyridine, 2,6-lutidine and sodium hydride are used. Further, the hydroxyl group can also be converted into azide by treating the group with sodium azide in the presence of a palladium catalyst. Examples of the palladium catalyst include $Pd(PPh_3)_4$. Although there are no specific limitations to the solvent used for the reaction, a solvent which does not easily react with the starting material is desirable. Examples include tetrahydrofuran, dichloromethane, N,N-dimethylformamide, toluene and benzene. The reaction time is 10 minutes to 30 hours. The reaction temperature is −78° C. to a reflux temperature.

The azide can be reduced to the amine using triphenylphosphine or lithium aluminum hydride, for example. In addition, the reduction to the amine can also be conducted using a catalyst such as palladium carbon or a Lindlar catalyst in a hydrogen atmosphere. Although there are no specific limitations to the solvent used for the reaction, a solvent which does not easily react with the starting material is desirable. Examples include tetrahydrofuran, diethyl ether and ethanol. The reaction time is 10 minutes to 30 hours. The reaction temperature is −78° C. to a reflux temperature.

The hydroxyl group can be converted into a highly leavable group according to the above-described halogenation or sulfonylation. Examples of the good leaving group include a chloro group, bromo group, iodo group, methanesulfonyl group and p-toluenesulfonyl group. Subsequently, by treating this compound in which the hydroxyl group is converted into a leaving group with an amine in an inert solvent in the presence of a base, a compound in which the hydroxyl group is converted into an amino group or an amino group having a substituent can be synthesized.

Examples of the amine used include methylamine, ethyl amine, dimethylamine and diethylamine. As the base, the above-described organic bases and inorganic bases, and the like can be given. Preferably, for example, diisopropylethylamine, dimethylaminopyridine, triethylamine, pyridine, 2,6-lutidine and sodium hydride are used. Although there are no specific limitations to the solvent used for the reaction, a solvent which does not easily react with the starting material is desirable. The above-described inert solvents can be given. Preferably, for example, tetrahydrofuran, dichloromethane and N,N-dimethylformamide are used. The reaction time is 10 minutes to 30 hours, and preferably one to two hours. The reaction temperature is −78° C. to a reflux temperature, and preferably −10° C. to 50° C.

Further, by alkylating, acylating, carbamoylating or sulfonylating the amino group in the compound obtained by the above-described amination, using a method well known in the synthetic organic chemistry and the above-described method, the compound of the formula (I) can be prepared. By appropriately combining the reactions A to I as described above with the protections and deprotections of a hydroxyl group, the compound of the formula (I) can be synthesized.

After termination of the reaction, the target product of each reaction is collected from the reaction mixture according to a conventional procedure. For example, the target product can be obtained by removing an insoluble matter by filtration and removing the solvent by distillation under reduced pressure in an appropriate manner, when the insoluble matter is present, or by diluting the reaction mixture with an organic solvent such as ethyl acetate, washing the mixture with water, drying the organic layer over anhydrous magnesium sulfate, and then removing the solvent by distillation. If required, the target product can be further purified by a conventional method, for example, column chromatography, thin-layer chromatography or high-performance liquid chromatography.

Next, in order to prove the usefulness of the present invention, VEGF transcription inhibitory action, action of inhibiting proliferation of WiDr human colon cancer cells, solid cancer proliferation inhibitory action, body weight reduction (acute toxicity), and stability in an aqueous solution of compounds as representatives of the compound of the formula (I) of the present invention were measured.

TEST EXAMPLE 1

Construction of a Reporter System for Screening Compounds Inhibiting VEGF Transcription In order to prepare a reporter system in which transcription from a VEGF promoter is reflected, a VEGF promoter sequence was cloned and inserted into a placental alkaline phosphatase (PLAP) vector to construct a reporter vector.

In order to obtain a promoter region of human VEGF, a VEGF genome was cloned from a phage library. Based on VEGF cDNA (GenBank accession number: X62568), a PCR primer with the sequence described as SEQ ID NO: 1 or SEQ ID NO: 2 was designed and used for conducting PCR, thereby obtaining a fragment of about 340 bp. A human genomic phage library (human genomic library, Clontech) was screened using this fragment as a probe to obtain pUC18-VEGFA containing a VEGF 5'-flanking region of about 5.4 kb. This pUC18-VEGFA was cut with Kpn I/Nhe I to obtain a VEGF promoter region of about 2.3 kb, and the region was inserted into the multicloning site Kpn I/Nhe I of the placental alkaline phosphatase (PLAP) reporter vector (Goto et al., Mol. Pharmacol., 49, 860-873, 1996) to construct a VEGF-PLAP vector.

The above-described VEGF-PLAP vector was introduced into U251 cells cultured in a Dulbecco's modified Eagle's medium containing 10% fetal bovine serum (DMEM, manufactured by Sigma Co.), and cultured in the presence of 1 mg/ml G418 (Merck & Co., Inc.) to establish a G418-resistant stable clone (U251/1-8 cells).

As in a report by Minchenko et al. (Cell. Mol. Biol. Res., 40, 35-39, 1994), U251/1-8 cells were confirmed to be a reporter system which secretes PLAP into a culture medium under hypoxic conditions (2% $O_2$ incubator), and in which transcription from a VEGF promoter is reflected. Compounds inhibiting VEGF production induced by hypoxic stimulation were screened using this clone as described below.

TEST EXAMPLE 2

VEGF Transcription Inhibitory Activity of a 7,21-Position-Modified 11107B Derivative In order to eliminate influence of the alkali phosphatase in the serum, the U251/1-8 cells were washed with a sufficient amount of PBS (phosphate buffered saline) twice, and treated at 65° C. for 20 minutes to inactivate the alkaline phosphatase in the serum. The cells were diluted with the DMEM culture medium containing the serum at 10%, and were plated in a 96-well plate in an amount of $4 \times 10^4$ cells/180 µl per well.

The cells were cultured in a $CO_2$ incubator (5% $CO_2$) at 37° C. overnight, and 20 µl of the above-described culture solution containing the test compound at threefold serial dilutions was added. Subsequently, the cells were cultured in hypoxic (2% $O_2$) incubator for 18 hours. To measure the PLAP activity in the culture supernatant liquid, 10 µl of the culture supernatant liquid was added to 50 µl of a 0.28 M $Na_2CO_3$—$NaHCO_3$ buffer solution (pH 10.0, 8.0 mM $MgSO_4$), and finally 50 µl of an alkaline phosphatase substrate (Lumistain, Genome Science Laboratories Co., Ltd.) was added thereto. After the reaction for one hour, chemiluminescence was detected using a microplate reader (PerkinElmer) to measure the PLAP activity as the alkaline phosphatase activity. The PLAP activity under normoxic conditions was defined as 0%, the PLAP activity of the cells when treated under hypoxic conditions was defined as 100%, and the concentration for inhibiting 50% of the PLAP activity was defined as the $IC_{50}$ value of PLAP. The $IC_{50}$ values of compounds of the formula (I) were determined. The $IC_{50}$ values of the representative compounds are shown in Table 2. The compounds of the formula (I) exhibited strong VEGF transcription inhibitory activity.

TABLE 1

| Example | VEGF transcription inhibitory activity ($IC_{50}$: nM) |
|---|---|
| 1 | 20.7 |
| 2 | 4.2 |
| 3 | 11.8 |

TEST EXAMPLE 3

Action of Inhibiting Proliferation of WiDr Human Colon Cancer Cells $2 \times 10^3$ cells/well of WiDr human colon cancer cells cultured in a Dulbecco's modified Eagle's medium containing 10% fetal bovine serum, penicillin (100 units/mL) and streptomycin (100 µg/mL) (DMEM, manufactured by Sigma Co.) were plated in a 96-well plate. The cells were cultured in a $CO_2$ incubator overnight, and 20 µL of the above-described culture solution containing the test compound at threefold serial dilutions was added for culturing the cells. After three days, 50 µL of a 3.3 mg/mL MTT solution was added, and the cells were further cultured for one hour. Then, formazan generated by reduction by living cells was extracted with 100 µL of DMSO to measure the absorbance (A540/A660), which was used as an index of the number of living cells.

The concentration for inhibiting 50% of proliferation of WiDr human colon cancer cells ($IC_{50}$ value) of the compound of the formula (I) was determined. The $IC_{50}$ values of the representative compounds are shown in Table 2. The compound of the formula (I) exhibited strong WiDr human colon cancer cell proliferation inhibitory action.

TABLE 2

| Example | WiDr human colon cancer cell proliferation inhibitory activity ($IC_{50}$: nM) |
|---|---|
| 1 | 5.9 |
| 2 | 2.4 |
| 3 | 4.8 |

As is clear from the above-described pharmacological test examples, the compound of the formula (I) of the present invention alters gene expression, and thus inhibits VEGF production, in particular. Therefore, the compound is expected to be used as a tumor treating agent, in particular, a solid cancer treating agent, cancer metastasis inhibitor, diabetic retinopathy treating agent, rheumatoid arthritis treating agent or ecchymoma treating agent. Furthermore, as can be seen in the toxicity test in Test Example 4, since the action of inhibiting growth of WiDr human colon tumors cells is exhibited at a dose not causing a significant reduction in the body weights of the test mice, the compound of the formula (I) is a compound which is highly safe. Accordingly, the compound is effective for preventing or treating a disease for which gene expression control is effective, a disease for which VEGF production inhibitory action is effective, and a disease for which angiogenesis inhibitory action is effective. The "prevention or treatment" refers to prevention, treatment, or both. More specifically, the compound of the formula (I) of the present invention is effective as an antitumor drug, in particular, an antitumor drug or tumor metastasis inhibitor against a solid cancer. Examples of the solid cancer include pancreate cancer, stomach cancer, colon cancer, breast cancer, prostate cancer, lung cancer, renal cancer, brain tumor, head and neck cancer, esophagus cancer, skin cancer, hepatic cancer, uterine cancer, uterine cervix cancer, bladder cancer, thyroid cancer, testicular tumor, villus cancer, osteosarcoma, soft-tissue sarcoma and ovarian cancer. The compound is particularly preferably used for cancers such as a colon cancer, breast cancer, prostate cancer, lung cancer, head and neck cancer, and ovarian cancer. Further, the compound is also effective as an antitumor drug against leukemia. In addition, the compound is also effective as a hemangioma treating agent. Moreover, the compound is effective as a diabetic retinopathy treating agent, rheumatoid arthritis treating agent or hemangioma treating agent based on the VEGF production inhibitory action. Additionally, the compound is also effective as an agent for treating inflammatory diseases consisting of osteoarthritis, psoriasis, delayed hypersensitive reaction and atherosclerosis.

When the above-described compound is to be prepared as an injectable solution, a pH adjuster, buffering agent, stabilizer, solubilizer, and the like are added to the active ingredient, as required, to prepare an injectable solution for subcutaneous, intramuscular, intra-articular or intravenous administration by a conventional method.

When the above-described compound is to be administered as an agent for treating or preventing various diseases, the compound may be orally administered as tablets, powder, granules, capsules, syrup, or the like, or the compound may be parenterally administered as a spray, a suppository, an injectable solution, an external use or drops. Although the dose significantly varies according to the degree of symptom, the age of the adult, the type of liver disease, and the like, the dose for the adult is typically about 1 mg to 100 mg per day in a single dose or in divided doses of several times.

A drug product is produced using general ingredients by a conventional method. Specifically, when an oral solid formulation is to be prepared, a vehicle and, as required, a binder, disintegrating agent, lubricant, coloring agent, flavoring or odor-masking agent, or the like are added to the active ingredient, and then the mixture is formed into tablets, coated tablets, granules, powder, capsules, or the like by a conventional method. These tablets or granules may be appropriately coated with sugar, gelatin or other coatings as required, naturally.

EXAMPLES

The present invention will be described more specifically below with reference to examples and reference examples. However, the present invention should not be limited to these examples.

The abbreviations used in the chemical formulas of the examples are shown below.
Ac: Acetyl group
Bz: Benzoyl group
EE: 1-Ethoxyethyl group
Me: Methyl group
Ms: Methanesulfonyl group
TES: Triethylsilyl group
Ts: p-Toluenesulfonyl group Example 1

(8E,12E,14E)-21-benzoyloxy-3,6-dihydroxy-6,10,12,16,20-pentamethyl-7-((4-methylpiperazin-1-yl)carbonyl)oxy-18,19-epoxytricosa-8,12,14-trien-11-olide (Compound 1)

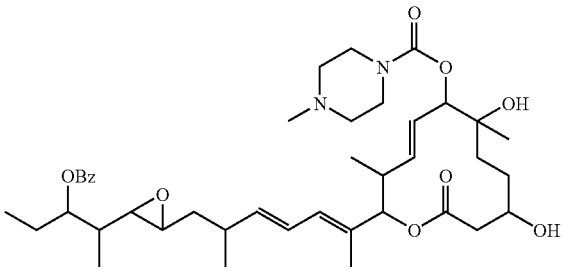

Example 1-1 Step (8E,12E,14E)-7-acetoxy-6,21-dihydroxy-6,10,12,16,20-pentamethyl-3-triethylsiloxy-18,19-epoxytricosa-8,12,14-trien-11-olide

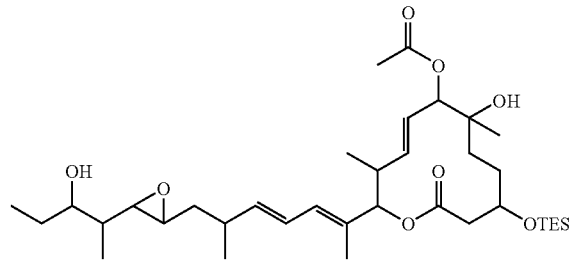

(8E,12E,14E)-7-acetoxy-3,16,21-trihydroxy-6,10,12,16,20-pentamethyl-18,19-epoxytricosa-8,12,14-trien-11-olide: 11107B (Compound of Reference Example 1) (1.0 g, 1.86 mmol) was dissolved in tetrahydrofuran (10 mL). Triethylamine (0.94 mL, 6.74 mmol) and 4-dimethylaminopyridine (117 mg, 0.96 mmol) were added to the solution, and then the solution was cooled to 0° C. Chlorotriethylsilane (0.4 mL) was slowly added to the solution, and the reaction solution was stirred at 0° C. for two hours. The reaction solution was diluted with ethyl acetate (100 mL), and the dilution was washed with purified water (10 mL) three times and brine (10 mL). The resulting organic layer was dried over sodium sulfate, and then filtered. The filtrate was concentrated. The concentrate was purified using silica gel column chromatography (MERCK Silica gel 60, 63 to 200 μm; hexane:ethyl acetate=2:1→1:1) to obtain the title compound (977 mg, 1.50 mmol, 80.6%) as a colorless oil.
$^1$H-NMR Spectrum (CD$_3$OD, 400 MHz) δ (ppm): 0.63 (6H, q, J=7.7 Hz), 0.88 (3H, d, J=5.9 Hz), 0.89 (3H, d, J=7.0 Hz), 0.93 (3H, t, J=7.3 Hz), 0.98 (9H, t, J=7.7 Hz), 1.08 (3H, d, J=6.6 Hz), 1.14-1.22 (1H, m), 1.16 (3H, s), 1.27-1.55 (6H, m), 1.58-1.71 (2H, m), 1.72 (3H, d, J=0.7 Hz), 2.05 (3H, s), 2.38 (1H, dd, J=4.8, 13.6 Hz), 2.41-2.60 (3H, m), 2.65 (1H, dd, J=2.2, 8.1 Hz), 2.72 (1H, dt, J=2.2, 5.9 Hz), 3.50 (1H, dt, J=4.8, 8.1 Hz), 3.88-3.95 (1H, m), 4.91 (1H, d, J=10.6 Hz), 5.01 (1H, d, J=9.9 Hz), 5.56 (1H, dd, J=9.9, 15.4 Hz), 5.65 (1H, dd, J=9.5, 15.4 Hz), 5.69 (1H, dd, J=9.5, 15.4 Hz), 6.09 (1H, d, J=11.0 Hz), 6.31 (1H, dd, J=11.0, 15.4 Hz); ESI-MS m/z 651 (M+H)$^+$, 673 (M+Na)$^+$.

Example 1-2 Step (8E,12E,14E)-7-acetoxy-21-benzoyloxy-6-hydroxy-6,10,12,16,20-pentamethyl-3-triethylsiloxy-18,19-epoxytricosa-8,12,14-trien-11-olide

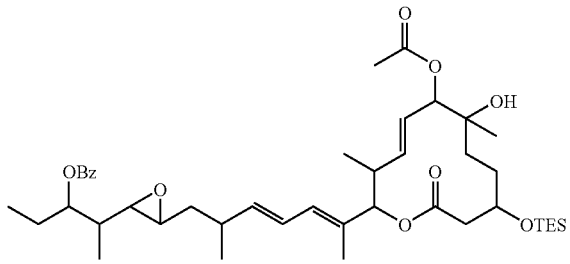

(8E,12E,14E)-7-acetoxy-6,21-dihydroxy-6,10,12,16,20-pentamethyl-3-triethylsiloxy-18,19-epoxytricosa-8,12,14-trien-11-olide (101 mg, 156 μmol) was dissolved in methylene chloride (1 mL). 4-dimethylaminopyridine (59.7 mg, 48.9 μmol) was added to the solution, and the solution was cooled to 0° C. Benzoyl chloride (28.0 μL, 241.0 μmol) was added to the solution, and the solution was stirred at room temperature for two hours. The reaction solution was diluted with ethyl acetate (20 mL), and the dilution was washed with purified water (4 mL) twice and brine (4 mL). The resulting organic layer was dried over sodium sulfate, and then filtered. The filtrate was concentrated. The concentrate was purified by silica gel column chromatography (MERCK Silica gel 60, 63 to 200 μm; hexane:ethyl acetate=5:1→4:1) to obtain the title compound (107 mg, 142 μmol, 91.0%) as a colorless oil.

$^1$H-NMR Spectrum (CD$_3$OD, 400 MHz) δ (ppm): 0.63 (6H, q, J=8.1 Hz), 0.87 (3H, d, J=6.6 Hz), 0.92 (3H, t, J=7.3 Hz), 0.98 (3H, d, J=7.0 Hz), 0.98 (9H, t, J=8.1 Hz), 1.02 (3H, d, J=7.0 Hz), 1.16 (3H, s), 1.28-1.51 (4H, m), 1.53-1.82 (5H, m), 1.71 (3H, d, J=0.7 Hz), 2.06 (3H, s), 2.35-2.48 (3H, m), 2.37 (1H, dd, J=4.4, 13.6 Hz), 2.50 (1H, dd, J=3.3, 13.6 Hz), 2.50-2.58 (1H, m), 2.60 (1H, dd, J=2.2, 7.7 Hz), 2.74 (1H, dt, J=2.2, 5.9 Hz), 3.87-3.93 (1H, m), 4.89 (1H, d, J=10.6 Hz), 5.01 (1H, d, J=9.9 Hz), 5.18 (1H, dt, J=5.5, 7.7 Hz), 5.55 (1H, dd, J=9.9, 15.4 Hz), 5.57 (1H, dd, J=8.4, 15.0 Hz), 5.69 (1H, dd, J=9.9, 15.4 Hz), 6.06 (1H, d, J=11.0 Hz), 6.28 (1H, dd, J=11.0, 15.0 Hz), 7.46-7.52 (2H, m), 7.58-7.64 (1H, m), 7.98-8.04 (2H, m); ESI-MS m/z 777 (M+Na)$^+$.

Example 1-3 Step (8E,12E,14E)-7-acetoxy-21-benzoyloxy-6-(1-ethoxyethoxy)-6,10,12,16,20-pentamethyl-3-triethylsiloxy-18,19-epoxytricosa-8,12,14-trien-11-olide

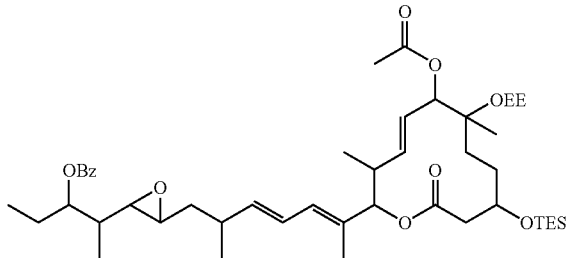

(8E,12E,14E)-7-acetoxy-21-benzoyloxy-6-hydroxy-6,10,12,16,20-pentamethyl-3-triethylsiloxy-18,19-epoxytricosa-8,12,14-trien-11-olide (95.6 mg, 127 μmol) was dissolved in methylene chloride (2 mL). Ethyl vinyl ether (200 μL, 2.09 μmol) and pyridinium p-toluenesulfonate (3.2 mg, 12.7 μmol) were added to the solution at room temperature, and the reaction solution was stirred at the same temperature for 14.5 hours. Ethyl vinyl ether (200 μl, 2.09 μmol) and pyridinium p-toluenesulfonate (2.5 mg, 9.9 μmol) were further added to the reaction solution at room temperature, and the reaction solution was stirred at the same temperature for 7.5 hours. The reaction solution was diluted with ethyl acetate (30 mL), and the dilution was washed with purified water (6 mL) twice and brine (6 mL). The resulting organic layer was dried over sodium sulfate, and then filtered. The filtrate was concentrated. The concentrate was purified by silica gel column chromatography (MERCK Silica gel 60, 63 to 200 μm; hexane:ethyl acetate=5:1) to obtain the title compound (89.1 mg, 108 μmol, 85.1%) as a colorless oil.

$^1$H-NMR Spectrum (CD$_3$OD, 400 MHz) δ (ppm): 0.61 (6H, q, J=7.7 Hz), 0.87 (3H, d, J=7.0 Hz), 0.92 (3H, t, J=7.7 Hz), 0.977 (9H, t, J=7.7 Hz), 0.984 (3H, d, J=5.5 Hz), 1.02 (3H, d, J=7.0 Hz), 1.17 (3H, t, J=7.0 Hz), 1.28 (3H, s), 1.30 (1.2H, d, J=5.1 Hz), 1.33 (1.8H, d, J=5.1 Hz), 1.33-1.83 (9H, m), 1.71 (3H, s), 2.04 (3H, s), 2.37 (1H, dd, J=4.4, 13.9 Hz), 2.37-2.45 (1.6H, m), 2.49 (1H, dd, J=4.4, 13.9 Hz), 2.49-2.58 (0.4H, m), 2.60 (1H, dd, J=2.2, 7.7 Hz), 2.74 (1H, dt, J=2.2, 5.9 Hz), 3.54 (1.2H, q, J=7.0 Hz), 3.63 (0.8H, q, J=7.0 Hz), 3.88-3.95 (1H, m), 4.90 (1H, d, J=9.5 Hz), 5.03 (1H, d, J=9.5 Hz), 5.04-5.10 (0.4H, m), 5.13-5.21 (1.6H, m), 5.55 (1H, dd, J=9.9, 15.4 Hz), 5.57 (1H, dd, J=8.4, 15.0 Hz), 5.71 (0.6H, dd, J=9.5, 15.4 Hz), 5.75 (0.4H, dd, J=9.5, 15.4 Hz), 6.06 (1H, d, J=11.0 Hz), 6.28 (1H, dd, J=11.0, 15.0 Hz), 7.45-7.52 (2H, m), 7.59-7.64 (1H, m), 7.98-8.05 (2H, m); ESI-MS m/z 849 (M+Na)$^+$.

Example 1-4 Step (8E,12E,14E)-21-benzoyloxy-6-(1-ethoxyethoxy)-7-hydroxy-6,10,12,16,20-pentamethyl-3-triethylsiloxy-18,19-epoxytricosa-8,12,14-trien-11-olide

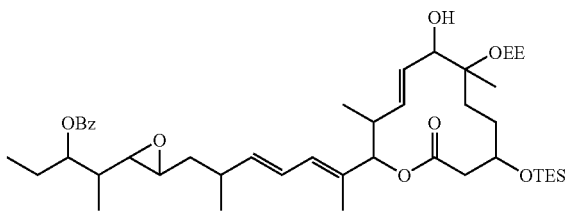

(8E,12E,14E)-7-acetoxy-21-benzoyloxy-6-(1-ethoxyethoxy)-6,10,12,16,20-pentamethyl-3-triethylsiloxy-18,19-epoxytricosa-8,12,14-trien-11-olide (89.1 mg, 108 μmol) was dissolved in methanol (3 mL), and the solution was cooled to 0° C. Potassium carbonate (30.2 mg, 219 μmol) was added to the reaction solution. The reaction solution was warmed to room temperature, and stirred at the same temperature for 3.5 hours. Acetic acid (12.3 μL, 215 μmol) was added to the reaction solution, and then the solution was concentrated. The concentrate was suspended in ethyl acetate (30 mL), and the suspension was washed with saturated aqueous solution of sodium hydrogencarbonate (6 mL) twice, purified water (6 mL) twice, and brine (6 mL). The resulting organic layer was dried over sodium sulfate, and then filtered. The filtrate was concentrated. The concentrate was purified by silica gel column chromatography (MERCK Silica gel 60, 63 to 200 μm; hexane:ethyl acetate=5:1→4:1) to obtain the title compound (60.9 mg, 77.6 μmol, 72.1%) as a colorless oil.

$^1$H-NMR Spectrum (CD$_3$OD, 400 MHz) δ (ppm): 0.62 (6H, q, J=8.1 Hz), 0.90 (3H, d, J=7.0 Hz), 0.92 (3H, t, J=7.3 Hz), 0.98 (9H, t, J=7.3 Hz), 0.99 (3H, d, J=7.3 Hz), 1.02 (3H, d, J=6.6 Hz), 1.17 (3H, t, J=7.0 Hz), 1.29-1.69 (10H, m), 1.34

(1.8H, s), 1.36 (1.2H, s), 1.72 (3H, s), 1.72-1.84 (2H, m), 2.36 (1H, dd, J=4.8, 13.6 Hz), 2.36-2.59 (3H, m), 2.60 (1H, dd, J=1.8, 7.7 Hz), 2.74 (1H, dt, J=1.8, 5.9 Hz), 3.56 (2H, q, J=7.0 Hz), 3.60 (0.4H, q, J=9.5 Hz), 3.67 (0.6H, q, J=9.5 Hz), 3.85-3.93 (1H, m), 4.83-4.92 (1H, overlapped with H$_2$O), 4.98 (0.4H, q, J=5.1 Hz), 5.12-5.21 (1.6H, m), 5.36 (1H, dd, J=9.9, 15.0 Hz), 5.57 (1H, dd, J=8.4, 15.0 Hz), 5.72 (0.4H, dd, J=9.5, 15.0 Hz), 5.77 (0.6H, dd, J=9.5, 15.0 Hz), 6.05 (1H, d, J=11.0 Hz), 6.28 (1H, dd, J=11.0, 15.0 Hz), 7.48-7.52 (2H, m), 7.59-7.66 (1H, m), 7.99-8.03 (2H, m); ESI-MS m/z 807 (M+Na)$^+$.

Example 1-5 Step (8E,12E,14E)-21-benzoyloxy-6-(1-ethoxyethoxy)-6, 10,12,16,20-pentamethyl-7-(4-nitrophenoxy)carboxy-3-triethylsiloxy-18,19-epoxytricosa-8,12,14-trien-11-olide

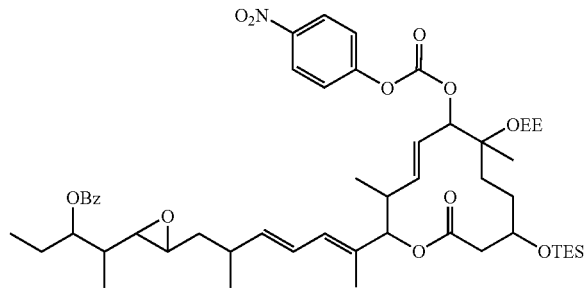

(8E,12E,14E)-21-benzoyloxy-6-(1-ethoxyethoxy)-7-hydroxy-6,10,12,16,20-pentamethyl-3-triethylsiloxy-18,19-epoxytricosa-8,12,14-trien-11-olide (57.1 mg, 72.7 μmol) was dissolved in methylene chloride (0.5 mL). Triethylamine (51.0 μL, 366 μmol) and dimethylaminopyridine (4.9 mg, 40.1 μmol) was added to the solution, and the reaction solution was cooled to 0° C. A solution of 4-nitrophenyl chloroformate (45.0 mg, 223 μmol) in methylene chloride (0.5 mL) was added to the solution. The reaction solution was warmed to room temperature and stirred for five hours. 4-Nitrophenyl chloroformate (17.8 mg, 88.3 μmol) was further added to the reaction solution, and the solution was stirred at the same temperature for two hours. The reaction solution was diluted with ethyl acetate (30 mL), and the dilution was washed with saturated aqueous solution of sodium hydrogencarbonate (10 mL) twice, purified water (10 mL) twice, and brine (10 mL). The resulting organic layer was dried over sodium sulfate, and then filtered. The filtrate was concentrated. The concentrate was purified by silica gel column chromatography (MERCK Silica gel 60, 63 to 200 μm; hexane:ethyl acetate=9:1) to obtain the title compound (106.6 mg) as a mixture.

$^1$H-NMR Spectrum (CD$_3$OD, 400 MHz) δ (ppm): 0.63 (6H, q, J=8.1 Hz), 0.90 (3H, d, J=6.6 Hz), 0.92 (3H, t, J=7.3 Hz), 0.980 (9H, t, J=8.1 Hz), 0.983 (3H, d, J=7.0 Hz), 1.02 (3H, d, J=6.6 Hz), 1.17 (1.2H, t, J=7.0 Hz), 1.18 (1.8H, t, J=7.0 Hz), 1.19-1.73 (7H, m), 1.29 (1.8H, d, J=5.5 Hz), 1.32 (1.2H, d, J=5.5 Hz), 1.41 (1.8H, s), 1.42 (1.8H, s), 1.73 (3H, s), 1.73-1.8 (2H, m), 2.36-2.68 (4H, m), 2.60 (1H, dd, J=2.2, 7.7 Hz), 2.74 (1H, dt, J=2.2, 5.9 Hz), 3.54 (1.2H, q, J=7.0 Hz), 3.62 (0.8H, q, J=7.0 Hz), 3.88-3.96 (1H, m), 4.89-4.95 (2H, m), 5.08-5.13 (1H, m), 5.18 (1H, dt, J=5.1, 7.7 Hz), 5.58 (1H, dd, J=8.4, 15.0 Hz), 5.68 (1H, dd, J=9.9, 15.4 Hz), 5.81 (0.6H, dd, J=9.5, 15.4 Hz), 5.85 (0.4H, dd, J=9.5, 15.4 Hz), 6.07 (1H, d, J=11.0 Hz), 6.28 (1H, dd, J=11.0, 15.0 Hz), 7.42-7.52 (4H, m), 7.59-7.65 (1H, m), 7.99-8.03 (2H, m), 8.29-8.33 (2H, m); ESI-MS m/z 752 (M+Na)$^+$.

Example 1-6 Step (8E,12E,14E)-21-benzoyloxy-6-(1-ethoxyethoxy)-6, 10,12,16,20-pentamethyl-7-((4-methylpiperazin-1-yl)carbonyl)oxy-3-triethylsiloxy-18,19-epoxytricosa-8,12,14-trien-11-olide

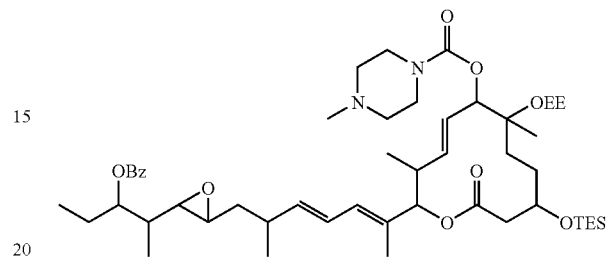

(8E,12E,14E)-21-benzoyloxy-6-(1-ethoxyethoxy)-6,10, 12,16,20-pentamethyl-7-(4-nitrophenoxy)carboxy-3-triethylsiloxy-18,19-epoxytricosa-8,12,14-trien-11-olide (98.4 mg, 108 μmol) was dissolved in tetrahydrofuran (1 mL), and the solution was cooled to 0° C. Then, methylpiperazine (12.5 μL, 113 μmol) was added to the solution, and the reaction solution was stirred for three hours. The reaction solution was concentrated, and the concentrate was purified by silica gel column chromatography (Fuji Silysia, NH Silica gel, 100 μm; hexane:ethyl acetate=10:1→5:1) to obtain the title compound (55.9 mg, 61.3 μmol, 91.4%, two steps) as a colorless oil.

$^1$H-NMR Spectrum (CD$_3$OD, 400 MHz) δ (ppm): 0.62 (6H, q, J=8.1 Hz), 0.88 (3H, d, J=6.6 Hz), 0.92 (3H, t, J=7.3 Hz), 0.975 (9H, t, J=8.1 Hz), 0.982 (3H, d, J=5.9 Hz), 1.02 (3H, d, J=7.0 Hz), 1.15 (1.2H, t, J=7.0 Hz), 1.17 (1.8H, t, J=7.0 Hz), 1.25-1.73 (9H, m), 1.287 (1.8H, s), 1.292 (1.2H, s), 1.30 (1.8H, d, J=5.1 Hz), 1.31 (1.2H, d, J=5.1 Hz), 1.71 (3H, s), 2.30 (3H, s), 2.34-2.59 (8H, m), 2.59 (1H, dd, J=2.2, 7.7 Hz), 2.73 (1H, dt, J=2.2, 5.9 Hz), 3.44-3.65 (6H, m), 3.88-3.95 (1H, m), 4.90 (1H, d, J=10.6 Hz), 4.95 (0.4H, d, J=9.5 Hz), 4.96 (0.6H, d, J=9.5 Hz), 5.04 (0.4H, q, J=5.1 Hz), 5.12 (0.6H, q, J=5.1 Hz), 5.18 (1H, dt, J=5.1, 7.0 Hz), 5.56 (1H, dd, J=9.5, 15.0 Hz), 5.57 (1H, dd, J=8.4, 15.0 Hz), 5.75 (1H, dd, J=9.5, 15.0 Hz), 6.06 (1H, d, J=11.0 Hz), 6.28 (1H, dd, J=11.0, 15.0 Hz), 7.45-7.52 (2H, m), 7.58-7.64 (1H, m), 7.98-8.04 (2H, m); ESI-MS m/z 711 (M+H)$^+$.

Example 1-7 Step (8E,12E,14E)-21-benzoyloxy-3,6-dihydroxy-6,10, 12,16,20-pentamethyl-7-((4-methylpiperazin-1-yl) carbonyl)oxy-18,19-epoxytricosa-8,12,14-trien-11-olide (Compound 1)

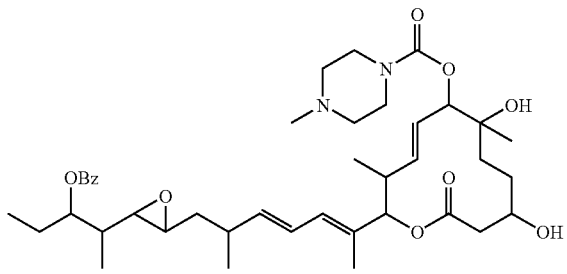

(8E,12E,14E)-21-benzoyloxy-6-(1-ethoxyethoxy)-6,10, 12,16,20-pentamethyl-7-((4-methylpiperazin-1-yl)carbonyl)oxy-3-triethylsiloxy-18,19-epoxytricosa-8,12,14-trien-11-olide (19.7 mg, 21.6 μmol) was dissolved in methanol (1 mL). Pyridinium p-toluenesulfonate (12.2 mg, 48.5 μmol) was added to the reaction solution at room temperature, and the reaction solution was stirred at the same temperature for 5.5 hours. The reaction solution was concentrated, and the concentrate was suspended in ethyl acetate (30 mL). This suspension was washed with a saturated aqueous solution of sodium hydrogencarbonate (6 mL) twice, purified water (6 mL) twice, and brine (6 mL). The resulting organic layer was dried over sodium sulfate, and then filtered. The filtrate was concentrated. The concentrate was purified by thin-layer chromatography (Fuji Silysia, NH Silica gel Plate; chloroform:methanol=40:1) to obtain the title compound (14.3 mg, 19.7 μmol, 91.2%) as a colorless oil.

¹H-NMR Spectrum (CD₃OD, 400 MHz) δ (ppm): 0.88 (3H, d, J=6.6 Hz), 0.92 (3H, t, J=7.3 Hz), 0.99 (3H, d, J=7.3 Hz), 1.02 (3H, d, J=6.6 Hz), 1.21 (3H, s), 1.31-1.43 (3H, m), 1.53-1.70 (4H, m), 1.72 (3H, s), 1.72-1.84 (2H, m), 2.29 (3H, s), 2.34-2.45 (5H, m), 2.51 (2H, d, J=3.7 Hz), 2.51-2.60 (1H, m), 2.60 (1H, dd, J=2.2, 7.7 Hz), 2.74 (1H, dt, J=2.2, 5.9 Hz), 3.38-3.72 (4H, m), 3.73-3.81 (1H, m), 4.93 (1H, d, J=9.5 Hz), 5.03 (1H, d, J=10.6 Hz), 5.18 (1H, dt, J=5.1, 7.3 Hz), 5.57 (2H, dd, J=9.5, 15.4 Hz), 5.71 (1H, dd, J=9.5, 15.4 Hz), 6.05 (1H, d, J=10.6 Hz), 6.28 (1H, dd, J=10.6, 15.4 Hz), 7.45-7.52 (2H, m), 7.59-7.64 (1H, m), 7.99-8.04 (2H, m); ESI-MS m/z 725(M+Na)⁺.

Example 2

(8E,12E,14E)-21-(N,N-dimethylcarbamoyloxy)-3,6-dihydroxy-6,10,12,16,20-pentamethyl-7-((4-methylpiperazin-1-yl)carbonyl)oxy-18,19-epoxytricosa-8,12,14-trien-11-olide (Compound 2)

Example 2-1 Step (8E,12E,14E)-7-acetoxy-6-hydroxy-6,10,12,16,20-pentamethyl-21-(4-nitrophenoxy)carboxy-3-triethylsiloxy-18,19-epoxytricosa-8,12,14-trien-11-olide

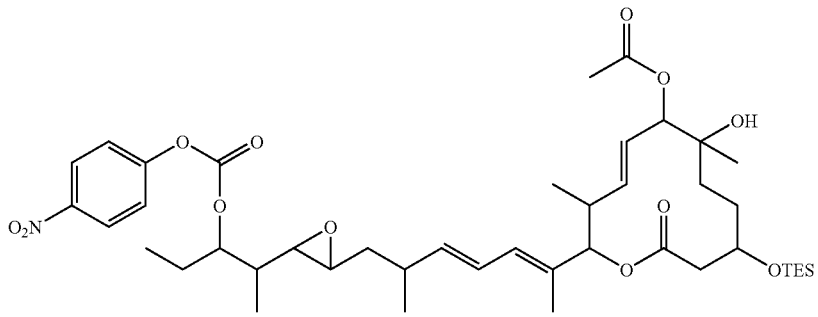

(8E,12E,14E)-7-acetoxy-6,21-dihydroxy-6,10,12,16,20-pentamethyl-3-triethylsiloxy-18,19-epoxytricosa-8,12,14-trien-11-olide (201 mg, 309 μmol) was dissolved in methylene chloride (2 mL). Triethylamine (220 μL, 1.58 μmol) and dimethylaminopyridine (17.0 mg, 139 μmol) were added to the reaction solution, and the reaction solution was cooled to 0° C. A solution of 4-nitrophenyl chloroformate (125 mg, 620 μmol) in methylene chloride (2 mL) was added to the solution. The reaction solution was warmed to room temperature, and then stirred for five hours. 4-nitrophenyl chloroformate (50.0 mg, 248 μmol) was further added to the reaction solution, and the solution was stirred at room temperature for two hours. The reaction solution was diluted with ethyl acetate (30 mL), and the dilution was washed with saturated aqueous solution of sodium hydrogencarbonate (6 mL) twice, purified water (6 mL) twice, and brine (6 mL). The resulting organic layer was dried over sodium sulfate, and then filtered. The filtrate was concentrated. The concentrate was purified by silica gel column chromatography (MERCK Silica gel 60, 63 to 200 μm; hexane:ethyl acetate=5:1→3:1) to obtain the title compound (246 mg, 302 μmol, 97.6%) as a colorless oil.

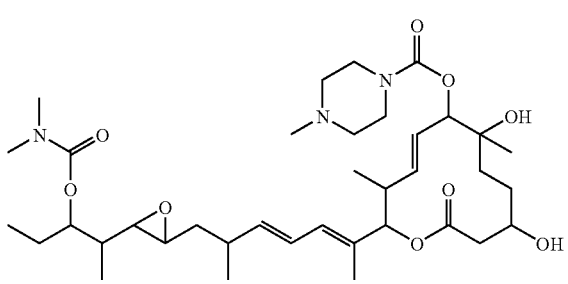

¹H-NMR Spectrum (CD₃OD, 400 MHz) δ (ppm): 0.63 (6H, q, J=8.1 Hz), 0.81 (3H, d, J=7.7 Hz), 0.93-1.02 (15H, m), 1.12 (3H, d, J=8.1 Hz), 1.16 (3H, s), 1.28-1.38 (1H, m), 1.40-1.51 (3H, m), 1.55-1.81 (5H, m), 1.72 (3H, s), 2.05 (3H, s), 2.37 (1H, dd, J=4.8, 13.6 Hz), 2.41-2.60 (3H, m), 2.64 (1H, dd, J=2.2, 8.1 Hz), 2.78 (1H, dt, J=2.2, 5.9 Hz), 3.88-3.94 (1H, m), 4.81-4.90 (1H, overlapped with H₂O), 4.90 (1H, d, J=10.6 Hz), 5.01 (1H, d, J=9.9 Hz), 5.55 (1H, dd, J=9.9, 15.4 Hz), 5.66 (1H, dd, J=8.4, 15.0 Hz), 5.69 (1H, dd, J=9.9, 15.4 Hz), 6.10 (1H, d, J=11.0 Hz), 6.31 (1H, dd, J=11.0, 15.0 Hz), 7.43-7.48 (2H, m), 8.28-8.33 (2H, m); ESI-MS m/z 838 (M+Na)⁺.

Example 2-2 Step (8E,12E,14E)-7-acetoxy-21-(N,N-dimethylcarbamoyloxy)-6-hydroxy-6,10,12,16,20-pentamethyl-3-triethylsiloxy-18,19-epoxytricosa-8,12,14-trien-11-olide

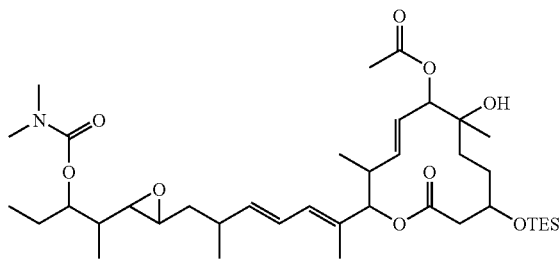

(8E,12E,14E)-7-acetoxy-6-hydroxy-6,10,12,16,20-pentamethyl-21-(4-nitrophenoxy)carboxy-3-triethylsiloxy-18,19-epoxytricosa-8,12,14-trien-11-olide (120 mg, 147 μmol) was dissolved in tetrahydrofuran (2 mL), and the solution was cooled to 0° C. Then, dimethylamine (2 M tetrahydrofuran solution, 111 μL, 221 μmol) was added to the solution, and the solution was stirred at room temperature for two hours. The reaction solution was concentrated, and the concentrate was purified by silica gel column chromatography (MERCK Silica gel 60, 63 to 200 μm; hexane:ethyl acetate=4:1→2:1) to obtain the title compound (89.0 mg, 123 μmol, 83.6%) as a colorless oil.

$^1$H-NMR Spectrum (CD$_3$OD, 400 MHz) δ (ppm): 0.63 (6H, q, J=7.7 Hz), 0.869 (3H, d, J=7.3 Hz), 0.871 (3H, d, J=5.5 Hz), 0.90 (3H, t, J=7.0 Hz), 0.98 (9H, t, J=7.7 Hz), 1.07 (3H, d, J=7.0 Hz), 1.16 (3H, s), 1.27-1.53 (5H, m), 1.54-1.70 (4H, m), 1.72 (3H, d, J=1.1 Hz), 2.05 (3H, s), 2.38 (1H, dd, J=3.3, 13.6 Hz), 2.40-2.51 (1H, m), 2.51-2.60 (1H, m), 2.51 (1H, dd, J=3.3, 13.6 Hz), 2.56 (1H, dd, J=2.2, 7.7 Hz), 2.71 (1H, dt, J=2.2, 5.9 Hz), 2.90 (3H, brs), 2.92 (3H, brs), 3.88-3.95 (1H, m), 4.72-4.78 (1H, m), 4.90 (1H, d, J=10.6 Hz), 5.01 (1H, d, J=9.5 Hz), 5.56 (1H, dd, J=9.9, 15.0 Hz), 5.65 (1H, dd, J=8.4, 15.0 Hz), 5.69 (1H, dd, J=9.9, 15.0 Hz), 6.09 (1H, d, J=11.0 Hz), 6.31 (1H, dd, J=11.0, 15.0 Hz); ESI-MS m/z 744 (M+Na)$^+$.

Example 2-3 Step (8E,12E,14E)-7-acetoxy-21-(N,N-dimethylcarbamoyloxy)-6-(1-ethoxyethoxy)-6,10,12,16,20-pentamethyl-3-triethylsiloxy-18,19-epoxytricosa-8,12,14-trien-11-olide

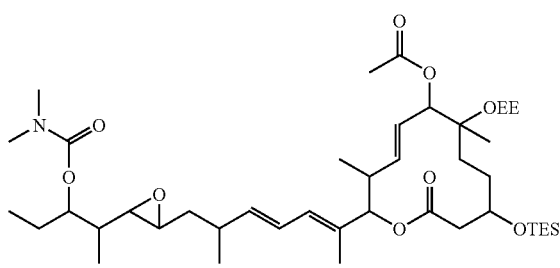

The title compound (colorless oil) was synthesized in the same manner as in the Example 1-3 step.

$^1$H-NMR Spectrum (CD$_3$OD, 400 MHz) δ (ppm): 0.63 (6H, q, J=8.1 Hz), 0.87 (3H, d, J=7.0 Hz), 0.886 (3H, d, J=7.0 Hz), 0.894 (3H, t, J=7.0 Hz), 0.98 (9H, t, J=8.1 Hz), 1.07 (3H, d, J=6.6 Hz), 1.17 (3H, t, J=7.0 Hz), 1.28 (3H, s), 1.30 (1.2H, d, J=5.1 Hz), 1.33 (1.8H, d, J=5.1 Hz), 1.39-1.72 (9H, m), 1.73 (3H, s), 2.04 (3H, s), 2.38 (1H, dd, J=4.4, 13.6 Hz), 2.38-2.60 (3H, m), 2.56 (1H, dd, J=2.2, 7.7 Hz), 2.71 (1H, dt, J=2.2, 5.9 Hz), 2.90 (3H, brs), 2.92 (3H, brs), 3.54 (1.2H, q, J=7.0 Hz), 3.63 (0.8H, q, J=7.0 Hz), 3.88-3.96 (1H, m), 4.72-4.78 (1H, m), 4.91 (1H, d, J=10.3 Hz), 5.03 (0.6H, d, J=9.5 Hz), 5.05 (0.4H, d, J=9.5 Hz), 5.06 (0.6H, q, J=5.1 Hz), 5.17 (0.4H, q, J=5.1 Hz), 5.55 (1H, dd, J=9.5, 15.4 Hz), 5.65 (1H, dd, J=8.4, 15.0 Hz), 5.71 (0.6H, dd, J=9.5, 15.4 Hz), 5.75 (0.4H, dd, J=9.5, 15.4 Hz), 6.09 (1H, d, J=11.0 Hz), 6.31 (1H, dd, J=11.0, 15.0 Hz); ESI-MS m/z 816 (M+Na)$^+$.

Example 2-4 Step (8E,12E,14E)-21-(N,N-dimethylcarbamoyloxy)-6-(1-ethoxyethoxy)-7-hydroxy-6,10,12,16,20-pentamethyl-3-triethylsiloxy-18,19-epoxytricosa-8,12,14-trien-11-olide

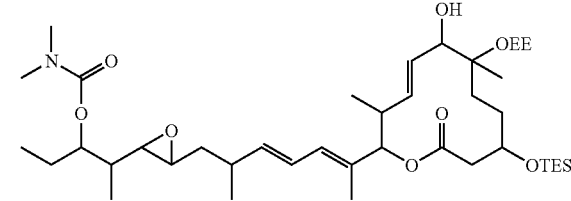

The title compound (colorless oil) was synthesized in the same manner as in the Example 1-4 step.

$^1$H-NMR Spectrum (CD$_3$OD, 400 MHz) δ (ppm): 0.63 (6H, q, J=8.1 Hz), 0.87 (3H, d, J=7.7 Hz), 0.897 (3H, t, J=7.3 Hz), 0.898 (3H, d, J=6.6 Hz), 0.90 (3H, d, J=6.6 Hz), 0.98 (9H, t, J=8.1 Hz), 1.07 (3H, d, J=7.0 Hz), 1.17 (3H, t, J=7.3 Hz), 1.30 (1.2H, d, J=5.1 Hz), 1.31 (1.8H, d, J=5.1 Hz), 1.33 (1.8H, s), 1.36 (1.2H, s), 1.38-1.70 (9H, m), 1.73 (3H, s), 2.33-2.59 (4H, m), 2.56 (1H, dd, J=2.2, 8.1 Hz), 2.71 (1H, dt, J=2.2, 5.9 Hz), 2.90 (3H, brs), 2.92 (3H, brs), 3.55 (2H, q, J=7.3 Hz), 3.60 (0.4H, d, J=9.5 Hz), 3.67 (0.6H, d, J=9.5 Hz), 3.85-3.93 (1H, m), 4.73-4.78 (1H, m), 4.90 (0.4H, d, J=11.0 Hz), 4.91 (0.6H, d, J=11.0 Hz), 4.98 (0.4H, q, J=5.1 Hz), 5.15 (0.6H, q, J=5.1 Hz), 5.36 (1H, dd, J=9.9, 15.4 Hz), 5.64 (1H, dd, J=8.4, 15.0 Hz), 5.72 (0.4H, dd, J=9.5, 15.4 Hz), 5.77 (0.6H, dd, J=9.5, 15.4 Hz), 6.08 (1H, d, J=10.6 Hz), 6.32 (1H, dd, J=10.6, 15.0 Hz); ESI-MS m/z 774 (M+Na)$^+$.

Example 2-5 Step (8E,12E,14E)-21-(N,N-dimethylcarbamoyloxy)-6-(1-ethoxyethoxy)-6,10,12,16,20-pentamethyl-7-(4-nitrophenoxy)carboxy-3-triethylsiloxy-18,19-epoxytricosa-8,12,14-trien-11-olide

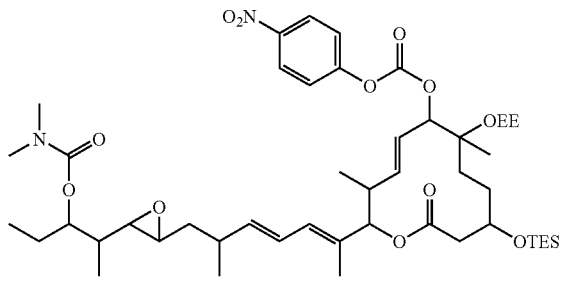

The title compound (colorless oil) was synthesized in the same manner as in the Example 1-5 step.

$^1$H-NMR Spectrum (CD$_3$OD, 400 MHz) δ (ppm): 0.64 (6H, q, J=8.1 Hz), 0.88 (3H, t, J=7.3 Hz), 0.91 (6H, d, J=7.0 Hz), 0.99 (9H, t, J=8.1 Hz), 1.07 (3H, d, J=6.6 Hz), 1.17 (1.2H, t, J=7.0 Hz), 1.18 (1.8H, t, J=7.0 Hz), 1.29 (1.8H, d, J=5.1 Hz), 1.32 (1.2H, d, J=5.1 Hz), 1.41 (1.8H, s), 1.42 (1.2H, s), 1.42-1.70 (9H, m), 1.74 (3H, s), 2.40 (1H, dd, J=4.4, 13.6 Hz), 2.40-2.57 (3H, m), 2.56 (1H, dd, J=2.2, 7.7 Hz), 2.71 (1H, dt, J=2.2, 5.9 Hz), 2.90 (3H, brs), 2.92 (3H, brs), 3.54 (1.2H, q, J=7.0 Hz), 3.62 (0.8H, q, J=7.0 Hz), 3.89-3.98 (1H, m), 4.76 (1H, dt, J=5.5, 7.3 Hz), 4.91 (1H, d, J=9.5 Hz), 4.93 (1H, d, J=10.3 Hz), 5.08-5.13 (1H, m), 5.65 (1H, dd, J=8.8, 15.0 Hz), 5.69 (1H, dd, J=9.9, 15.4 Hz), 5.81 (0.6H, dd, J=9.5, 15.4 Hz), 5.86 (0.4H, dd, J=9.5, 15.4 Hz), 6.10 (1H, d, J=11.0 Hz), 6.32 (1H, dd, J=11.0, 15.0 Hz), 7.42-7.49 (2H, m), 8.28-8.33 (2H, m); ESI-MS m/z 939 (M+Na)$^+$.

Example 2-6 Step (8E,12E,14E)-21-(N,N-dimethylcarbamoyloxy)-6-(1-ethoxyethoxy)-6,10,12,16,20-pentamethyl-7-((4-methylpiperazin-1-yl)carbonyl)oxy-3-triethylsiloxy-18,19-epoxytricosa-8,12,14-trien-11-olide

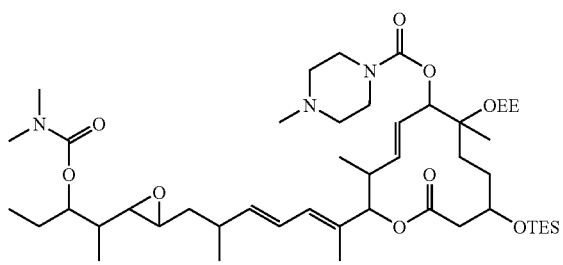

The title compound (colorless oil) was synthesized in the same manner as in the Example 1-6 step.

$^1$H-NMR Spectrum (CD$_3$OD, 400 MHz) δ (ppm): 0.63 (6H, q, J=8.1 Hz), 0.87 (3H, d, J=7.3 Hz), 0.89 (3H, d, J=7.3 Hz), 0.90 (3H, d, J=7.3 Hz), 0.98 (9H, t, J=8.1 Hz), 1.07 (3H, d, J=7.0 Hz), 1.15 (1.2H, t, J=7.0 Hz), 1.17 (1.8H, t, J=7.0 Hz), 1.290 (1.8H, s), 1.291 (1.8H, d, J=5.1 Hz), 1.311 (1.2H, s), 1.312 (1.2H, d, J=5.1 Hz), 1.39-1.73 (9H, m), 1.73 (3H, s), 2.29 (3H, s), 2.36-2.60 (8H, m), 2.56 (1H, dd, J=2.2, 7.7 Hz), 2.71 (1H, dt, J=2.2, 5.9 Hz), 2.90 (3H, brs), 2.92 (3H, brs), 3.40-3.66 (6H, m), 3.88-3.96 (1H, m), 4.75 (1H, dt, J=5.5, 7.3 Hz), 4.91 (1H, d, J=10.6 Hz), 4.94 (0.4H, d, J=9.9 Hz), 4.95 (0.6H, d, J=9.9 Hz), 5.04 (0.4H, q, J=5.1 Hz), 5.12 (0.6H, q, J=5.1 Hz), 5.56 (1H, dd, J=9.9, 15.4 Hz), 5.65 (1H, dd, J=8.4, 15.0 Hz), 5.75 (1H, dd, J=9.9, 15.4 Hz), 6.09 (1H, d, J=11.0 Hz), 6.31 (1H, dd, J=11.0, 15.0 Hz); ESI-MS m/z 878 (M+Na)$^+$.

Example 2-7 Step (8E,12E,14E)-21-(N,N-dimethylcarbamoyloxy)-3,6-dihydroxy-6,10,12,16,20-pentamethyl-7-((4-methylpiperazin-1-yl)carbonyl)oxy-18,19-epoxytricosa-8,12,14-trien-11-olide (Compound 2)

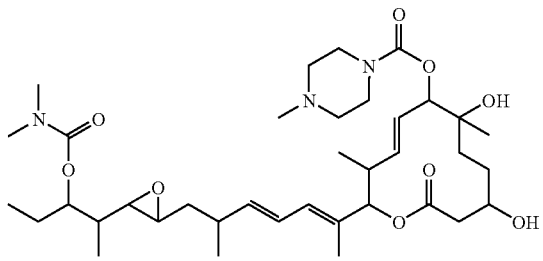

The title compound (colorless oil) was synthesized in the same manner as in the Example 1-7 step.

$^1$H-NMR Spectrum (CD$_3$OD, 400 MHz) δ (ppm): 0.88 (3H, d, J=6.6 Hz), 0.88 (3H, t, J=7.3 Hz), 0.90 (3H, d, J=7.0 Hz), 1.07 (3H, d, J=6.6 Hz), 1.20 (3H, s), 1.34-1.71 (9H, m), 1.74 (3H, s), 2.29 (3H, s), 2.48-2.62 (6H, m), 2.51 (2H, d, J=3.7 Hz), 2.56 (1H, dd, J=2.2, 7.7 Hz), 2.71 (1H, dt, J=2.2, 5.9 Hz), 2.90 (3H, s), 2.92 (3H, s), 3.38-3.70 (4H, m), 3.75-3.81 (1H, m), 4.75 (1H, dt, J=5.5, 7.3 Hz), 4.92 (1H, d, J=9.9 Hz), 5.04 (1H, d, J=10.6 Hz), 5.56 (1H, dd, J=9.9, 15.0), 5.64 (1H, dd, J=8.4, 15.0 Hz), 5.71 (1H, dd, J=9.9, 15.0 Hz), 6.08 (1H, d, J=10.6 Hz), 6.31 (1H, dd, J=10.6, 15.0 Hz); ESI-MS m/z 692 (M+H)$^+$.

Example 3

(8E,12E,14E)-3,6-dihydroxy-6,10,12,16,20-pentamethyl-7-((4-methylpiperazin-1-yl)carbonyl)oxy-21-(N-phenylcarbamoyloxy)-18,19-epoxytricosa-8,12,14-trien-11-olide (Compound 3)

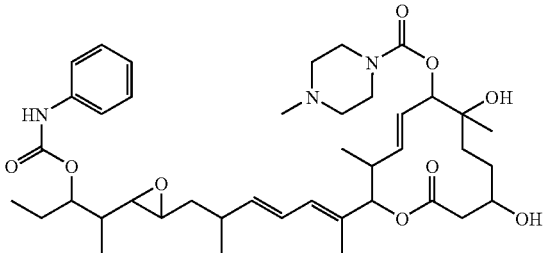

Example 3-1 Step (8E,12E,14E)-7-acetoxy-6-hydroxy-6,10,12,16,20-pentamethyl-21-(N-phenylcarbamoyloxy)-3-triethylsiloxy-18,19-epoxytricosa-8,12,14-trien-11-olide

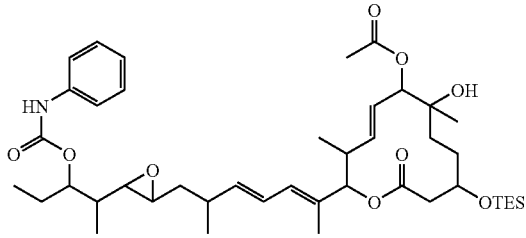

(8E,12E,14E)-7-acetoxy-6,21-dihydroxy-6,10,12,16,20-pentamethyl-3-triethylsiloxy-18,19-epoxytricosa-8,12,14-trien-11-olide (100 mg, 154 μmol) was dissolved in methylene chloride (2 mL). Triethylamine (64.2 μL, 461 μmol) and phenyl isocyanate (34.0 μL, 312 μmol) were added to the reaction solution. The reaction solution was stirred at room temperature for 25.5 hours. Then, triethylamine (200 μL, 1.43 μmol) and phenyl isocyanate (98.0 μL, 900 μmol) were further added to the reaction solution, and the reaction solution was stirred at room temperature for six hours. The reaction solution was diluted with ethyl acetate (30 mL), and the dilution was washed with saturated aqueous solution of sodium hydrogencarbonate (6 mL) twice, purified water (6 mL) twice, and brine (6 mL). The resulting organic layer was dried over sodium sulfate, and then filtered. The filtrate was concentrated. The concentrate was purified by silica gel column chromatography (MERCK Silica gel 60, 63 to 200 μm; hexane:ethyl acetate=4:1→3:1) and thin-layer chromatography (MERCK 60 F254, 0.5 mm, toluene:acetone=5:1) to obtain the title compound (54.0 mg, 70.1 μmol, 45.6%) as a colorless oil.

$^1$H-NMR Spectrum (CD$_3$OD, 400 MHz) δ (ppm): 0.62 (6H, q, J=8.1 Hz), 0.87 (3H, d, J=7.0 Hz), 0.93 (3H, d, J=7.7 Hz), 0.94 (3H, t, J=7.0 Hz), 0.98 (9H, t, J=8.1 Hz), 1.04 (3H, d, J=6.6 Hz), 1.16 (3H, s), 1.27-1.73 (9H, m), 1.71 (3H, s), 2.06 (3H, s), 2.37 (1H, dd, J=4.8, 13.6 Hz), 2.37-2.48 (1H, m), 2.50 (1H, dd, J=3.3, 13.6 Hz), 2.50-2.59 (1H, m), 2.64 (1H, dd, J=2.2, 7.7 Hz), 2.74 (1H, dt, J=2.2, 5.9 Hz), 3.84 (1H, m), 4.81-4.92 (2H, overlapped with H$_2$O), 5.01 (1H, d, J=9.9 Hz), 5.55 (1H, dd, J=9.9, 15.0 Hz), 5.61 (1H, dd, J=8.4, 15.0 Hz), 5.69 (1H, dd, J=9.9, 15.0 Hz), 6.07 (1H, d, J=11.0 Hz), 6.28 (1H, dd, J=11.0, 15.0 Hz), 6.97-7.02 (1H, m), 7.23-7.18 (2H, m), 7.38-7.48 (2H, m); ESI-MS m/z 792 (M+Na)$^+$.

Example 3-2 Step (8E,12E,14E)-7-acetoxy-6-(1-ethoxyethoxy)-6,10,12,16,20-pentamethyl-21-(N-phenylcarbamoyloxy)-3-triethylsiloxy-18,19-epoxytricosa-8,12,14-trien-11-olide

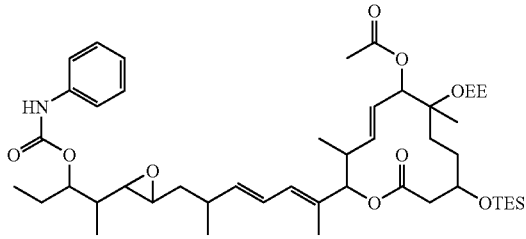

The title compound (colorless oil) was synthesized in the same manner as in the Example 1-3 step.

$^1$H-NMR Spectrum (CD$_3$OD, 400 MHz) δ (ppm): 0.62 (6H, q, J=8.1 Hz), 0.87 (3H, d, J=6.6 Hz), 0.94 (3H, t, J=7.7 Hz), 0.98 (9H, t, J=8.1 Hz), 1.04 (3H, d, J=6.6 Hz), 1.17 (3H, t, J=7.0 Hz), 1.28 (3H, s), 1.30 (1.2H, d, J=5.1 Hz), 1.33 (1.8H, d, J=5.1 Hz), 1.40-1.63 (6H, m), 1.65-1.71 (3H, m), 1.71 (3H, s), 2.04 (3H, s), 2.37 (1H, dd, J=4.4, 13.9 Hz), 2.37-2.58 (2H, m), 2.49 (1H, dd, J=2.9, 13.9 Hz), 2.64 (1H, dd, J=2.2, 7.3 Hz), 2.74 (1H, dt, J=2.2, 5.9 Hz), 3.54 (1.2H, q, J=7.0 Hz), 3.63 (0.8H, q, J=7.3 Hz), 3.84-3.93 (1H, m), 4.80-4.92 (2H, overlapped with H$_2$O), 5.02 (0.4H, d, J=9.5 Hz), 5.05 (0.6H, d, J=9.5 Hz), 5.06 (0.4H, q, J=5.1 Hz), 5.18 (0.6H, q, J=5.1 Hz), 5.54 (1H, dd, J=9.9, 15.8 Hz), 5.61 (1H, dd, J=8.4, 15.0 Hz), 5.71 (0.6H, dd, J=9.5, 15.8 Hz), 5.75 (0.4H, dd, J=9.5, 15.8 Hz), 6.07 (1H, d, J=10.6 Hz), 6.28 (1H, dd, J=10.6, 15.0 Hz), 7.00 (1H, dd, J=7.3, 7.3 Hz), 7.26 (2H, dd, J=7.3, 8.1 Hz), 7.42 (2H, d, J=8.1 Hz); ESI-MS m/z 864 (M+Na)$^+$.

Example 3-3 Step (8E,12E,14E)-6-(1-ethoxyethoxy)-7-hydroxy-6,10,12,16,20-pentamethyl-21-(N-phenylcarbamoyloxy)-3-triethylsiloxy-18,19-epoxytricosa-8,12,14-trien-11-olide

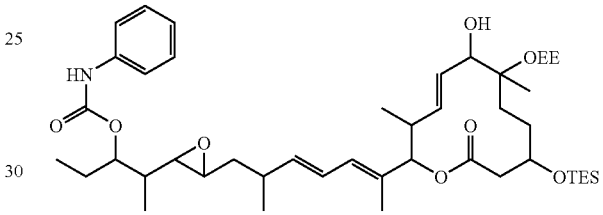

The title compound (colorless oil) was synthesized in the same manner as in the Example 1-4 step.

$^1$H-NMR Spectrum (CD$_3$OD, 400 MHz) δ (ppm): 0.62 (6H, q, J=8.1 Hz), 0.90 (3H, d, J=6.6 Hz), 0.93 (3H, d, J=7.3 Hz), 0.94 (3H, t, J=7.0 Hz), 0.98 (9H, t, J=8.1 Hz), 1.04 (3H, d, J=6.6 Hz), 1.17 (1.2H, t, J=7.0 Hz), 1.18 (1.8H, t, J=7.0 Hz), 1.30 (1.8H, s), 1.31 (1.2H, s), 1.33 (3H, t, J=8.8 Hz), 1.38-1.71 (9H, m), 1.71 (3H, s), 2.33-2.60 (4H, m), 2.64 (1H, dd, J=2.2, 7.3 Hz), 2.74 (1H, dt, J=2.2, 5.9 Hz), 3.53-3.65 (2H, m), 3.60 (0.4H, d, J=9.5 Hz), 3.67 (0.6H, d, J=9.5 Hz), 3.83-3.92 (1H, m), 4.82-4.91 (2H, overlapped with H$_2$O), 4.98 (0.4H, q, J=5.1 Hz), 5.15 (0.6H, q, J=5.1 Hz), 5.36 (1H, dd, J=9.5, 15.0 Hz), 5.60 (1H, dd, J=8.4, 15.0 Hz), 5.72 (0.4H, dd, J=9.5, 15.0 Hz), 5.77 (0.6H, dd, J=9.5, 15.0 Hz), 6.06 (1H, d, J=11.0 Hz), 6.28 (1H, dd, J=11.0, 15.0 Hz), 7.00 (1H, dd, J=7.3, 7.3 Hz), 7.26 (2H, dd, J=7.3, 8.1 Hz), 7.42 (2H, d, J=8.1 Hz); ESI-MS m/z 822 (M+Na)$^+$.

Example 3-4 Step (8E,12E,14E)-6-(1-ethoxyethoxy)-6,10,12,16,20-pentamethyl-7-(4-nitrophenoxy)carboxy-21-(N-phenylcarbamoyloxy)-3-triethylsiloxy-18,19-epoxytricosa-8,12,14-trien-11-olide

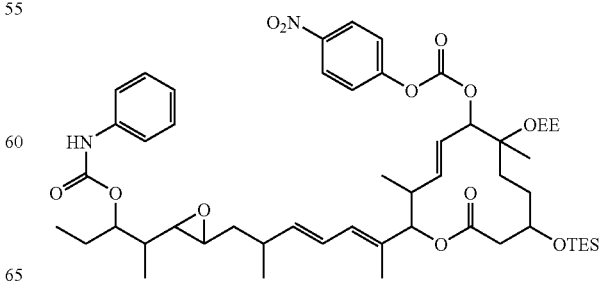

The title compound (colorless oil) was synthesized in the same manner as in the Example 1-5 step.

¹H-NMR Spectrum (CD₃OD, 400 MHz) δ (ppm): 0.63 (6H, q, J=8.1 Hz), 0.90 (3H, d, J=6.6 Hz), 0.93 (3H, d, J=5.9 Hz), 0.94 (3H, t, J=8.8 Hz), 0.98 (9H, t, J=8.1 Hz), 1.04 (3H, d, J=6.6 Hz), 1.17 (1.2H, t, J=7.0 Hz), 1.18 (1.8H, t, J=7.0 Hz), 1.29 (1.8H, d, J=5.1 Hz), 1.32 (1.2H, d, J=5.1 Hz), 1.41 (1.8H, s), 1.42 (1.2H, s), 1.41-1.73 (9H, m), 1.73 (3H, s), 2.38 (1H, dd, J=4.4, 13.9 Hz), 2.38-2.64 (3H, m), 2.64 (1H, dd, J=2.2, 7.7 Hz), 2.74 (1H, dt, J=2.2, 5.9 Hz), 3.54 (1.2H, q, J=7.0 Hz), 3.62 (0.8H, q, J=7.0 Hz), 3.88-3.96 (1H, m), 4.83-4.93 (3H, overlapped with H₂O), 5.08-5.13 (1H, m), 5.61 (1H, dd, J=8.4, 15.0 Hz), 5.68 (1H, dd, J=9.5, 15.4 Hz), 5.81 (0.6H, dd, J=9.5, 15.4 Hz), 5.85 (0.4H, dd, J=9.5, 15.4 Hz), 6.08 (1H, d, J=11.0 Hz), 6.28 (1H, dd, J=11.0, 15.0 Hz), 6.99 (1H, dd, J=7.3, 7.3 Hz), 7.25 (2H, dd, J=7.3, 7.7 Hz), 7.42 (2H, d, J=7.7 Hz), 7.43-7.49 (2H, m), 8.31 (2H, d, J=9.2 Hz); ESI-MS m/z 987 (M+Na)⁺.

Example 3-5 Step (8E,12E,14E)-6-(1-ethoxyethoxy)-6,10,12,16,20-pentamethyl-7-((4-methylpiperazin-1-yl)carbonyl)oxy-21-(N-phenylcarbamoyloxy)-3-triethylsiloxy-18,19-epoxytricosa-8,12,14-trien-11-olide

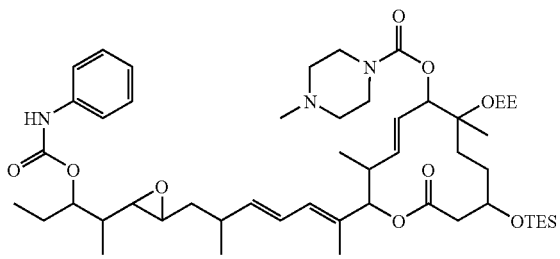

The title compound (colorless oil) was synthesized in the same manner as in the Example 1-6 step.
¹H-NMR Spectrum (CD₃OD, 400 MHz) δ (ppm): 0.62 (6H, q, J=8.1 Hz), 0.88 (3H, d, J=7.0 Hz), 0.93 (3H, d, J=5.9 Hz), 0.96 (3H, t, J=7.7 Hz), 0.98 (9H, t, J=8.1 Hz), 1.04 (3H, d, J=7.0 Hz), 1.17 (1.2H, t, J=7.0 Hz), 1.18 (1.8H, t, J=7.0 Hz), 1.28 (1.8H, s), 1.29 (1.2H, s), 1.308 (1.2H, d, J=5.1 Hz), 1.314 (1.8H, d, J=5.1 Hz), 1.41-1.72 (9H, m), 1.72 (3H, s), 2.29(3H, s), 2.34-2.60 (8H, m), 2.64 (1H, dd, J=2.2, 7.3 Hz), 2.74 (1H, dt, J=2.2, 5.9 Hz), 3.46-3.61 (6H, m), 3.85-3.94 (1H, m), 4.83-4.91 (2H, overlapped with H₂O), 4.94 (0.4H, d, J=9.5 Hz), 4.95 (0.6H, d, J=9.5 Hz), 5.04 (0.4H, q, J=5.1 Hz), 5.12 (0.6H, q, J=5.1 Hz), 5.55 (1H, dd, J=9.5, 15.4 Hz), 5.60 (1H, dd, J=8.8, 15.4 Hz), 5.74 (1H, dd, J=9.5, 15.4 Hz), 6.07 (1H, d, J=11.0 Hz), 6.28 (1H, dd, J=11.0, 15.4 Hz), 7.00 (1H, dd, J=7.3, 7.3 Hz), 7.26 (2H, dd, J=7.3, 8.1 Hz), 7.42 (2H, d, J=8.1 Hz); ESI-MS m/z 926 (M+H)⁺.

Example 3-6 Step (8E,12E,14E)-3,6-dihydroxy-6,10,12,16,20-pentamethyl-7-((4-methylpiperazin-1-yl)carbonyl)oxy-21-(N-phenylcarbamoyloxy)-18,19-epoxytricosa-8,12,14-trien-11-olide (Compound 3)

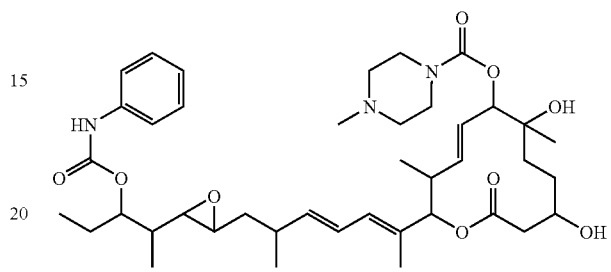

The title compound (colorless oil) was synthesized in the same manner as in the Example 1-7 step.
¹H-NMR Spectrum (CD₃OD, 400 MHz) δ (ppm): 0.87 (3H, d, J=7.0 Hz), 0.93 (3H, d, J=7.3 Hz), 0.94 (3H, t, J=7.3 Hz), 1.04 (3H, d, J=7.0 Hz), 1.20 (3H, s), 1.28-1.72 (9H, m), 1.72 (3H, s), 2.29 (3H, s), 2.51 (2H, d, J=3.7 Hz), 2.37-2.60 (6H, m), 2.64 (1H, dd, J=2.2, 7.3 Hz), 2.74 (1H, dt, J=2.2, 5.9 Hz), 3.42-3.69 (4H, m), 3.73-3.80 (1H, m), 4.80-4.92 (1H, overlapped with H₂O), 4.92 (1H, d, J=9.5 Hz), 5.03 (1H, d, J=10.6 Hz), 5.56 (1H, dd, J=9.5, 15.4 Hz), 5.60 (1H, dd, J=8.4, 15.4 Hz), 5.70 (1H, dd, J=9.5, 15.4 Hz), 6.06 (1H, d, J=11.0 Hz), 6.28 (1H, dd, J=11.0, 15.4 Hz), 7.00 (1H, dd, J=7.3, 7.3 Hz), 7.26 (2H, dd, J=7.3, 8.1 Hz), 7.42 (2H, d, J=8.1 Hz); ESI-MS m/z 740 (M+H)⁺.

INDUSTRIAL APPLICABILITY

According to the present invention, the compound of the formula (I) of the present invention inhibits, in particular, VEGF production and angiogenesis by altering gene expression, and exhibits an excellent antitumor effect in a in vivo solid cancer model. Furthermore, since the compound of the formula (I) of the present invention is stable in an aqueous solution, the present invention can provide a cancer treating agent, in particular, a solid cancer treating agent, cancer metastasis inhibitor, diabetic retinopathy treating agent, rheumatoid arthritis treating agent or ecchymoma treating agent, for example.

The invention claimed is:

1. A compound represented by the formula (I):

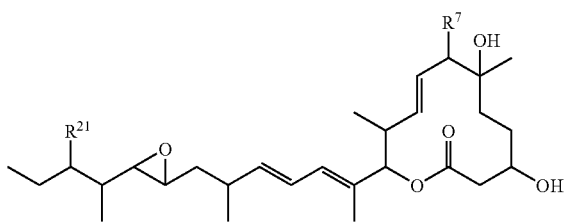

wherein $R^7$ and $R^{21}$ are the same or are different and represent
—O-benzoyl, or
RC(=Y)—O—, wherein Y represents an oxygen atom, and R represents
4-alkyl-piperazin-1-yl, alkyl, —O-phenyl, —N,N-dialkyl or —NH-phenyl, or
a pharmacologically acceptable salt thereof.

2. A compound represented by the formula (I-a):

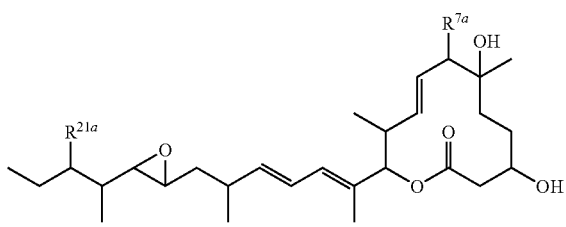

wherein $R^{7a}$ and $R^{21a}$ are the same or are different and represent $R^aC(=Y^a)$—O—, wherein $Y^a$ represents an oxygen atom, and $R^a$ represents a $C_1$ to $C_{22}$ alkyl group, an unsaturated $C_2$ to $C_{22}$ alkyl group, a $C_3$ to $C_{14}$ cycloalkyl group or a pharmacologically acceptable salt thereof.

3. The compound according to claim 1, which is (8E,12E,14E)-21-benzoyloxy-3,6-dihydroxy-6,10,12,16,20-pentamethyl-7-((4-methylpiperazin-1-yl)carbonyl)oxy-18,19-epoxytricosa-8,12,14-trien-11-olide, (8E,12E,14E)-21-(N,N-dimethylcarbamoyloxy)-3,6-dihydroxy-6,10,12,16,20-pentamethyl-7((4-methylpiperazin-1-yl)carbonyl)oxy-18,19-epoxytricosa-8,12,14-trien-11-olide, and (8E,12E,14E)-3,6-dihydroxy-6,10,12,16,20-pentamethyl-7-((4-methylpiperazin-1-yl)carbonyl)oxy-21-phenylcarbamoyloxy-18,19-epoxytricosa-8,12,14-trien-11-olide; or a pharmacologically acceptable salt thereof.

4. A pharmaceutical composition comprising the compound according to claim 1, or a pharmacologically acceptable salt thereof as an active ingredient and a pharmaceutically acceptable carrier.

* * * * *